US008974781B2

(12) United States Patent
Bauer et al.

(10) Patent No.: US 8,974,781 B2
(45) Date of Patent: Mar. 10, 2015

(54) P-CADHERIN ANTIBODIES

(75) Inventors: Christopher Todd Bauer, St. Louis, MO (US); Maureen Jeri Bourner, Defiance, MO (US); Melanie Boyle, Granta Park (GB); Gerald Fries Casperson, Ballwin, MO (US); David William Griggs, Ballwin, MO (US); Richard David Head, O'Fallon, MO (US); William Dean Joy, St. Louis, MO (US); Richard Allen Mazzarella, Webster Groves, MO (US); Ralph Raymond Minter, Granta Park (GB); Mark Allen Moffat, St. Louis, MO (US); Barrett Richard Thiele, St. Louis, MO (US); Todd Lee Vanarsdale, Carlsbad, CA (US)

(73) Assignee: Pfizer Inc., New York, NY (US)

( * ) Notice: Subject to any disclaimer, the term of this patent is extended or adjusted under 35 U.S.C. 154(b) by 1010 days.

(21) Appl. No.: 13/079,726

(22) Filed: Apr. 4, 2011

(65) Prior Publication Data

US 2011/0182884 A1  Jul. 28, 2011

Related U.S. Application Data

(63) Continuation of application No. 12/249,843, filed on Oct. 10, 2008, now Pat. No. 7,928,214, which is a continuation of application No. 11/410,610, filed on Apr. 25, 2006, now Pat. No. 7,452,537.

(60) Provisional application No. 60/675,311, filed on Apr. 26, 2005.

(51) Int. Cl.
*A61K 39/395* (2006.01)
*A61P 35/02* (2006.01)
(Continued)

(52) U.S. Cl.
CPC ............. *C07K 16/28* (2013.01); *C07K 2317/21* (2013.01); *C07K 2317/565* (2013.01); *C07K 2317/622* (2013.01); *C07K 2317/76* (2013.01); *C07K 2317/92* (2013.01)
USPC .................................... 424/130.1; 530/389.1

(58) Field of Classification Search
USPC .................................... 424/130.1; 530/389.1
See application file for complete search history.

(56) References Cited

U.S. PATENT DOCUMENTS 5,597,725 A   1/1997   Suzuki
5,610,281 A   3/1997   Brenner et al.
(Continued)

FOREIGN PATENT DOCUMENTS

JP      11 292900       10/1999
WO     WO 91/04745      4/1991
(Continued)

OTHER PUBLICATIONS

Bussemakers, M., et al., "Complex Cadherin Expression in Human Prostate Cancer Cells," *International Journal of Cancer*, 2000, 446-450, vol. 85, No. 3.
(Continued)

*Primary Examiner* — Lynn Bristol
(74) *Attorney, Agent, or Firm* — Fariba Shoarinejad

(57) ABSTRACT

The present invention relates to antibodies including human antibodies and antigen-binding portions thereof that bind to P-cadherin, and that function to inhibit P-cadherin. The invention also relates to heavy and light chain immunoglobulins derived from human P-cadherin antibodies and nucleic acid molecules encoding such immunoglobulins. The present invention also relates to methods of making human P-cadherin antibodies, compositions comprising these antibodies and methods of using the antibodies and compositions. The invention also relates to transgenic animals or plants comprising nucleic acid molecules of the present invention.

9 Claims, 26 Drawing Sheets

| SEQ ID NO. | Sequence | Description | Antibody |
|---|---|---|---|
| 1 | EVQLLESGGG LVQPGGSLRL SCAASGFTFS SYAMSWVRQA PGKGLEWVSA ISGSGGSTYY ADSVKGRFTI SRDNSKNTLY LQMNSLRAED TAVYYCASWG TGTLNPWGQG KMVTVSS | Full-length V$_H$ | 194_e06, 196_a07, 198_f06 |
| 2 | EVQLLESGGG LVQPGGSLRL SCAASGFTFS SYAMSWVRQA PGKGLEWVSA ISGSGGSTYY ADSVKGRFTI SRDNSKNTLY LQMNSLRAED TAVYYCASWG DGTLNPWGQG KMVTVSS | Full-length V$_H$ | 194_a02, 194_b09 |
| 3 | EVQLLESGGG LVQPGGSLRL SCAASGFTFS SYAMSWVRQA PGKGLEWVSA ISGSGGSTYY ADSVKGRFTI SRDNSKNTLY LQMNSLRAED TAVYYCASWG LGSNEKWGQG TMVTVSS | Full-length V$_H$ | 195_e11 |
| 4 | EVQLLESGGG LVQPGGSLRL SCAASGFTFS SYAMSWVRQA PGKGLEWVSA ISGSGGSTYY ADSVKGRFTI SRDNSKNTLY LQMNSLRAED TAVYYCADTN SAKFDPWGQG TMVTVSS | Full-length V$_H$ | 194_g09, 196_h02 |
| 5 | EVQLLESGGG LVQPGGSLRL SCAASGFTFS SYAMSWVRQA PGKGLEWVSA ISGSGGSTYY ADSVKGRFTI SRDNSKNTLY LQMNSLRAED TAVYYCAGTG YPSFDPWGQG TMVTVSS | Full-length V$_H$ | 194_e01 |
| 6 | EVQLLESGGG LVQPGGSLRL SCAASGFTFS SYAMSWVRQA PGKGLEWVSA ISGSGGSTYY ADSVKGRFTI SRDNSKNTLY LQMNSLRAED TAVYYCAGTA KPSFDPWGQG TMVTVSS | Full-length V$_H$ | 196_d10 |
| 7 | EVQLLESGGG LVQPGGSLRL SCAASGFTFS SYAMSWVRQA PGKGLEWVSA ISGSGGSTYY ADSVKGRFTI SRDNSKNTLY LQMNSLRAED TAVYYCAGNE RPSFDPWGQG TMVTVSS | Full-length V$_H$ | 196_g03 |
| 8 | EVQLLESGGG LVQPGGSLRL SCAASGFTFS SYAMSWVRQA PGKGLEWVSA ISGSGGSTYY ADSVKGRFAI SRDNSKNTLY LQMNSLRAED TAVYYCAGSR TVQFDPWGQG TMVTVSS | Full-length V$_H$ | 196_e06 |
| 9 | EVQLLESGGG LVQPGGSLRL SCAASGFTFS SYAMSWVRQA PGKGLEWVSA ISGSGGSTYY ADSVKGRFTI SRDNSKNTLY LQMNSLRAED TAVYYCATNS FGTFDPWGQG TMVTVSS | Full-length V$_H$ | 195_a09 |

(51) Int. Cl.
 C07K 16/18 (2006.01)
 C07K 16/28 (2006.01)

(56) References Cited

U.S. PATENT DOCUMENTS

| | | | |
|---|---|---|---|
| 5,646,250 | A | 7/1997 | Suzuki |
| 5,811,518 | A | 9/1998 | Ranscht |
| 5,863,804 | A | 1/1999 | Ranscht |
| 5,895,748 | A | 4/1999 | Johnson et al. |
| 5,997,866 | A | 12/1999 | Johnson et al. |
| 6,031,072 | A | 2/2000 | Blaschuk et al. |
| 6,146,630 | A | 11/2000 | Tsubota et al. |
| 6,169,071 | B1 | 1/2001 | Blaschuk et al. |
| 6,203,788 | B1 | 3/2001 | Blaschuk et al. |
| 6,207,639 | B1 | 3/2001 | Blaschuk et al. |
| 6,248,864 | B1 | 6/2001 | Blaschuk et al. |
| 6,277,824 | B1 | 8/2001 | Doherty et al. |
| 6,280,739 | B1 | 8/2001 | Jacobs et al. |
| 6,300,080 | B1 | 10/2001 | Brenner et al. |
| 6,310,177 | B1 | 10/2001 | Blaschuk et al. |
| 6,312,686 | B1 | 11/2001 | Staddon et al. |
| 6,312,921 | B1 | 11/2001 | Jacobs et al. |
| 6,326,352 | B1 | 12/2001 | Blaschuk et al. |
| 6,333,307 | B1 | 12/2001 | Blaschuk et al. |
| 6,346,512 | B1 | 2/2002 | Blaschuk et al. |
| 2002/0009739 | A1 | 1/2002 | Glese |
| 2004/0110712 | A1 | 6/2004 | Markowitz |
| 2005/0129676 | A1 | 6/2005 | Blaschuk et al. |
| 2006/0039915 | A1 | 2/2006 | Reinhard et al. |
| 2006/0040302 | A1 | 2/2006 | Botstein et al. |

FOREIGN PATENT DOCUMENTS

| | | |
|---|---|---|
| WO | WO 92/17608 | 10/1992 |
| WO | WO 93/21302 | 10/1993 |
| WO | WO 94/11401 | 5/1994 |
| WO | WO 95/13820 | 5/1995 |
| WO | WO 98/02452 | 1/1998 |
| WO | WO 98/16241 | 4/1998 |
| WO | WO 98/25946 | 6/1998 |
| WO | WO 99/08717 | 2/1999 |
| WO | WO 99/16791 | 4/1999 |
| WO | WO 00/78941 | 12/2000 |
| WO | WO 01/25492 | 4/2001 |
| WO | WO 02/08765 | 1/2002 |
| WO | WO 02/059264 | 8/2002 |
| WO | WO 02/097395 | 12/2002 |
| WO | WO 2004/018648 | 3/2004 |
| WO | WO 2004/044000 | 5/2004 |
| WO | WO 2004/072117 | 8/2004 |
| WO | WO 2004/110345 | 12/2004 |

OTHER PUBLICATIONS

De Boer, C., et al., "Changing Roles of Cadherins and Catenins during Progression of Squamous Intraepithelial Lesions in the Uterine Cervix," *American Journal of Pathology*, 1999, 505-515, vol. 155, No. 2.
Furukawa, F., "Roles of E- and P-Cadherin in the Human Skin," *Microscopy Res & Tech* (1997) 343-352, vol. 38.
Gumbiner, B.M., "Regulation of Cadherin Adhesive Activity," *J. Cell Bio.* (2000) 399-403, vol. 148, No. 3.
Gamallo, C., et al., "The Prognostic Significance of P-Cadherin in Infiltrating Ductal Breast Carcinoma," *Modern Pathology* (2001), 650-654, vol. 14.
Hardy, R.G., et al., "Aberrant P.-Cadherin Expression is an Early Event in Hyperplastic and Dysplastic Transformation in the Colon," *Gut* (2002) 513-519, vol. 50.
Hines, M., et al, "Inhibition of Cadherin Function Differentially Affects Markers of Terminal Differentiation in Cultured Human Keratinocytes," *Journal of Cell Science*, 1999, 4569-4579, vol. 112, No. 24.
Hirai, Y., et al., "Expression and Role of E- and P-Cadherin Adhesion Molecules in Embryonic Histogenesis," *Development*, 1989, 263-270, vol. 105, No. 2.
Jankowski, J., et al., "Alterations in Classical Cadherins Associated with Progression in Ulcerative and Crohn's Colitis," *Laboratory Investigations*, 1998, 1155-1167, vol. 78, No. 9.
Liu, G., et al, "Neph1 and Nephrin Interaction in the Slit Diaphragm is an Important Determinant of Glomerular Permeability," *The Journal of Clinical Investigation*, 2003, 209-221, vol. 112, No. 2.
Nose, A., et al., "A Novel Cadherin Cell Adhesion Molecule: Its Expression Patterns Associated with Implantation and Organogenesis of Mouse Embryos," *Journal of Cell Biology*, 1986, 2649-2658, vol. 103, No. 6.
Palacios, J., et al., "Anomalous Expression of P-Cadherin in Breast Carcinoma. Correlation with E-Cadherin Expression and Pathological Features," *American Journal of Pathology*, 1995, 605-612, vol. 146, No. 3.
Radice, G., et al., "Precocious Mammary Gland Development in P-Cadherin-Deficient Mice," *The Journal of Cell Biology*, 1997, 1025-1032, vol. 139, No. 4.
Rasbridge, S., et al., "Epithelial (E-) and Placentae (P-) Cadherin Cell Adhesion Molecule Expression in Breast Carcinoma," *Journal of Pathology*, 1993, 245-250, vol. 169, No. 2.
Sanders, D., et al., "Aberrant P-Cadherin Expression is a Feature of Clonal Expansion in the Gastrointestinal Tract Associated with Repair and Neoplasia," *Journal of Pathology*, 2000, 526-530, vol. 190, No. 5.
*Seikagaku*, 2002, 871, vol. 74, No. 8.
Shimoyama, Y., et al., "Cadherin Cell-adhesion Molecules in Human Epithelial Tissues and Carcinomas," *Cancer Res.* (1989) 2128-2133, vol. 49.
Shimoyama, Y., "Molecular Cloning of a Human Ca2+-dependent Cell-Cell Adhesion Molecule Homologous to Mouse Placental Cadherin: Its Low Expression in Human Placental Tissues," *J. Cell Biology* (1989) 17888-1794, vol. 109.
Stefansson, I.M., et al., "Prognostic Impact of Alterations in P-Cadherin Expression and Related Cell Adhesion Markers in Endometrial Cancer," *J. Clin. Oncology* (2004), 1242-1252, vol. 22, No. 7.
Takeichi, M., "Cadherin Cell Adhesion Receptors as a Morphogenetic Regulator," *Science* (1991), 1451-1455, vol. 251.
Williams, H., et al., "Expression of Cadherins and Catenins in Oral Epithelial Dysplasia and Squamous Cell Carcinoma," *Journal of Oral Pathology and Medicine*, 1998, 308-317, vol. 27, No. 7.
Yagi, T., et al., "Cadherin Superfamily Genes: Functions, Genomic Organization, and Neurologic Diversity," *Genes Dev.*, (2000) 1169-1180, vol. 14.
Yasui, W., et al, "Expression of P-Cadherin in Gastric Carcinomas and its Reduction in tumor Progression," *International Journal of Cancer*, 1993, 49-52, vol. 54, No. 1.

| SEQ ID NO. | Sequence | Description | Antibody |
|---|---|---|---|
| 1 | EVQLLESGGG LVQPGGSLRL SCAASGFTFS SYAMSWVRQA PGKGLEWVSA ISGSGGSTYY ADSVKGRFTI SRDNSKNTLY LQMNSLRAED TAVYYCASWG TGTLWPWGQG KMVTVSS | Full-length V$_H$ | 194_e06, 196_a07, 198_f06 |
| 2 | EVQLLESGGG LVQPGGSLRL SCAASGFTFS SYAMSWVRQA PGKGLEWVSA ISGSGGSTYY ADSVKGRFTI SRDNSKNTLY LQMNSLRAED TAVYYCASWG DGTLNPWGQG KMVTVSS | Full-length V$_H$ | 194_a02, 194_b09 |
| 3 | EVQLLESGGG LVQPGGSLRL SCAASGFTFS SYAMSWVRQA PGKGLEWVSA ISGSGGSTYY ADSVKGRFTI SRDNSKNTLY LQMNSLRAED TAVYYCASWG LGSNENWGQG TMVTVSS | Full-length V$_H$ | 195_e11 |
| 4 | EVQLLESGGG LVQPGGSLRL SCAASGFTFS SYAMSWVRQA PGKGLEWVSA ISGSGGSTYY ADSVKGRFTI SRDNSKNTLY LQMNSLRAED TAVYYCADTN SAKFDPWGQG TMVTVSS | Full-length V$_H$ | 194_g09, 196_h02 |
| 5 | EVQLLESGGG LVQPGGSLRL SCAASGFTFS SYAMSWVRQA PGKGLEWVSA ISGSGGSTYY ADSVKGRFTI SRDNSKNTLY LQMNSLRAED TAVYYCAGTG YPSFDPWGQG TMVTVSS | Full-length V$_H$ | 194_e01 |
| 6 | EVQLLESGGG LVQPGGSLRL SCAASGFTFS SYAMSWVRQA PGKGLEWVSA ISGSGGSTYY ADSVKGRFTI SRDNSKNTLY LQMNSLRAED TAVYYCAGTA KPSFDPWGQG TMVTVSS | Full-length V$_H$ | 196_d10 |
| 7 | EVQLLESGGG LVQPGGSLRL SCAASGFTFS SYAMSWVRQA PGKGLEWVSA ISGSGGSTYY ADSVKGRFTI SRDNSKNTLY LQMNSLRAED TAVYYCAGNE RPSFDPWGQG TMVTVSS | Full-length V$_H$ | 196_g03 |
| 8 | EVQLLESGGG LVQPGGSLRL SCAASGFTFS SYAMSWVRQA PGKGLEWVSA ISGSGGSTYY ADSVKGRFAI SRDNSKNTLY LQMNSLRAED TAVYYCAGSR TVQFDPWGQG TMVTVSS | Full-length V$_H$ | 196_e06 |
| 9 | EVQLLESGGG LVQPGGSLRL SCAASGFTFS SYAMSWVRQA PGKGLEWVSA ISGSGGSTYY ADSVKGRFTI SRDNSKNTLY LQMNSLRAED TAVYYCATNS PGTFDPWGQG TMVTVSS | Full-length V$_H$ | 195_a09 |

Figure 1A

| | | | |
|---|---|---|---|
| 10 | EVQLLESGGG LVQPGGSLRL SCAASGFTFS SYAMSWVRQA PGKGLEWVSA ISGSGGSTYY ADSVKGRFTI SRDNSKNTLY LQMNSLRAED TAVYYCATIA PGRFDPWGQG TMVTVSS | Full-length V$_H$ | 198_a09 |
| 11 | EVQLLESGGG LVQPGGSLRL SCAASGFTFS SYAMSWVRQA PGKGLEWVSA ISGSGGSTYY ADSVKGRFTI SRDNSKNTLY LQMNSLRAED TAVYYCAGLD RVNFDPWGQG TMVTVSS | Full-length V$_H$ | 200_h06 |
| 12 | EVQLLESGGG LVQPGGSLRL SCAASGFTFS SYAMSWVRQA PGKGLEWVSA ISGSGGSTYY ADSVKGRFTI SRDNSKNTLY LQMNSLRAED TAVYYCASWG GGWFDPWGQG TMVTVSS | Full-length V$_H$ | 129_1c4 |
| 13 | EVQLLESGGG LVQPGGSLRL SCAASGFTFS SYAMSWVRQA PGKGLEWVSA ISGSGGSTYY ADSVKGRFTI SRDNSKNTLY LQMNSLRAED TAVYYCAKWG GGWFDPWGQG TMVTVSS | Full-length V$_H$ - germlined | g_129_1c4 |
| 14 | QSALTQPASV SGSPGQSITI SCTGTSNDVG AYNYVSWYQQ HPGKAPKLIL SEVNKRPSGV SNRFSGSKSG NTASLSISGL QAEDEADYYC SSFTSGLPWV LFGGTKLTV L | Full-length V$_L$ | 194_a02, 194_e06, 196_a07, 198_f06 |
| 15 | QSALTQPASV SGSPGQSITI SCTGTSNDVG AYNYVSWYQQ HPGKAPKLIL SEVNKRPSGV SNRFSGSKSG NTASLSISGL QAEDEADYYC SSFTSGLPWV VFGGTKLTV L | Full-length V$_L$ | 194_b09 |
| 16 | QSALTQPASV SGSPGQSITI SCTGTSNDVG AYNYVSWYQQ HPGKAPKLIL SEVNKRPSGV SNRFSGSKSG NTASLSISGL QAEDEADYYC SSFTSGIVFN LFGGTKLTV L | Full-length V$_L$ | 195_e11 |
| 17 | QSALTQPASV SGSPGQSITI SCTGTSNDVG AYNYVSWYQR HPGKAPKLIL SEVNKRPSGV SNRFSGSKSG NTASLSISGL QAEDEAEYYC SSYTMGSTFM LFGGTKLTV L | Full-length V$_L$ | 194_g09 |
| 18 | QSALTQPASV SGSPGQSITI SCTGTSNDVG AYNYVSWYQQ HPGKAPKLIL SEVNKRPSGV SNRFSGSKSG NTASLSISGL QAEDEAGYYC TSYRAGSTFM LFGGTKLTV L | Full-length V$_L$ | 194_e01 |
| 19 | QSALTQPASV SGPPGQSITI SCTGTSNDVG AYNYVSWYQQ HPGKAPKLIL SEVNKRPSGV SNRFSGSKSG NTASLSISGL QAEDEADYYC TSYTMGSTFM LFGGTKLTV L | Full-length V$_L$ | 198_a09 |

Figure 1B

| | | | |
|---|---|---|---|
| 20 | QSALTQPASV SGSPGQSITI SCTGTSNDVG AYNYVSWYQQ HPGKAPKLIL SEVNKRPSGV SNRFSGSKSG NTASLSISGL QAEDEADYYC TSYRMDSTFM LFGGGTKLTV L | Full-length $V_L$ | 200_h06 |
| 21 | QSALTQPASV SGSPGQSITI SCTGTSNDVG AYNYVSWYQQ HPGKAPKLIL SEVNKRPSGV SNRFSGSKSG NTASLSISGL QAEDEADYYC SSFTSGSTFM LFGGGTKLTV L | Full-length $V_L$ | 129_1c4 |
| 22 | QSALTQPASV SGSPGQSITI SCTGTSNDVG AYNYVSWYQQ HPGKAPKLMI YEVNKRPSGV SNRFSGSKSG NTASLTISGL QAEDEADYYC SSFTSGSTFM LFGGGTKLTV L | Full-length $V_L$ | g_129_1c4 |
| 23 | QSALTQPASV SGSPGQSITI SCTGTSNDVG AYNYVSWYQQ HPGKAPKLIL SEVNKRPSGV SNRFSGSKSG NTASLSISGL QAEDEADYYC TSYTMGSTFM LFGGGTKLTV L | Full-length $V_L$ | 196_h02, 196_d10, 196_g03, 196_e06, 195_a09 |
| 24 | SYAMS | $V_H$ CDR1 | All |
| 25 | AISGSGGSTYYADSVKG | $V_H$ CDR2 | All |
| 26 | WGFGTLWP | $V_H$ CDR3 | 194_e06, 196_a07, 198_f06 |
| 27 | WGDGTLNP | $V_H$ CDR3 | 194_a02, 194_b09 |
| 28 | WGLGSNEN | $V_H$ CDR3 | 195_e11 |
| 29 | TNSAKFDP | $V_H$ CDR3 | 194_g09, 196_h02 |
| 30 | TGYPSFDP | $V_H$ CDR3 | 194_e01 |
| 31 | TAKPSFDP | $V_H$ CDR3 | 196_d10 |
| 32 | NERPSFDP | $V_H$ CDR3 | 196_g03 |
| 33 | SRTVQFDP | $V_H$ CDR3 | 196_e06 |
| 34 | NSPGTFDP | $V_H$ CDR3 | 195_a09 |

Figure 1C

| 35 | IAPGRFDP | V_H CDR3 | 198_a09 |
|---|---|---|---|
| 36 | LDRVWFDP | V_H CDR3 | 200_h06 |
| 37 | WGGGWFDP | V_H CDR3 | 129_1c4, g_129_1c4 |
| 38 | TGTSNDVGAYNYVS | V_L CDR1 | All |
| 39 | EVNKRPS | V_L CDR2 | All |
| 40 | SSFTSGLPWVL | V_L CDR3 | 194_a02, 194_e06, 196_a07, 198_f06 |
| 41 | SSFTSGLPWVV | V_L CDR3 | 194_b09 |
| 42 | SSFTSGIVFNL | V_L CDR3 | 195_e11 |
| 43 | TSYTMGSTFML | V_L CDR3 | 195_a09, 196_d10, 196_e06, 196_g03, 196_h02, 198_a09 |
| 44 | SSYTMGSTFML | V_L CDR3 | 194_g09 |
| 45 | TSYRMDSTFML | V_L CDR3 | 200_h06 |
| 46 | TSYRAGSTFML | V_L CDR3 | 194_e01 |
| 47 | SSFTSGSTFML | V_L CDR3 | 129_1c4, g_129_1c4 |
| 48 | EVQLLESGGGLVQPGGSLRLSCAASGFTFS | V_H FR1 | All |
| 49 | WVRQAPGKGLEWVS | V_H FR2 | All |
| 50 | RFTISRDNSKNTLYLQMNSLRAEDTAVYYCAS | V_H FR3 | 194_e06, 196_a07, 198_f06, 194_a02, 194_b09, 195_e11, 129_1c4 |

Figure 1D

| | | | |
|---|---|---|---|
| 51 | RFTISRDNSKNTLYLQMNSLRAEDTAVYYCAD | V_H FR3 | 194_g09, 196_h02 |
| 52 | RFTISRDNSKNTLYLQMNSLRAEDTAVYYCAG | V_H FR3 | 194_e01, 196_d10, 196_g03, 200_h06 |
| 53 | RFAISRDNSKNTLYLQMNSLRAEDTAVYYCAG | V_H FR3 | 196_e06 |
| 54 | RFTISRDNSKNTLYLQMNSLRAEDTAVYYCAT | V_H FR3 | 195_a09, 198_a09 |
| 55 | RFTISRDNSKNTLYLQMNSLRAEDTAVYYCAK | V_H FR3 | g_129_1c4 |
| 56 | WGQGKMVTVSS | V_H FR4 | 194_e06, 196_a07, 198_f06, 194_a02, 194_b09 |
| 57 | WGQGTMVTVSS | V_H FR4 | 195_e11, 194_g09, 196_h02, 194_e01, 196_d10, 196_g03, 196_e06, 195_a09, 198_a09, 200_h06, 129_1c4, g_129_1c4 |
| 58 | QSALTQPASVSGPPGQSITISC | V_L FR1 | 198_a09 |
| 59 | QSALTQPASVSGSPGQSITISC | V_L FR1 | All – except 198_a09 |
| 60 | WYQRHPGKAPKLILS | V_L FR2 | 194_g09 |
| 61 | WYQQHPGKAPKLMIY | V_L FR2 | g_129_1c4 |

Figure 1E

| 62 | WYQQHPGKAPKLLIS | V_L FR2 | 194_a02, 194_e06, 196_a07, 198_f06, 194_b09, 195_e11, 195_a09, 196_d10, 196_e06, 196_g03, 196_h02, 198_a09, 200_h06, 194_e01, 129_1c4 |
|---|---|---|---|
| 63 | GVSNRFSGSKSGNTASLSISGLQAEDEAEYYC | V_L FR3 | 194_g09 |
| 64 | GVSNRFSGSKSGNTASLSISGLQAEDEAGYYC | V_L FR3 | 194_e01 |
| 65 | GVSNRFSGSKSGNTASLTISGLQAEDEADYYC | V_L FR3 | g_129_1c4 |
| 66 | GVSNRFSGSKSGNTASLSISGLQAEDEADYYC | V_L FR3 | 194_a02, 194_e06, 196_a07, 198_f06, 194_b09, 195_e11, 195_a09, 196_d10, 196_e06, 196_g03, 196_h02, 198_a09, 200_h06, 129_1c4 |
| 67 | FGGGTKLTVL | V_L FR4 | All |
| 68 | GAGGTCCAGCTGTTGGAGTCTGGGGGAGGCTTGGTACAGCCTGGGGGGTC CCTGAGACTCTCCTGTGCAGCCTCTGGATTCACCTTAGCAGCTATGCCA TCACCTGCCCTCCCCACCCTCCCGAACCCTCCAGTCCTCTCTCACCT ATTAGTGGTAGTGGTGGTAGCACATACTACGCAGACTCCGTGAAGGGCCG GTTCACCATCTCCAGAGACAATTCCAAGAACACGCTGTATCTGCAAATGA ACAGCCTGAGAGCCGAGGACACGGCCGTGTATTACTGTGCCAGTTGGGA ACGGGGACCTTGTGCCCTGGGCCCAGGGAAAATGGTCACCGTCTCGAG T | Full-length V_H DNA | 194_e06, 196_a07, 198_f06 |

Figure 1F

| 69 | GAGGTGCAGCTGTTGGAGTCTGGGGGAGGCTTGGTACAGCCTGGGGGTC<br>CCTGAGACTCTCCTGTGCAGCCTCTGGATTCACCTTTAGCAGCTATGCCA<br>TGAGCTGGGTCCGCCAGGCTCCAGGGAAGGGCTGGAGTGGGTCTCAGCT<br>ATTAGTGGTAGTGGTAGCACATACTACCAGACTCCGTGAAGGCCG<br>GTTCACCATCTCCAGAGACAATTCCAAGAACACGCTGTATCTGCAAATGA<br>ACAGCCTGAGAGCCGAGGACACGGCCGTGTATTACTGTGCGAGTTGGGA<br>GACGGGACCCTTGAACCCGTGGGGCCAAGGNAAAATGGTCACCGTCNAG<br>T | Full-length V$_H$ DNA | 194_a02, 194_b09 |
|---|---|---|---|
| 70 | GAGGTGCAGCTGTTGGAGTCTCGGGGGAGGCTTGGTACAGCCTGGGGGTC<br>CCTGAGACTCTCCTGTGCCGCCAGCCTCTGGATTCACCTTTAGCAGCTATGCCA<br>TGAGCTGGGTCCGCCAGGCTCCAGGGAAGGGCTGGAGTGGGTCTCAGCT<br>ATTAGTGGTAGTGGTAGCACAATTCCAGACATACTACCAGACTCCGTGAAGGCCG<br>GTTCACCATCTCCAGAGACAATTCCAAGAACACGCTGTATCTGCAAATGA<br>ACAGCCTGAGAGCCGAGGACACGGCCGTGTATTACTGTGCGAGTTGGGA<br>CTGGGGAGCAACGAAAACTGGGGCCAACAATGGTCACCGTCTCGAG<br>T | Full-length V$_H$ DNA | 195_e11 |
| 71 | GAGGTGCAGCTGTTGGAGTCTCGGGGGAGGCTTGGTACAGCCTGGGGGTC<br>CCTGAGACTCTCCTGTGCAGCCTCTGGATTCACCTTTAGCAGCTATGCCA<br>TGAGCTGGGTCCGCCAGGCTCCAGGGAAGGGCTGGAGTGGGTCTCAGCT<br>ATTAGTGGTAGTGGTAGCACATACTACCAGACTCCGTGAAGGCCG<br>GTTCACCATCTCCAGAGACAATTCCAAGAACACGCTGTATCTGCAAATGA<br>ACAGCCTGAGAGCCGAGGACACGGCCGTGTATTACTGTCCGGACGAAC<br>TCCGCCAAGTTCGACCCCGTGGGGCCAAGGGACAATGGTCACCGTCTCGAG<br>T | Full-length V$_H$ DNA | 194_g09, 196_h02 |

Figure 1G

| 72 | GAGGTGCAGCTGTTGGAGTCTGGGGGAGGCTTGGTACAGCCTGGGGGTC<br>CCTGAGACTCTCCTGTGCAGCCTCTGGATTCACCTTTAGCAGCTATGCCA<br>TGAGCTGGGTCCGCCAGGCTCCAGGGAAGGGGCTGGAGTGGGTCTCAGCT<br>ATTAGTGGTAGTGGTGGTAGCACATACTACGCAGACTCCGTGAAGGGCCG<br>GTTCACCATCTCCAGAGACAATTCCAAGAACACGCTGTATCTGCAAATGA<br>ACAGCCTGAGAGCCGAGGACACGGCCGTGTATTACTGTGCGGGCACGGGG<br>TACCCCTCCTTCGACCCCTGGGGCCAAGGGACAATGGTCACCGTCTCGAG<br>T | Full-length $V_H$ DNA | 194_e01 |
| 73 | GAGGTGCAGCTGTTGGAGTCTGGGGGAGGCTTGGTACAGCCTGGGGGTC<br>CCTGAGACTCTCCTGTGCAGCCTCTGGATTCACCTTTAGCAGCTATGCCA<br>TGAGCTGGGTCCGCCAGGCTCCAGGGAAGGGGCTGGAGTGGGTCTCAGCT<br>ATTAGTGGTAGTGGTGGTAGCACATACTACGCAGACTCCGTGAAGGGCCG<br>GTTCACCATCTCCAGAGACAATTCCAAGAACACGCTGTATCTGCAAATGA<br>ACAGCCTGAGAGCCGAGGACACGGCCGTGTATTACTGTGCGGGCACGGCC<br>AAGCCGAGCTTCGACCCCTGGGGCCAAGGGACAATGGTCACCGTCTCGAG<br>T | Full-length $V_H$ DNA | 196_d10 |
| 74 | GAGGTGCAGCTGTTGGAGTCTGGGGGAGGCTTGGTACAGCCTGGGGGTC<br>CCTGAGACTCTCCTGTGCAGCCTCTGGATTCACCTTTAGCAGCTATGCCA<br>TGAGCTGGGTCCGCCAGGCTCCAGGGAAGGGGCTGGAGTGGGTCTCAGCT<br>ATTAGTGGTAGTGGTGGTAGCACATACTACGCAGACTCCGTGAAGGGCCG<br>GTTCACCATCTCCAGAGACAATTCCAAGAACACGCCTGTATCTGCGGGAACGAG<br>AGGCCCGTCGTTCGACCCCTGGGGCCAAGGGACAATGGTCACCGTCTCGAG<br>T | Full-length $V_H$ DNA | 196_g03 |
| 75 | GAGGTGCAGCTGTTGGAGTCTGGGGGAGGCTTGGTACAGCCTGGGGGTC<br>CCTGAGACTCTCCTGTGCAGCCTCTGGATTCACCTTTAGCAGCTATGCCA<br>TGAGCTGGGTCCGCCAGGCTCCAGGGAAGGGGCTGGAGTGGGTCTCAGCT<br>ATTAGTGGTAGTGGTGGTAGCACATACTACGCAGACTCCGTGAAGGGCCG<br>GTTCGCCATCTCCAGAGACAATTCCAAGAACACGCTGTATCTGCAAATGA<br>ACAGCCTGAGAGCCGAGGACACGGCCGTGTATTACTGTGCGGCAGCCGC<br>ACGGTGCAGTTCGACCCCTGGGGCCAAGGGACAATGGTCACCGTCTCGAG<br>T | Full-length $V_H$ DNA | 196_e06 |

Figure 1H

| 76 | GAGGTGCAGCTGTTGGAGTCTGGGGGAGGCTTGGTACAGCCTGGGGGTC<br>CCTGAGACTCTCCTGTGCAGCCTCTGGATTCACCCTTAGCAGCTATGCCA<br>TGAGCTGGGTCCGCCAGGCTCCAGGGAAGGGGCTGGAGTGGGTCTCAGCT<br>ATTAGTGGTAGTGGTGGTAGCACATACTACGCAGACTCCGTGAAGGGCCG<br>GTTCACCATCTCCAGAGACCCGAGGACCCGTGTATTACTGTGCGACGACTCG<br>ACAGCCTGAGAGCCGAGGACACGGCCGTGTATTACTGTGCGACGACTCG<br>CCGGGGACGTTCGACCCCTGGGCCCAAGGGACCAATGGTCACCGTCTCGAG<br>T | Full-length V<sub>H</sub> DNA | 195_a09 |
|---|---|---|---|
| 77 | GAGGTGCAGCTGTTGGAGTCTGGGGGAGGCTTGGTACAGCCTGGGGGTC<br>CCTGAGACTCTCCTGTGCAGCCTCTGGATTCACCCTTAGCAGCTATGCCA<br>TGAGCTGGGTCCGCCAGGCTCCAGGGAAGGGGCTGGAGTGGGTCTCAGCT<br>ATTAGTGGTAGTGGTGGTAGCACATACTACGCAGACTCCGTGAAGGGCCG<br>GTTCACCATCTCCAGAGACAATTCCAAGAACACGCTGTATCTGCAAATGA<br>ACAGCCTGAGAGCCGAGGACACGGCCGTGTATTACTGTGCGACCATCGCG<br>CCCGGGACGTTCGACCCCCTGGGGCCAAGGGACCAATGGTCACCGTCTCGAG<br>T | Full-length V<sub>H</sub> DNA | 198_a09 |
| 78 | GAGGTGCAGCTGTTGGAGTCTGGGGGAGGCTTGGTACAGCCTGGGGGTC<br>CCTGAGACTCTCCTGTCCGCCAGGCTCCACCCTTAGCAGCTATCCCA<br>TGAGCTGGGTCCGCCAGGCTCCAGGGAAGGGGCTGGAGTGGGTCTCAGCT<br>ATTAGTGGTAGTGGTGGTAGCACATACTACGCAGACTCCGTGAAGGGCCG<br>GTTCACCATCTCCAGAGACAATTCCAAGAACACGCTGTATCTGCAAATGA<br>ACAGCCTGAGAGCCGAGGACACGGCCGTGTATTACTGTGCGGGGATCGAC<br>CGGGTGTGTTCGACCCCGTCGACCCCCTGGGGCCAAGGGACCAATGGTCACCGTCGAG<br>T | Full-length V<sub>H</sub> DNA | 200_h06 |
| 79 | GAGGTGCAGCTGTTGGAGTCTGGGGGAGGCTTGGTACAGCCTGGGGGTC<br>CCTGAGACTCTCCTGTGCAGCCTCTGCACTTCGGATTCACCCTTAGCAGCTATGCCA<br>TGAGCTGGGTCCGCCAGGCTCCAGGGAAGGGGCTGGAGTGGGTCTCTCAGCT<br>ATTAGTGGTAGTGGTGGTAGCACATACTACGCAGACTCCGTGAAGGGCCG<br>GTTCACCATCTCCAGAGACAATTCCAAGAACACGCTGTATCTGCAAATGA<br>ACAGCCTGAGAGCTGTCGACCCCTGGGGCCGTGTATTACTGTGCGAGTTGGGGA<br>GGAGGCTGGTTCGACCCCGTCGACAATGGTCACCGTCTCCTC<br>A | Full-length V<sub>H</sub> DNA | 129_1c4 |

Figure 1I

| 80 | GAGGTGCAGCTGTTGGAGTCTGGGGGAGGCTTGGTACAGCCTGGGGGGTC
CCTGAGACTCTCCTGTGCAGCCTCTGGATTCACCTTTAGCAGCTATGCCA
TGAGCTGGGTCCGCCAGGCTCCAGGGAAGGGGCTGGAGTGGGTCTCAGCT
ATTAGTGGTAGTGGTGGTAGCACATACTACGCAGACTCCGTGAAGGGCCG
GTTCACCATCTCCAGAGACAATTCAAGAACACACTGTATCTGCAAATGA
ACAGCCTGAGAGCCGAGGACACGGCCGTGTATTACTGTGCGAAATGGGGA
GGAGGCTGGTTCGACCCCTGGGGCCAAGGGACAATGGTCACCGTCTCCTC
A | Full-length V$_H$ DNA | g_129_1c4 |
|---|---|---|
| 81 | CAGTCTGCCCTGACTCAGCCTGCCTCCGTGTCTGGGTCTCCTGGACAGTC
GATCACCATCTCCTGCACTGGAACCAGTAATGACGTTGGTGCTTATAATT
ATGTCTCCTGGTACCAACAGCACCCAGGCAAAGCCCCCAAACTCATTCTT
TCTGAGGTCAATAAACGGCCCTCAGGGGTTTCTAATCGCTTCTCTGGCTC
CAAGTCTGCAACACGGCCTCTGAGCATCTCGGGCTCAGGCTGAGG
ACGAGGCTGATTATTACTGCAGCTCATTTACAAGCGGCCTCCCCTGGGTC
CTCTTCGGCGGAGGGACCAAGCTGACCGTCCTA | Full-length V$_L$ DNA | 194_a02, 194_e06, 196_a07, 198_f06 |
| 82 | CAGTCTGCCCTGACTCAGCCTGCCTCCGTGTCTGGGTCTCCTGGACAGTC
GATCACCATCTCCTGCACTGGAACCAGTAATGACGTTGGTGCTTATAATT
ATGTCTCCTGGTACCAAAACGCCCCCAGGCAAAGCCCCCAAACTCATTCTT
TCTGAGGTCAATAAACGGCCCTCAGGGGTTTCTAATCGCTTCTCTGGCTC
CAAGTCTGGCAACACGGCCTCTGAGCATCTCGGGCTCAGGCTGAGG
ACGAGGCTGATTATTACTGCAGCTCATTTACAAGCGGGCTCCCCTGGGTC
GTCTTCGGCGGAGGGACCAAGCTGACCGTCCTA | Full-length V$_L$ DNA | 194_b09 |
| 83 | CAGTCTGCCCTGACTCAGCCTGCCTCCGTGTCTGGGTCTCCTGGACAGTC
GATCACCATCTCCTGCACTGGAACCAGTAATGACGTTGGTGCTTATAATT
ATGTCTCCTGGTACCAACAGCACCCAGGCAAAGCCCCCAAACTCATTCTT
TCTGAGGTCAATAAACGGCCCTCAGGGGTTTCTAATCGCTTCTCTGGCTC
CAAGTCTGGCAACACGGCCTCTGAGCATCTCGGGCTCCAGGCTGAGG
ACGAGGCTGATTATTACTGCAGCTCATTTACAAGCATCGTCGTTCAAC
CTGTTCGGCGGAGGGACCAAGCTGACCGTCCTA | Full-length V$_L$ DNA | 195_e11 |
| 84 | CAGTCTGCCCTGACTCAGCCTGCCTCCGTGTCTGGGTCTCCTGGACAGTC
GATCACCATCTCCTGCACTGGAACCAGTAATGACGTTGGTGCTTATAATT
ATGTCTCCTGGTACCAAAACGCCCCCAGGCAAAGCCCCCAAACTCATTCTT
TCTGAGGTCAATAAACGGCCCTCTCTGAGCATCTCGGGCTCCAGGCTGAGG
CAAGTCTGGCAACACGGCCTCTGAGCATCTCGGGCTCCAGGCTGAGG
ACGAGGCTGAGTATTACTGCAGCACTACACGATGGGGAGCACTTTTATG
CTATTCGGCGGAGGGACCAAGCTGACCGTCCTA | Full-length V$_L$ DNA | 194_g09 |

Figure 1J

| 85 | CAGTCTGCCCTGACTCAGCCTGCCTCCGTGTCTGGGTCTCCTGGACAGTC
GATCACCATCTCCTGCACTGGAACCAGTAATGACGTTGGTGCTTATAATT
ATGTCTCCTGGTACCAACAAACGGCCCCTCAGGGGTTTCTAATCGCTTCTGGCTC
CAAGTCTGAGGTCTGGAGTCCAGGCATCTCTGAGCATCGCTTCTCTGGCTC
ACGAGGCTGGTTATTACTGCACCAGCAGCCGGGCGGGAGCACTTTTATG
CTATTCGGCGAGGGACCAAGCTGACCGTCCTA | Full-length V_L DNA | 194_e01 |
| 86 | CAGTCTGCCCTGACTCAGCCTGCCTCCGTGTCTGGGCCTCCTGGACAGTC
GATCACCATCTCCTGCACTGGAACCAGTAATGACGTTGGTGCTTATAATT
ATGTCTCCTGGTACCAACAAACACCCAGGCAAAGCCCCCAAACTCATTCTT
TCTGAGGTCAATAAACGGCCCCTCAGGGGTTTCTAATCGCTTCTCTGGCTC
CAAGTCTGCAACACGGCCTCTCTGAGCATCTCTGGGCTCCAGGCTGAGG
ACGAGGCTGATTATTACTGCACCTCGTACACCATGGCAGCACTTTTATG
CTATTCGGCGAGGGACCAAGCTGACCGTCCTA | Full-length V_L DNA | 198_a09 |
| 87 | CAGTCTGCCCTGACTCAGCCTGCCTCCGTGTCTGGGTCTCCTGGACAGTC
GATCACCATCTCCTGCACTGGAACCAGTAATGACGTTGGTGCTTATAATT
ATGTCTCCTGGTACCAACAAACACCCAGGCAAAGCCCCCAAACTCATTCTT
TCTGAGGTCAATAAACGGCCCCTCAGGGGTTTCTAATCGCTTCTCTGGCTC
CAAGTCTGCAACACGGCCTCTCTGAGCATCTCTGGGCTCGAGG
ACGAGGCTGATTATTACTGCACCTCGTACCGCATGGACAGCACTTTTATG
CTATTCGGCGAGGGACCAAGCTGACCGTCCTA | Full-length V_L DNA | 200_h06 |
| 88 | CAGTCTGCCCTGACTCAGCCTGCCTCCGTGTCTGGGTCTCCTGGACAGTC
GATCACCATCTCCTGCACTGGAACCAGTAATGACGTTGGTGCTTATAATT
ATGTCTCCTGGTACCAACAAACACCCAGGCAAAGCCCCCAAACTCATTCTT
TCTGAGGTCAATAAACGGCCCCTCAGGGGTTTCTAATCGCTTCTCTGGCTC
CAAGTCTGCAACACGGCCTCTCTGAGCATCTCATTTACAAGCGGGCTGAGG
ACGAGGCTGATTATTACTGCAGCTCATTTACAAGCGGCACTTTTATG
CTATTCGGCGAGGGACCAAGCTGACCGTCCTA | Full-length V_L DNA | 129_1c4 |
| 89 | CAGTCTGCCCTGACTCAGCCTGCCTCCGTGTCTGGGTCTCCTGGACAGTC
GATCACCATCTCCTGCACTGGAACCAGTAATGACGTTGGTGCTTATAATT
ATGTCTCCTGGTACCAACAAACGGCCCCTCAGGGGTTTCTAATCGCTTCTGGCTC
TATGAGGTCAATAAACGGCCCCTCAGGGGTTTCTAATCGCTTCTCTGGCTC
CAAGTCTGCAACACGGCCTCTCTGAGCATCTCTGGGCTCCAGGCTGAGG
ACGAGGCTGATTATTACTGCAGCTCATTTACAAGCGGCACTTTTATG
CTATTCGGCGAGGGACCAAGCTGACCGTCCTA | Full-length V_L DNA | g_129_1c4 |

Figure 1K

| | | | |
|---|---|---|---|
| 90 | CAGTCTGCCCTGACTCAGCCTGCCTCCGTGTCTGGGTCTCCTGGACAGTC GATCACCATCTCCTGCACTGGAACCAGTAATGACGTTGGTGCTTATAATT ATGTCTCCTGGTACCAACAACTCCAGCAAGCCCCCAAACTCATTCTT TCTGAGGTCAATAAACGGCCCTCAGGGGTTTCTAATCGCTTCTCTGGCTC CAAGTCTGCAACACGGCCTCTCTGAGCATCTCTGGGCTCCAGGCTGAGG ACGAGGCTGATTATTACTGCACCTCGTACACCATGGGCAGCACTTTTATG CTATTCGGCGGAGGGACCAAGCTGACCGTCCTA | Full-length V$_L$ DNA | 196_h02, 196_d10, 196_g03, 196_e06, 195_a09 |
| 91 | NPKGQFDP | V$_H$ CDR3 variant | 129-1c4 variant |
| 92 | NSAGSFDP | V$_H$ CDR3 variant | 129-1c4 variant |
| 93 | SNGGLFDP | V$_H$ CDR3 variant | 129-1c4 variant |
| 94 | SNGGFFDP | V$_H$ CDR3 variant | 129-1c4 variant |
| 95 | SDIGRFDP | V$_H$ CDR3 variant | 129-1c4 variant |
| 96 | TNTGQFDP | V$_H$ CDR3 variant | 129-1c4 variant |
| 97 | TPRGLFDP | V$_H$ CDR3 variant | 129-1c4 variant |
| 98 | SNTGNFDP | V$_H$ CDR3 variant | 129-1c4 variant |
| 99 | SRTVQFDP | V$_H$ CDR3 variant | 129-1c4 variant |
| 100 | LGVPQFDP | V$_H$ CDR3 variant | 129-1c4 variant |
| 101 | SDNGTFDP | V$_H$ CDR3 variant | 129-1c4 variant |
| 102 | IAPGRFDP | V$_H$ CDR3 variant | 129-1c4 variant |
| 103 | NTTGTFDP | V$_H$ CDR3 variant | 129-1c4 variant |
| 104 | SDAGRFDP | V$_H$ CDR3 variant | 129-1c4 variant |
| 105 | INEGRFDP | V$_H$ CDR3 variant | 129-1c4 variant |
| 106 | NSNGVFDP | V$_H$ CDR3 variant | 129-1c4 variant |
| 107 | SHSGKFDP | V$_H$ CDR3 variant | 129-1c4 variant |

Figure 1L

| 108 | NKKPFFDP | $V_H$ CDR3 variant | 129-1c4 variant |
| --- | --- | --- | --- |
| 109 | SDNGLFDP | $V_H$ CDR3 variant | 129-1c4 variant |
| 110 | WGAGELDH | $V_H$ CDR3 variant | 129-1c4 variant |
| 111 | WGTGAHEN | $V_H$ CDR3 variant | 129-1c4 variant |
| 112 | NNVGRFDP | $V_H$ CDR3 variant | 129-1c4 variant |
| 113 | TDRPVFDP | $V_H$ CDR3 variant | 129-1c4 variant |
| 114 | IRSGMFDP | $V_H$ CDR3 variant | 129-1c4 variant |
| 115 | TEGALFDP | $V_H$ CDR3 variant | 129-1c4 variant |
| 116 | SDFGKFDP | $V_H$ CDR3 variant | 129-1c4 variant |
| 117 | NELGSFDP | $V_H$ CDR3 variant | 129-1c4 variant |
| 118 | QELPVFDP | $V_H$ CDR3 variant | 129-1c4 variant |
| 119 | FRDTAFDP | $V_H$ CDR3 variant | 129-1c4 variant |
| 120 | ADMGRFDP | $V_H$ CDR3 variant | 129-1c4 variant |
| 121 | LCVPVFDP | $V_H$ CDR3 variant | 129-1c4 variant |
| 122 | THAGMFDP | $V_H$ CDR3 variant | 129-1c4 variant |
| 123 | VYAGRFDP | $V_H$ CDR3 variant | 129-1c4 variant |
| 124 | NTQGRFDP | $V_H$ CDR3 variant | 129-1c4 variant |
| 125 | TNGGLFDP | $V_H$ CDR3 variant | 129-1c4 variant |
| 126 | ITTVKFDP | $V_H$ CDR3 variant | 129-1c4 variant |
| 127 | RLVHGFDP | $V_H$ CDR3 variant | 129-1c4 variant |
| 128 | IRLGTFDP | $V_H$ CDR3 variant | 129-1c4 variant |
| 129 | SERPQFDP | $V_H$ CDR3 variant | 129-1c4 variant |

Figure 1M

| | | | |
|---|---|---|---|
| 130 | TSRPLFDP | V$_H$ CDR3 variant | 129-1c4 variant |
| 131 | VESGRFDP | V$_H$ CDR3 variant | 129-1c4 variant |
| 132 | SEMPMFDP | V$_H$ CDR3 variant | 129-1c4 variant |
| 133 | VNPGYFDP | V$_H$ CDR3 variant | 129-1c4 variant |
| 134 | NDIARFDP | V$_H$ CDR3 variant | 129-1c4 variant |
| 135 | VGVGQFDP | V$_H$ CDR3 variant | 129-1c4 variant |
| 136 | TRYPTFDP | V$_H$ CDR3 variant | 129-1c4 variant |
| 137 | NSAGTFDP | V$_H$ CDR3 variant | 129-1c4 variant |
| 138 | VNEGRFDP | V$_H$ CDR3 variant | 129-1c4 variant |
| 139 | NRTGRFDP | V$_H$ CDR3 variant | 129-1c4 variant |
| 140 | NASARFDP | V$_H$ CDR3 variant | 129-1c4 variant |
| 141 | INTGMFDP | V$_H$ CDR3 variant | 129-1c4 variant |
| 142 | NDNGRFDP | V$_H$ CDR3 variant | 129-1c4 variant |
| 143 | VDQPSFDP | V$_H$ CDR3 variant | 129-1c4 variant |
| 144 | VDRGQFDP | V$_H$ CDR3 variant | 129-1c4 variant |
| 145 | NHTGKFDP | V$_H$ CDR3 variant | 129-1c4 variant |
| 146 | TNTGRFDP | V$_H$ CDR3 variant | 129-1c4 variant |
| 147 | SDSGLFDP | V$_H$ CDR3 variant | 129-1c4 variant |
| 148 | NVLALFDP | V$_H$ CDR3 variant | 129-1c4 variant |
| 149 | NYEARFDP | V$_H$ CDR3 variant | 129-1c4 variant |
| 150 | PDNGTFDP | V$_H$ CDR3 variant | 129-1c4 variant |
| 151 | NRNGNFDP | V$_H$ CDR3 variant | 129-1c4 variant |

Figure 1N

| 152 | TTGGRFDP | V_H CDR3 variant | 129-1c4 variant |
|---|---|---|---|
| 153 | TGYPSFDP | V_H CDR3 variant | 129-1c4 variant |
| 154 | NNEGQFDP | V_H CDR3 variant | 129-1c4 variant |
| 155 | NSKGRFDP | V_H CDR3 variant | 129-1c4 variant |
| 156 | TENPTFDP | V_H CDR3 variant | 129-1c4 variant |
| 157 | TNGGRFDP | V_H CDR3 variant | 129-1c4 variant |
| 158 | NSYGSFDP | V_H CDR3 variant | 129-1c4 variant |
| 159 | LENVVFDP | V_H CDR3 variant | 129-1c4 variant |
| 160 | ANHGRFDP | V_H CDR3 variant | 129-1c4 variant |
| 161 | ANGGQFDP | V_H CDR3 variant | 129-1c4 variant |
| 162 | WGNDASLG | V_H CDR3 variant | 129-1c4 variant |
| 163 | WGPTASLD | V_H CDR3 variant | 129-1c4 variant |
| 164 | WGRGTNEY | V_H CDR3 variant | 129-1c4 variant |
| 165 | WGGGGHYD | V_H CDR3 variant | 129-1c4 variant |
| 166 | WGADATLD | V_H CDR3 variant | 129-1c4 variant |
| 167 | TEFGTFDP | V_H CDR3 variant | 129-1c4 variant |
| 168 | NATGTFDP | V_H CDR3 variant | 129-1c4 variant |
| 169 | TNSAKFDP | V_H CDR3 variant | 129-1c4 variant |
| 170 | VNSGKFDP | V_H CDR3 variant | 129-1c4 variant |
| 171 | SLRVEFDP | V_H CDR3 variant | 129-1c4 variant |
| 172 | NDRGMFDP | V_H CDR3 variant | 129-1c4 variant |
| 173 | NSPGTFDP | V_H CDR3 variant | 129-1c4 variant |

Figure 10

| 174 | NTAGRFDP | V_H CDR3 variant | 129-1c4 variant |
| 175 | VNRGRFDP | V_H CDR3 variant | 129-1c4 variant |
| 176 | TEKPMFDP | V_H CDR3 variant | 129-1c4 variant |
| 177 | WSVSLFDP | V_H CDR3 variant | 129-1c4 variant |
| 178 | MEVVEFDP | V_H CDR3 variant | 129-1c4 variant |
| 179 | VNHGRFDP | V_H CDR3 variant | 129-1c4 variant |
| 180 | TEVGTFDP | V_H CDR3 variant | 129-1c4 variant |
| 181 | TDKPVFDP | V_H CDR3 variant | 129-1c4 variant |
| 182 | LELPRFDP | V_H CDR3 variant | 129-1c4 variant |
| 183 | TNHAMFDP | V_H CDR3 variant | 129-1c4 variant |
| 184 | THSGRFDP | V_H CDR3 variant | 129-1c4 variant |
| 185 | NDRGGFDP | V_H CDR3 variant | 129-1c4 variant |
| 186 | PHRGTFDP | V_H CDR3 variant | 129-1c4 variant |
| 187 | TELGQFDP | V_H CDR3 variant | 129-1c4 variant |
| 188 | WGLGSNEN | V_H CDR3 variant | 129-1c4 variant |
| 189 | WCNDATWN | V_H CDR3 variant | 129-1c4 variant |
| 190 | WGSTASLD | V_H CDR3 variant | 129-1c4 variant |
| 191 | WGGGGHQD | V_H CDR3 variant | 129-1c4 variant |
| 192 | WGRGDWRS | V_H CDR3 variant | 129-1c4 variant |
| 193 | WGSTASLS | V_H CDR3 variant | 129-1c4 variant |
| 194 | WGHGGHDT | V_H CDR3 variant | 129-1c4 variant |
| 195 | WGPRATLD | V_H CDR3 variant | 129-1c4 variant |

Figure 1P

| | | | |
|---|---|---|---|
| 196 | WGNGAFVP | V_H CDR3 variant | 129-1c4 variant |
| 197 | WGNDATLA | V_H CDR3 variant | 129-1c4 variant |
| 198 | WGSGNLDP | V_H CDR3 variant | 129-1c4 variant |
| 199 | NELPKFDP | V_H CDR3 variant | 129-1c4 variant |
| 200 | SDGGTFDP | V_H CDR3 variant | 129-1c4 variant |
| 201 | LDMVMFDP | V_H CDR3 variant | 129-1c4 variant |
| 202 | WGSGTMDP | V_H CDR3 variant | 129-1c4 variant |
| 203 | PDRGKFDP | V_H CDR3 variant | 129-1c4 variant |
| 204 | THNPVFDP | V_H CDR3 variant | 129-1c4 variant |
| 205 | NSAGRFDP | V_H CDR3 variant | 129-1c4 variant |
| 206 | LDSVVFDP | V_H CDR3 variant | 129-1c4 variant |
| 207 | WGTGQHFN | V_H CDR3 variant | 129-1c4 variant |
| 208 | WGTGHHDP | V_H CDR3 variant | 129-1c4 variant |
| 209 | NFKPSFDP | V_H CDR3 variant | 129-1c4 variant |
| 210 | ANGGRFDP | V_H CDR3 variant | 129-1c4 variant |
| 211 | WGTGHLEP | V_H CDR3 variant | 129-1c4 variant |
| 212 | TGLPRFDP | V_H CDR3 variant | 129-1c4 variant |
| 213 | SNVGKFDP | V_H CDR3 variant | 129-1c4 variant |
| 214 | NAVARFDP | V_H CDR3 variant | 129-1c4 variant |
| 215 | TDRPQFDP | V_H CDR3 variant | 129-1c4 variant |
| 216 | SLTVDFDP | V_H CDR3 variant | 129-1c4 variant |
| 217 | TEMAQFDP | V_H CDR3 variant | 129-1c4 variant |

Figure 1Q

| | | | |
|---|---|---|---|
| 218 | WGEGHLEY | V_H CDR3 variant | 129-1c4 variant |
| 219 | QKKVEFDP | V_H CDR3 variant | 129-1c4 variant |
| 220 | TGYPVFNP | V_H CDR3 variant | 129-1c4 variant |
| 221 | ANSAKFDP | V_H CDR3 variant | 129-1c4 variant |
| 222 | VGRPQFDP | V_H CDR3 variant | 129-1c4 variant |
| 223 | TYNPMFDP | V_H CDR3 variant | 129-1c4 variant |
| 224 | TERPVFDP | V_H CDR3 variant | 129-1c4 variant |
| 225 | LDLPRFDP | V_H CDR3 variant | 129-1c4 variant |
| 226 | WGSCSIDH | V_H CDR3 variant | 129-1c4 variant |
| 227 | LDRVCSRW | V_H CDR3 variant | 129-1c4 variant |
| 228 | NTLPVFDP | V_H CDR3 variant | 129-1c4 variant |
| 229 | TKPGRFDP | V_H CDR3 variant | 129-1c4 variant |
| 230 | TGYPVFDP | V_H CDR3 variant | 129-1c4 variant |
| 231 | IKPGMFDP | V_H CDR3 variant | 129-1c4 variant |
| 232 | NMTPRFDP | V_H CDR3 variant | 129-1c4 variant |
| 233 | TERPSFDP | V_H CDR3 variant | 129-1c4 variant |
| 234 | TNYGTFDP | V_H CDR3 variant | 129-1c4 variant |
| 235 | TSRPSFDP | V_H CDR3 variant | 129-1c4 variant |
| 236 | TYWPAFDP | V_H CDR3 variant | 129-1c4 variant |
| 237 | IDMPWFDP | V_H CDR3 variant | 129-1c4 variant |
| 238 | WGTGHHDP | V_H CDR3 variant | 129-1c4 variant |
| 239 | NARPSFDP | V_H CDR3 variant | 129-1c4 variant |

Figure 1R

| | | | |
|---|---|---|---|
| 240 | NCIVHFDP | $V_H$ CDR3 variant | 129-1c4 variant |
| 241 | NVMGRFDP | $V_H$ CDR3 variant | 129-1c4 variant |
| 242 | TDTPVFDP | $V_H$ CDR3 variant | 129-1c4 variant |
| 243 | NRTVWFDP | $V_H$ CDR3 variant | 129-1c4 variant |
| 244 | NRMGSFDP | $V_H$ CDR3 variant | 129-1c4 variant |
| 245 | VKPGFFDP | $V_H$ CDR3 variant | 129-1c4 variant |
| 246 | IDCGRFDP | $V_H$ CDR3 variant | 129-1c4 variant |
| 247 | QSLPQFDP | $V_H$ CDR3 variant | 129-1c4 variant |
| 248 | NELGTFDP | $V_H$ CDR3 variant | 129-1c4 variant |
| 249 | QKKVEFDP | $V_H$ CDR3 variant | 129-1c4 variant |
| 250 | IDTPTFDP | $V_H$ CDR3 variant | 129-1c4 variant |
| 251 | WCYDATLE | $V_H$ CDR3 variant | 129-1c4 variant |
| 252 | SDGGKFDP | $V_H$ CDR3 variant | 129-1c4 variant |
| 253 | LDIVRFDP | $V_H$ CDR3 variant | 129-1c4 variant |
| 254 | ANAGLFDP | $V_H$ CDR3 variant | 129-1c4 variant |
| 255 | WCTGSNRD | $V_H$ CDR3 variant | 129-1c4 variant |
| 256 | SETINFDP | $V_H$ CDR3 variant | 129-1c4 variant |
| 257 | GSYTHGSTFML | $V_L$ CDR3 variant | 129-1c4 variant |
| 258 | SSFTSGIPWAV | $V_L$ CDR3 variant | 129-1c4 variant |
| 259 | SSFTSGVPWAM | $V_L$ CDR3 variant | 129-1c4 variant |
| 260 | SSFTSGLQWVV | $V_L$ CDR3 variant | 129-1c4 variant |
| 261 | SSFTSQIPWAL | $V_L$ CDR3 variant | 129-1c4 variant |

Figure 1S

| 262 | SSFTSAEQWVM | V_L CDR3 variant | 129-1c4 variant |
| --- | --- | --- | --- |
| 263 | SSFTSQPQFNL | V_L CDR3 variant | 129-1c4 variant |
| 264 | SSFTSGSTWVL | V_L CDR3 variant | 129-1c4 variant |
| 265 | SSFTSAVPWAI | V_L CDR3 variant | 129-1c4 variant |
| 266 | SSFTSGAVFVL | V_L CDR3 variant | 129-1c4 variant |
| 267 | SSFTSGIVFNL | V_L CDR3 variant | 129-1c4 variant |
| 268 | ASYRDGSTFML | V_L CDR3 variant | 129-1c4 variant |
| 269 | ASFQSGSTFML | V_L CDR3 variant | 129-1c4 variant |
| 270 | ASYQSASTFML | V_L CDR3 variant | 129-1c4 variant |
| 271 | TSYTASSTFML | V_L CDR3 variant | 129-1c4 variant |
| 272 | SAFQQSSTFML | V_L CDR3 variant | 129-1c4 variant |
| 273 | GSYSQQSTFML | V_L CDR3 variant | 129-1c4 variant |
| 274 | GAYSAGSTFML | V_L CDR3 variant | 129-1c4 variant |
| 275 | TSYTQGSTFML | V_L CDR3 variant | 129-1c4 variant |
| 276 | SSFTSGRAFTC | V_L CDR3 variant | 129-1c4 variant |
| 277 | SSFTSGDHWVL | V_L CDR3 variant | 129-1c4 variant |
| 278 | SSFTSRIPWAV | V_L CDR3 variant | 129-1c4 variant |
| 279 | SSFTSGKAWVI | V_L CDR3 variant | 129-1c4 variant |
| 280 | SSFTSAEAWAP | V_L CDR3 variant | 129-1c4 variant |
| 281 | SSFTSGDRFNL | V_L CDR3 variant | 129-1c4 variant |
| 282 | SSFTSYKPHMV | V_L CDR3 variant | 129-1c4 variant |
| 283 | SSFTSGIQFNL | V_L CDR3 variant | 129-1c4 variant |

Figure 1T

| 284 | SSFTSAARFAL | V_L CDR3 variant | 129-1c4 variant |
|---|---|---|---|
| 285 | SSFTSGSRFVL | V_L CDR3 variant | 129-1c4 variant |
| 286 | SSFTSSLPWAL | V_L CDR3 variant | 129-1c4 variant |
| 287 | SSFTSGIKFTL | V_L CDR3 variant | 129-1c4 variant |
| 288 | SSFTSAIPWSL | V_L CDR3 variant | 129-1c4 variant |
| 289 | SSFTSGEQFLL | V_L CDR3 variant | 129-1c4 variant |
| 290 | SSFTSGPRWNL | V_L CDR3 variant | 129-1c4 variant |
| 291 | SSFTSGSTFNL | V_L CDR3 variant | 129-1c4 variant |
| 292 | SSFTSGRRFVL | V_L CDR3 variant | 129-1c4 variant |
| 293 | SSFTSGNVWVL | V_L CDR3 variant | 129-1c4 variant |
| 294 | SSFTSAPAFVV | V_L CDR3 variant | 129-1c4 variant |
| 295 | SSFTSGKTFVL | V_L CDR3 variant | 129-1c4 variant |
| 296 | SSFTSNIPWAI | V_L CDR3 variant | 129-1c4 variant |
| 297 | SSFTSSAHFVL | V_L CDR3 variant | 129-1c4 variant |
| 298 | SSFTSCPVFNI | V_L CDR3 variant | 129-1c4 variant |
| 299 | SSFTSDRAFNL | V_L CDR3 variant | 129-1c4 variant |
| 300 | SSFTSEWLWVL | V_L CDR3 variant | 129-1c4 variant |
| 301 | SSFTSQPRWAP | V_L CDR3 variant | 129-1c4 variant |
| 302 | SSFTSGIRFNL | V_L CDR3 variant | 129-1c4 variant |
| 303 | SSFTSGRAFNL | V_L CDR3 variant | 129-1c4 variant |
| 304 | SSFTSGPVFNL | V_L CDR3 variant | 129-1c4 variant |
| 305 | SSFTSGQWVL | V_L CDR3 variant | 129-1c4 variant |

Figure 1U

| | | | |
|---|---|---|---|
| 306 | SSFTSGIRFNV | V$_L$ CDR3 variant | 129-1c4 variant |
| 307 | SSFTSGVTWLL | V$_L$ CDR3 variant | 129-1c4 variant |
| 308 | SSFTSGRIFNL | V$_L$ CDR3 variant | 129-1c4 variant |
| 309 | SSFTSGIPWIV | V$_L$ CDR3 variant | 129-1c4 variant |
| 310 | TSYTLGSTFML | V$_L$ CDR3 variant | 129-1c4 variant |
| 311 | TSYTHGSTFML | V$_L$ CDR3 variant | 129-1c4 variant |
| 312 | SSFTSGYAWLL | V$_L$ CDR3 variant | 129-1c4 variant |
| 313 | TSYYMGSTFML | V$_L$ CDR3 variant | 129-1c4 variant |
| 314 | SSFTSCSTFTL | V$_L$ CDR3 variant | 129-1c4 variant |
| 315 | TSFTSGSTFML | V$_L$ CDR3 variant | 129-1c4 variant |
| 316 | TSSTLGSTFML | V$_L$ CDR3 variant | 129-1c4 variant |
| 317 | TRYVMGSTFML | V$_L$ CDR3 variant | 129-1c4 variant |
| 318 | TSYREGSTFML | V$_L$ CDR3 variant | 129-1c4 variant |
| 319 | ASYQASSTFML | V$_L$ CDR3 variant | 129-1c4 variant |
| 320 | EVQLLESGGG LVQPGGSLRL SCAASGFTFS SYAMSWVRQA PGKGLEWVSA ISGSGGSTYY ADSVKGRFTI SRDNSKNILY LQMNSLRAED TAVYYCAKWG DGTLNPWGQG TMVTVSS | Full-length V$_H$ - germlined | g-194-b09 |
| 321 | EVQLLESGGG LVQPGGSLRL SCAASGFTFS SYAMSWVRQA PGKGLEWVSA ISGSGGSTYY ADSVKGRFTI SRDNSKNILY LQMNSLRAED TAVYYCAKTN SAKFDPWGQG TMVTVSS | Full-length V$_H$ - germlined | g-194-g09 |
| 322 | EVQLLESGGG LVQPGGSLRL SCAASGFTFS SYAMSWVRQA PGKGLEWVSA ISGSGGSTYY ADSVKGRFTI SRDNSKNILY LQMNSLRAED TAVYYCAKNE RPSFDPWGQG TMVTVSS | Full-length V$_H$ - germlined | g-196-g03 |
| 323 | EVQLLESGGG LVQPGGSLRL SCAASGFTFS SYAMSWVRQA PGKGLEWVSA ISGSGGSTYY ADSVKGRFTI SRDNSKNILY LQMNSLRAED TAVYYCAKTN SAKFDPWGQG TMVTVSS | Full-length V$_H$ - germlined | g-196-h02 |

Figure 1V

| 324 | EVQLLESGGG LVQPGGSLRL SCAASGFTFS SYAMSWVRQA PGKGLEWVSA ISGSGGSTYY ADSVKGRFTI SRDNSKNTLY LQMNSLRAED TAVYYCAKTC YPSFDPWGQG TMVTVSS | Full-length V<sub>H</sub> - germlined | g-194-e01 |
|---|---|---|---|
| 325 | EVQLLESGGG LVQPGGSLRL SCAASGFTFS SYAMSWVRQA PGKGLEWVSA ISGSGGSTYY ADSVKGRFTI SRDNSKNTLY LQMNSLRAED TAVYYCAKWG TGTLWPGQG TMVTVSS | Full-length V<sub>H</sub> - germlined | g-194-e06 |
| 326 | QSALTQPASV SGSPGQSITI SCTGTSNDVG AYNYVSWYQQ HPGKAPKLMI SEVNKRPSGV SNRFSGSKSG NTASLTISGL QAEDEADYYC SSFTSGLPWV VFGGGTKLTV L | Full-length V<sub>L</sub> - germlined | g-194-b09 |
| 327 | QSALTQPASV SGSPGQSITI SCTGTSNDVG AYNYVSWYQQ HPGKAPKLMI SEVNKRPSGV SNRFSGSKSG NTASLTISGL QAEDEADYYC SSYTMGSTFM LFGGGTKLTV L | Full-length V<sub>L</sub> - germlined | g-194-g09 |
| 328 | QSALTQPASV SGSPGQSITI SCTGTSNDVG AYNYVSWYQQ HPGKAPKLMI SEVNKRPSGV SNRFSGSKSG NTASLTISGL QAEDEADYYC TSYTMGSTFM LFGGGTKLTV L | Full-length V<sub>L</sub> - germlined | g-196-g03 |
| 329 | QSALTQPASV SGSPGQSITI SCTGTSNDVG AYNYVSWYQQ HPGKAPKLMI SEVNKRPSGV SNRFSGSKSG NTASLTISGL QAEDEADYYC TSYTMGSTFM LFGGGTKLTV L | Full-length V<sub>L</sub> - germlined | g-196-h02 |
| 330 | QSALTQPASV SGSPGQSITI SCTGTSNDVG AYNYVSWYQQ HPGKAPKLMI SEVNKRPSGV SNRFSGSKSG NTASLTISGL QAEDEADYYC TSYRAGSTFM LFGGGTKLTV L | Full-length V<sub>L</sub> - germlined | g-194-e01 |
| 331 | QSALTQPASV SGSPGQSITI SCTGTSNDVG AYNYVSWYQQ HPGKAPKLMI SEVNKRPSGV SNRFSGSKSG NTASLTISGL QAEDEADYYC SSFTSGLPWV LFGGGTKLTV L | Full-length V<sub>L</sub> - germlined | g-194-e06 |
| 332 | GAGGTCCAGCTGTTGGAGTCTGGGGGAGGCTTGGTACAGCCTGGGGGGTC CCTGAGACTCTCCTGTGCAGCCTCTGGATTCACCTTTAGCAGCTATGCCA TGAGCTGGGTCCGCCAGGCTCCAGGGAAGGGGCTGGAGTGGGTCTCAGCT ATTAGTGGTAGTGGTGGTAGCACATTACGCAGACTCCGTGAAGGGCCG GTTCACCATCTCCAGAGACAATTCCAAGAACACCCTGTATCTGCAAATGA ACAGCCTGAGAGCCGAGGACACGGCCGTGTATTACTGTGCGAAATGGGGA GACGGGACCTTGAACCCCGTGGGGCCAAGGGACAATGGTCACCGTCTCCTC A | Full-length V<sub>H</sub> DNA - germlined | g-194-b09 |

Figure 1W

| 333 | GAGGTGCAGCTGTTGGAGTCTGGGGGAGGCTTGGTACAGCCTGGGGGGTC CCTGAGACTCTCCTGTGCAGCCTCTGGATTCACCTTTAGCAGCTATGCCA TGAGCTGGGTCCGCCAGGCTCCAGGGAAGGGGCTGGAGTGGGTCTCAGCT ATTAGTGGTAGTGGTGGTAGCACATACTACCAGACTCCGTGAAGGGCCG GTTCACCATCTCCAGAGACAATTCCAAGAACACGCTGTATCTGCAAATGA ACAGCCTGAGAGCCGAGGACACGGCTGTATTACTGTGCGAAAACGAAC TCCCCCAAGTTCGACCCCTGGGGCCAAGGGACACCGTCACCGTCTCCTC A | Full-length V$_H$ DNA - germlined | g-194-g09 |
|---|---|---|---|
| 334 | GAGGTGCAGCTGTTGGAGTCTGGGGGAGGCTTGGTACAGCCTGGGGGGTC CCTGAGACTCTCCTGTGCAGCCTCTGGATTCACCTTTAGCAGCTATGCCA TGAGCTGGGTCCGCCAGGCTCCAGGGAAGGGGCTGGAGTGGGTCTCAGCT ATTAGTGGTAGTGGTGGTAGCACATACTACCAGACTCCGTGAAGGGCCG GTTCACCATCTCCAGAGACAATTCCAAGAACACGCTGTATCTGCAAATGA ACAGCCTGAGAGCCGAGGACACGGCTGTATTACTGTGCGAAAAACGAG AGGCCGTCGTTCGACCCCTGGGGCCAAGGGACACCGTCACCGTCTCCTC A | Full-length V$_H$ DNA - germlined | g-196-g03 |
| 335 | CACCTCCACCTCTTCGACTCTCCCCGACCCTTCGTACACCCTCCCCGGTC CCTGAGACTCTCCTGTGCAGCCTCTGGATTCACCTTTAGCAGCTATGCCA TGAGCTGGGTCCGCCAGGCTCCAGGGAAGGGGCTGGAGTGGGTCTCAGCT ATTAGTGGTAGTGGTGGTAGCACATACTACCAGACTCCGTGAAGGGCCG GTTCACCATCTCCAGAGACAATTCCAAGAACACGCTGTATCTGCAAATGA ACAGCCTGAGAGCCGAGGACACGGCTGTATTACTGTGCGAAATGGGA GACGGGACCTTGAACCCCGTGGGGCCAAGGGACACCGTCACCGTCTCCTC A | Full-length V$_H$ DNA - germlined | g-196-h02 |
| 336 | GAGGTGCAGCTGTTGGAGTCTGGGGGAGGCTTGGTACAGCCTGGGGGGTC CCTGAGACTCTCCTGTGCAGCCTCTGGATTCACCTTTAGCAGCTATGCCA TGAGCTGGGTAGTGGTGGTAGCACATACTACCAGACTCCGTGAAGGGCCG GTTCACCATCTCCAGAGACAATTCCAAGAACACGCTGTATCTGCAAATGA ACAGCCTGAGAGCCGAGGACACGGCCGTGTATTACTGTGCGAAAACGGGG TACCCCTCCTTCGACACCCTGGGGCCAAGGGACACCGTCACCGTCTCCTC A | Full-length V$_H$ DNA - germlined | g-194-e01 |

Figure 1X

| 337 | GAGGTGCAGCTGTTGCAGTCTGGGGGAGGCTTGGTACAGCCTGGGGGGTC<br>CCTGAGACTCTCCTGTGCAGCCTCTGGATTCACCTTTAGCAGCTATGCCA<br>TGAGCTGGGTCCGCCAGGCTCCAGGGAAGGGGCTGGAGTGGGTCTCAGCT<br>ATTAGTGGTAGTGGTCGTAGCACATATTACCAGACTCCGTGAAGGGCCG<br>GTTCACCATCTCCAGAGACAATTCCAAGAACACGCTGTATCTGCAAATGA<br>ACAGCCTGAGAGCCGAGGACACGGCCGTGTATTACTGTGCGAAATGGGGA<br>ACGGGGACCTTTGTGCCCTGGCCCTGGGGCAAGGGACAATGTCACCGTCTCCTC<br>A | Full-length V<sub>H</sub> DNA - germlined | g-194-e06 |
|---|---|---|---|
| 338 | CAGTCTGCCCTGACTCAGCCTCGCTCCTGTCTGGGTCTCCTGACAGTC<br>GATCACCATCTCCTGCACTGGAACCAGTAATGACGTTGGTGCTTATAATT<br>ATGTCTCCTGGTACCAACAACACCCAGGCAAAGCCCCAAACTCATGATT<br>TCTGAGGTCAATAAACGGCCCTCAGGGGTTTCTAATCGCTTCTCTGGCTC<br>CAAGTCTGCCAACACGGCCTCTCTGACCATCTCTGGGCTCCAGGCTGAGG<br>ACGAGGCTGATTATTACTGCAGCTCATTTACAAGCCGGCACTTTTATG<br>GTCTTCGGCGGAGGGACCAAGCTGACCGTCCTA | Full-length V<sub>L</sub> DNA - germlined | g-194-b09 |
| 339 | CAGTCTGCCCTGACTCAGCCTCGCTCCTGTCTGGGTCTCCTGACAGTC<br>GATCACCATCTCCTGCACTGGAACCAGTAATGACGTTGGTGCTTATAATT<br>ATGTCTCCTGGTACCAACAACACCCAGGCAAAGCCCCAAACTCATGATT<br>TCTGAGGTCAATAAACGGCCCTCAGGGGTTTCTAATCGCTTCTCTGGCTC<br>CAAGTCTGCCAACACGGCCTCTCTGACCATCTCTGGGCTCCAGGCTGAGG<br>ACGAGGCTGATTATTACTGCAGCAGCTCATACGACGGGAGCACTTTATG<br>CTATTCGGCGGAGGGACCAAGCTGACCGTCCTA | Full-length V<sub>L</sub> DNA - germlined | g-194-g09 |
| 340 | CAGTCTGCCCTGACTCAGCCTCGCTCCTGTCTGGGTCTCCTGACAGTC<br>GATCACCATCTCCTGCACTGGAACCAGTAATGACGTTGGTGCTTATAATT<br>ATGTCTCCTGGTACCAACAACACCCAGGCAAAGCCCCAAACTCATGATT<br>TCTGAGGTCAATAAACGGCCCTCAGGGGTTTCTAATCGCTTCTCTGGCTC<br>CAAGTCTGCCAACACGGCCCTCTGACCATCTCTGGGCTCCAGGCTGAGG<br>ACCAGGCTGATTATTACTGCACCTCGTACACCATGGGCAGCACTTTTATG<br>CTATTCGGCGGAGGGACCAAGCTGACCGTCCTA | Full-length V<sub>L</sub> DNA - germlined | g-196-g03 |
| 341 | CAGTCTGCCCTGACTCAGCCTCGCTCCTGTCTGGGTCTCCTGACAGTC<br>GATCACCATCTCCTGCACTGGAACCAGTAATGGTGCTTATAATT<br>ATGTCTCCTGGTACCAACAACACCCAGGCAAAGCCCCAAACTCATGATT<br>TCTGAGGTCAATAAACGGCCCTCAGGGGTTTCTAATCGCTTCTCTGGCTC<br>CAAGTCTGCCAACACGGCCCTCTGACCATCTCTGGGCTCCAGGCTGAGG<br>ACCAGGCTGATTATTACTGCACCTCGTACACCATGGGCAGCACTTTTATG<br>CTATTCGGCGGAGGGACCAAGCTGACCGTCCTA | Full-length V<sub>L</sub> DNA - germlined | g-196-h02 |

Figure 1Y

| 342 | CAGTCTGCCCTGACTCAGCCTGCCTCCGTGTCTGGGTCTCCTGGACAGTC GATCACCATCTCCTGCACTGGAACCAGTAATGACGTTGGTCTTATAATT ATGTCCTGGTACCAACAACACCAGGCAAAGCCCCCAAACTCATGATT TCTGAGGTCAATAAACGGCCCTCAGGGGTTTCTAATCGCTTCTCTGGCTC CAAGTCTGGCAACACGGCCTCCATCTCTGGGCTCCAGGCTGAGG ACGAGGCTGATTATTACTGCAGCCTGTACACCATGGGCAGCACTTTTATG CTATTCGGCGGAGGGACCAAGCTGACCGTCCTA | Full-length V_L DNA - germlined | g-194-e01 |
| 343 | CAGTCTGCCCTGACTCAGCCTGCCTCCGTGTCTGGGTCTCCTGGACAGTC GATCACCATCTCCTGCACTGGAACCAGTAATGACGTTGGTCTTATAATT ATGTCCTCCTGCTACCAACAACACCAGGCAAAGCCCCAAACTCATGATT TCTGAGGTCAATAAACGGCCCTCAGGGGTTTCTAATCGCTTCTCTGGCTC CAAGTCTGGCAACACGGCCTCTCTGACCATCTCTGGGCTCCAGGCTGAGG ACGAGGCTGATTATTACTGCAGCTCATTTACAAGCGGGTTGCCGTGGGTG CTCTTCGGCGGAGGGACCAAGCTGACCGTCCTA | Full-length V_L DNA - germlined | g-194-e06 |
| 344 | ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCDKTHTCP PCPAPELLGG PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPIEKTIS KAKGQPREPQ VYTLPPSREE MTKNQVSLTC LVKGFYPSDI AVEWESNGQP ENNYKTTPPV LDSDGSFFLY SKLTVDKSRW QQGNVFSCSV MHEALHNHYT QKSLSLSPGK | IgG_1 heavy chain constant region | All |
| 345 | GQPKAAPSVT LFPPSSEELQ ANKATLVCLI SDFYPGAVTV AWKADSSPVK AGVETTTPSK QSNNKYAASS YLSLTPEQWK SHRSYSCQVT HEGSTVEKTV APTECS | IgG_1 light chain constant region | All |
| 346 | MEWSWVFLFF LSVTTGVHS | Heavy chain signal sequence | All |
| 347 | MSVPTQVLGL LLLWLTDARC | Light chain signal sequence | All |

Figure 1Z

SEQUENCE LISTING

<160> NUMBER OF SEQ ID NOS: 347

<210> SEQ ID NO 1
<211> LENGTH: 117
<212> TYPE: PRT
<213> ORGANISM: human

<400> SEQUENCE: 1

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ser Trp Gly Thr Gly Thr Leu Trp Pro Trp Gly Gln Gly Lys Met
                100                 105                 110

Val Thr Val Ser Ser
            115

<210> SEQ ID NO 2
<211> LENGTH: 117
<212> TYPE: PRT
<213> ORGANISM: human

<400> SEQUENCE: 2

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
                 20                  25                  30

Ala Met Ser Trp Val Arg Gln Ala Pro Gly Lys Gly Leu Glu Trp Val
             35                  40                  45

Ser Ala Ile Ser Gly Ser Gly Gly Ser Thr Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ser Trp Gly Asp Gly Thr Leu Asn Pro Trp Gly Gln Gly Lys Met
                100                 105                 110

Val Thr Val Ser Ser
            115

<210> SEQ ID NO 3
<211> LENGTH: 117
<212> TYPE: PRT
<213> ORGANISM: human

<400> SEQUENCE: 3

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
                 20                  25                  30

Ala Met Ser Trp Val Arg Gln Ala Pro Gly Lys Gly Leu Glu Trp Val
             35                  40                  45

Ser Ala Ile Ser Gly Ser Gly Ser Thr Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ser Trp Gly Leu Gly Ser Asn Glu Asn Trp Gly Gln Gly Thr Met
                100                 105                 110

Val Thr Val Ser Ser
            115

<210> SEQ ID NO 4
<211> LENGTH: 117
```

```
<212> TYPE: PRT
<213> ORGANISM: human

<400> SEQUENCE: 4

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Asp Thr Asn Ser Ala Lys Phe Asp Pro Trp Gly Gln Gly Thr Met
            100                 105                 110

Val Thr Val Ser Ser
        115

<210> SEQ ID NO 5
<211> LENGTH: 117
<212> TYPE: PRT
<213> ORGANISM: human

<400> SEQUENCE: 5

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Gly Thr Gly Tyr Pro Ser Phe Asp Pro Trp Gly Gln Gly Thr Met
            100                 105                 110

Val Thr Val Ser Ser
        115

<210> SEQ ID NO 6
<211> LENGTH: 117
<212> TYPE: PRT
<213> ORGANISM: human

<400> SEQUENCE: 6

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
```

```
                50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Gly Thr Ala Lys Pro Ser Phe Asp Pro Trp Gly Gln Gly Thr Met
                100                 105                 110

Val Thr Val Ser Ser
            115

<210> SEQ ID NO 7
<211> LENGTH: 117
<212> TYPE: PRT
<213> ORGANISM: human

<400> SEQUENCE: 7

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                 20                  25                  30

Ala Met Ser Trp Val Arg Gln Ala Pro Gly Lys Gly Leu Glu Trp Val
                 35                  40                  45

Ser Ala Ile Ser Gly Ser Gly Gly Ser Thr Tyr Tyr Ala Asp Ser Val
             50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Gly Asn Glu Arg Pro Ser Phe Asp Pro Trp Gly Gln Gly Thr Met
                100                 105                 110

Val Thr Val Ser Ser
            115

<210> SEQ ID NO 8
<211> LENGTH: 117
<212> TYPE: PRT
<213> ORGANISM: human

<400> SEQUENCE: 8

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                 20                  25                  30

Ala Met Ser Trp Val Arg Gln Ala Pro Gly Lys Gly Leu Glu Trp Val
                 35                  40                  45

Ser Ala Ile Ser Gly Ser Gly Gly Ser Thr Tyr Tyr Ala Asp Ser Val
             50                  55                  60

Lys Gly Arg Phe Ala Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Gly Ser Arg Thr Val Gln Phe Asp Pro Trp Gly Gln Gly Thr Met
                100                 105                 110

Val Thr Val Ser Ser
            115
```

```
<210> SEQ ID NO 9
<211> LENGTH: 117
<212> TYPE: PRT
<213> ORGANISM: human

<400> SEQUENCE: 9

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Asn Ser Pro Gly Thr Phe Asp Pro Trp Gly Gln Gly Thr Met
            100                 105                 110

Val Thr Val Ser Ser
        115

<210> SEQ ID NO 10
<211> LENGTH: 117
<212> TYPE: PRT
<213> ORGANISM: human

<400> SEQUENCE: 10

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Ile Ala Pro Gly Arg Phe Asp Pro Trp Gly Gln Gly Thr Met
            100                 105                 110

Val Thr Val Ser Ser
        115

<210> SEQ ID NO 11
<211> LENGTH: 117
<212> TYPE: PRT
<213> ORGANISM: human

<400> SEQUENCE: 11

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45
```

```
Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Gly Leu Asp Arg Val Trp Phe Asp Pro Trp Gly Gln Gly Thr Met
            100                 105                 110

Val Thr Val Ser Ser
            115

<210> SEQ ID NO 12
<211> LENGTH: 117
<212> TYPE: PRT
<213> ORGANISM: human

<400> SEQUENCE: 12

Glu Val Gln Leu Leu Glu Ser Gly Gly Gly Leu Val Gln Pro Gly Gly
 1                5                  10                  15

Ser Leu Arg Leu Ser Cys Ala Ala Ser Gly Phe Thr Phe Ser Ser Tyr
                 20                  25                  30

Ala Met Ser Trp Val Arg Gln Ala Pro Gly Lys Gly Leu Glu Trp Val
             35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ser Trp Gly Gly Gly Trp Phe Asp Pro Trp Gly Gln Gly Thr Met
            100                 105                 110

Val Thr Val Ser Ser
            115

<210> SEQ ID NO 13
<211> LENGTH: 117
<212> TYPE: PRT
<213> ORGANISM: human

<400> SEQUENCE: 13

Glu Val Gln Leu Leu Glu Ser Gly Gly Gly Leu Val Gln Pro Gly Gly
 1                5                  10                  15

Ser Leu Arg Leu Ser Cys Ala Ala Ser Gly Phe Thr Phe Ser Ser Tyr
                 20                  25                  30

Ala Met Ser Trp Val Arg Gln Ala Pro Gly Lys Gly Leu Glu Trp Val
             35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Trp Gly Gly Gly Trp Phe Asp Pro Trp Gly Gln Gly Thr Met
            100                 105                 110

Val Thr Val Ser Ser
            115
```

<210> SEQ ID NO 14
<211> LENGTH: 111
<212> TYPE: PRT
<213> ORGANISM: human

<400> SEQUENCE: 14

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Asn Asp Val Gly Ala Tyr
            20                  25                  30

Asn Tyr Val Ser Trp Tyr Gln Gln His Pro Gly Lys Ala Pro Lys Leu
        35                  40                  45

Ile Leu Ser Glu Val Asn Lys Arg Pro Ser Gly Val Ser Asn Arg Phe
    50                  55                  60

Ser Gly Ser Lys Ser Gly Asn Thr Ala Ser Leu Ser Ile Ser Gly Leu
65                  70                  75                  80

Gln Ala Glu Asp Glu Ala Asp Tyr Tyr Cys Ser Ser Phe Thr Ser Gly
                85                  90                  95

Leu Pro Trp Val Leu Phe Gly Gly Gly Thr Lys Leu Thr Val Leu
            100                 105                 110

<210> SEQ ID NO 15
<211> LENGTH: 111
<212> TYPE: PRT
<213> ORGANISM: human

<400> SEQUENCE: 15

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Asn Asp Val Gly Ala Tyr
            20                  25                  30

Asn Tyr Val Ser Trp Tyr Gln Gln His Pro Gly Lys Ala Pro Lys Leu
        35                  40                  45

Ile Leu Ser Glu Val Asn Lys Arg Pro Ser Gly Val Ser Asn Arg Phe
    50                  55                  60

Ser Gly Ser Lys Ser Gly Asn Thr Ala Ser Leu Ser Ile Ser Gly Leu
65                  70                  75                  80

Gln Ala Glu Asp Glu Ala Asp Tyr Tyr Cys Ser Ser Phe Thr Ser Gly
                85                  90                  95

Leu Pro Trp Val Val Phe Gly Gly Gly Thr Lys Leu Thr Val Leu
            100                 105                 110

<210> SEQ ID NO 16
<211> LENGTH: 111
<212> TYPE: PRT
<213> ORGANISM: human

<400> SEQUENCE: 16

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Asn Asp Val Gly Ala Tyr
            20                  25                  30

Asn Tyr Val Ser Trp Tyr Gln Gln His Pro Gly Lys Ala Pro Lys Leu
        35                  40                  45

Ile Leu Ser Glu Val Asn Lys Arg Pro Ser Gly Val Ser Asn Arg Phe
    50                  55                  60

```
Ser Gly Ser Lys Ser Gly Asn Thr Ala Ser Leu Ser Ile Ser Gly Leu
 65                  70                  75                  80

Gln Ala Glu Asp Glu Ala Asp Tyr Tyr Cys Ser Ser Phe Thr Ser Gly
                 85                  90                  95

Ile Val Phe Asn Leu Phe Gly Gly Gly Thr Lys Leu Thr Val Leu
            100                 105                 110

<210> SEQ ID NO 17
<211> LENGTH: 111
<212> TYPE: PRT
<213> ORGANISM: human

<400> SEQUENCE: 17

Gln Ser Ala Leu Thr Gln Pro Ala Ser Val Ser Gly Ser Pro Gly Gln
 1               5                  10                  15

Ser Ile Thr Ile Ser Cys Thr Gly Thr Ser Asn Asp Val Gly Ala Tyr
                20                  25                  30

Asn Tyr Val Ser Trp Tyr Gln Arg His Pro Gly Lys Ala Pro Lys Leu
            35                  40                  45

Ile Leu Ser Glu Val Asn Lys Arg Pro Ser Gly Val Ser Asn Arg Phe
 50                  55                  60

Ser Gly Ser Lys Ser Gly Asn Thr Ala Ser Leu Ser Ile Ser Gly Leu
 65                  70                  75                  80

Gln Ala Glu Asp Glu Ala Glu Tyr Tyr Cys Ser Ser Tyr Thr Met Gly
                 85                  90                  95

Ser Thr Phe Met Leu Phe Gly Gly Gly Thr Lys Leu Thr Val Leu
            100                 105                 110

<210> SEQ ID NO 18
<211> LENGTH: 111
<212> TYPE: PRT
<213> ORGANISM: human

<400> SEQUENCE: 18

Gln Ser Ala Leu Thr Gln Pro Ala Ser Val Ser Gly Ser Pro Gly Gln
 1               5                  10                  15

Ser Ile Thr Ile Ser Cys Thr Gly Thr Ser Asn Asp Val Gly Ala Tyr
                20                  25                  30

Asn Tyr Val Ser Trp Tyr Gln Gln His Pro Gly Lys Ala Pro Lys Leu
            35                  40                  45

Ile Leu Ser Glu Val Asn Lys Arg Pro Ser Gly Val Ser Asn Arg Phe
 50                  55                  60

Ser Gly Ser Lys Ser Gly Asn Thr Ala Ser Leu Ser Ile Ser Gly Leu
 65                  70                  75                  80

Gln Ala Glu Asp Glu Ala Gly Tyr Tyr Cys Thr Ser Tyr Arg Ala Gly
                 85                  90                  95

Ser Thr Phe Met Leu Phe Gly Gly Gly Thr Lys Leu Thr Val Leu
            100                 105                 110

<210> SEQ ID NO 19
<211> LENGTH: 111
<212> TYPE: PRT
<213> ORGANISM: human

<400> SEQUENCE: 19

Gln Ser Ala Leu Thr Gln Pro Ala Ser Val Ser Gly Pro Pro Gly Gln
 1               5                  10                  15

Ser Ile Thr Ile Ser Cys Thr Gly Thr Ser Asn Asp Val Gly Ala Tyr
```

```
            20                  25                  30
Asn Tyr Val Ser Trp Tyr Gln Gln His Pro Gly Lys Ala Pro Lys Leu
            35                  40                  45
Ile Leu Ser Glu Val Asn Lys Arg Pro Ser Gly Val Ser Asn Arg Phe
    50                  55                  60
Ser Gly Ser Lys Ser Gly Asn Thr Ala Ser Leu Ser Ile Ser Gly Leu
65                  70                  75                  80
Gln Ala Glu Asp Glu Ala Asp Tyr Tyr Cys Thr Ser Tyr Thr Met Gly
                85                  90                  95
Ser Thr Phe Met Leu Phe Gly Gly Gly Thr Lys Leu Thr Val Leu
            100                 105                 110
```

<210> SEQ ID NO 20
<211> LENGTH: 111
<212> TYPE: PRT
<213> ORGANISM: human

<400> SEQUENCE: 20

```
Gln Ser Ala Leu Thr Gln Pro Ala Ser Val Ser Gly Ser Pro Gly Gln
1               5                   10                  15
Ser Ile Thr Ile Ser Cys Thr Gly Thr Ser Asn Asp Val Gly Ala Tyr
            20                  25                  30
Asn Tyr Val Ser Trp Tyr Gln Gln His Pro Gly Lys Ala Pro Lys Leu
            35                  40                  45
Ile Leu Ser Glu Val Asn Lys Arg Pro Ser Gly Val Ser Asn Arg Phe
    50                  55                  60
Ser Gly Ser Lys Ser Gly Asn Thr Ala Ser Leu Ser Ile Ser Gly Leu
65                  70                  75                  80
Gln Ala Glu Asp Glu Ala Asp Tyr Tyr Cys Thr Ser Tyr Arg Met Asp
                85                  90                  95
Ser Thr Phe Met Leu Phe Gly Gly Gly Thr Lys Leu Thr Val Leu
            100                 105                 110
```

<210> SEQ ID NO 21
<211> LENGTH: 111
<212> TYPE: PRT
<213> ORGANISM: human

<400> SEQUENCE: 21

```
Gln Ser Ala Leu Thr Gln Pro Ala Ser Val Ser Gly Ser Pro Gly Gln
1               5                   10                  15
Ser Ile Thr Ile Ser Cys Thr Gly Thr Ser Asn Asp Val Gly Ala Tyr
            20                  25                  30
Asn Tyr Val Ser Trp Tyr Gln Gln His Pro Gly Lys Ala Pro Lys Leu
            35                  40                  45
Ile Leu Ser Glu Val Asn Lys Arg Pro Ser Gly Val Ser Asn Arg Phe
    50                  55                  60
Ser Gly Ser Lys Ser Gly Asn Thr Ala Ser Leu Ser Ile Ser Gly Leu
65                  70                  75                  80
Gln Ala Glu Asp Glu Ala Asp Tyr Tyr Cys Ser Ser Phe Thr Ser Gly
                85                  90                  95
Ser Thr Phe Met Leu Phe Gly Gly Gly Thr Lys Leu Thr Val Leu
            100                 105                 110
```

<210> SEQ ID NO 22
<211> LENGTH: 111
<212> TYPE: PRT

<213> ORGANISM: human

<400> SEQUENCE: 22

Gln Ser Ala Leu Thr Gln Pro Ala Ser Val Ser Gly Ser Pro Gly Gln
1               5                   10                  15
Ser Ile Thr Ile Ser Cys Thr Gly Thr Ser Asn Asp Val Gly Ala Tyr
            20                  25                  30
Asn Tyr Val Ser Trp Tyr Gln Gln His Pro Gly Lys Ala Pro Lys Leu
        35                  40                  45
Met Ile Tyr Glu Val Asn Lys Arg Pro Ser Gly Val Ser Asn Arg Phe
    50                  55                  60
Ser Gly Ser Lys Ser Gly Asn Thr Ala Ser Leu Thr Ile Ser Gly Leu
65                  70                  75                  80
Gln Ala Glu Asp Glu Ala Asp Tyr Tyr Cys Ser Ser Phe Thr Ser Gly
                85                  90                  95
Ser Thr Phe Met Leu Phe Gly Gly Gly Thr Lys Leu Thr Val Leu
            100                 105                 110

<210> SEQ ID NO 23
<211> LENGTH: 111
<212> TYPE: PRT
<213> ORGANISM: human

<400> SEQUENCE: 23

Gln Ser Ala Leu Thr Gln Pro Ala Ser Val Ser Gly Ser Pro Gly Gln
1               5                   10                  15
Ser Ile Thr Ile Ser Cys Thr Gly Thr Ser Asn Asp Val Gly Ala Tyr
            20                  25                  30
Asn Tyr Val Ser Trp Tyr Gln Gln His Pro Gly Lys Ala Pro Lys Leu
        35                  40                  45
Ile Leu Ser Glu Val Asn Lys Arg Pro Ser Gly Val Ser Asn Arg Phe
    50                  55                  60
Ser Gly Ser Lys Ser Gly Asn Thr Ala Ser Leu Ser Ile Ser Gly Leu
65                  70                  75                  80
Gln Ala Glu Asp Glu Ala Asp Tyr Tyr Cys Thr Ser Tyr Thr Met Gly
                85                  90                  95
Ser Thr Phe Met Leu Phe Gly Gly Gly Thr Lys Leu Thr Val Leu
            100                 105                 110

<210> SEQ ID NO 24
<211> LENGTH: 5
<212> TYPE: PRT
<213> ORGANISM: human

<400> SEQUENCE: 24

Ser Tyr Ala Met Ser
1               5

<210> SEQ ID NO 25
<211> LENGTH: 17
<212> TYPE: PRT
<213> ORGANISM: human

<400> SEQUENCE: 25

Ala Ile Ser Gly Ser Gly Gly Ser Thr Tyr Tyr Ala Asp Ser Val Lys
1               5                   10                  15
Gly

```
<210> SEQ ID NO 26
<211> LENGTH: 8
<212> TYPE: PRT
<213> ORGANISM: human

<400> SEQUENCE: 26

Trp Gly Thr Gly Thr Leu Trp Pro
1               5

<210> SEQ ID NO 27
<211> LENGTH: 8
<212> TYPE: PRT
<213> ORGANISM: human

<400> SEQUENCE: 27

Trp Gly Asp Gly Thr Leu Asn Pro
1               5

<210> SEQ ID NO 28
<211> LENGTH: 8
<212> TYPE: PRT
<213> ORGANISM: human

<400> SEQUENCE: 28

Trp Gly Leu Gly Ser Asn Glu Asn
1               5

<210> SEQ ID NO 29
<211> LENGTH: 8
<212> TYPE: PRT
<213> ORGANISM: human

<400> SEQUENCE: 29

Thr Asn Ser Ala Lys Phe Asp Pro
1               5

<210> SEQ ID NO 30
<211> LENGTH: 8
<212> TYPE: PRT
<213> ORGANISM: human

<400> SEQUENCE: 30

Thr Gly Tyr Pro Ser Phe Asp Pro
1               5

<210> SEQ ID NO 31
<211> LENGTH: 8
<212> TYPE: PRT
<213> ORGANISM: human

<400> SEQUENCE: 31

Thr Ala Lys Pro Ser Phe Asp Pro
1               5

<210> SEQ ID NO 32
<211> LENGTH: 8
<212> TYPE: PRT
<213> ORGANISM: human

<400> SEQUENCE: 32

Asn Glu Arg Pro Ser Phe Asp Pro
1               5

<210> SEQ ID NO 33
<211> LENGTH: 8
```

```
<212> TYPE: PRT
<213> ORGANISM: human

<400> SEQUENCE: 33

Ser Arg Thr Val Gln Phe Asp Pro
1               5

<210> SEQ ID NO 34
<211> LENGTH: 8
<212> TYPE: PRT
<213> ORGANISM: human

<400> SEQUENCE: 34

Asn Ser Pro Gly Thr Phe Asp Pro
1               5

<210> SEQ ID NO 35
<211> LENGTH: 8
<212> TYPE: PRT
<213> ORGANISM: human

<400> SEQUENCE: 35

Ile Ala Pro Gly Arg Phe Asp Pro
1               5

<210> SEQ ID NO 36
<211> LENGTH: 8
<212> TYPE: PRT
<213> ORGANISM: human

<400> SEQUENCE: 36

Leu Asp Arg Val Trp Phe Asp Pro
1               5

<210> SEQ ID NO 37
<211> LENGTH: 8
<212> TYPE: PRT
<213> ORGANISM: human

<400> SEQUENCE: 37

Trp Gly Gly Gly Trp Phe Asp Pro
1               5

<210> SEQ ID NO 38
<211> LENGTH: 14
<212> TYPE: PRT
<213> ORGANISM: human

<400> SEQUENCE: 38

Thr Gly Thr Ser Asn Asp Val Gly Ala Tyr Asn Tyr Val Ser
1               5                   10

<210> SEQ ID NO 39
<211> LENGTH: 7
<212> TYPE: PRT
<213> ORGANISM: human

<400> SEQUENCE: 39

Glu Val Asn Lys Arg Pro Ser
1               5

<210> SEQ ID NO 40
<211> LENGTH: 11
<212> TYPE: PRT
<213> ORGANISM: human
```

<400> SEQUENCE: 40

Ser Ser Phe Thr Ser Gly Leu Pro Trp Val Leu
1               5                   10

<210> SEQ ID NO 41
<211> LENGTH: 11
<212> TYPE: PRT
<213> ORGANISM: human

<400> SEQUENCE: 41

Ser Ser Phe Thr Ser Gly Leu Pro Trp Val Val
1               5                   10

<210> SEQ ID NO 42
<211> LENGTH: 11
<212> TYPE: PRT
<213> ORGANISM: human

<400> SEQUENCE: 42

Ser Ser Phe Thr Ser Gly Ile Val Phe Asn Leu
1               5                   10

<210> SEQ ID NO 43
<211> LENGTH: 11
<212> TYPE: PRT
<213> ORGANISM: human

<400> SEQUENCE: 43

Thr Ser Tyr Thr Met Gly Ser Thr Phe Met Leu
1               5                   10

<210> SEQ ID NO 44
<211> LENGTH: 11
<212> TYPE: PRT
<213> ORGANISM: human

<400> SEQUENCE: 44

Ser Ser Tyr Thr Met Gly Ser Thr Phe Met Leu
1               5                   10

<210> SEQ ID NO 45
<211> LENGTH: 11
<212> TYPE: PRT
<213> ORGANISM: human

<400> SEQUENCE: 45

Thr Ser Tyr Arg Met Asp Ser Thr Phe Met Leu
1               5                   10

<210> SEQ ID NO 46
<211> LENGTH: 11
<212> TYPE: PRT
<213> ORGANISM: human

<400> SEQUENCE: 46

Thr Ser Tyr Arg Ala Gly Ser Thr Phe Met Leu
1               5                   10

<210> SEQ ID NO 47
<211> LENGTH: 11
<212> TYPE: PRT
<213> ORGANISM: human

<400> SEQUENCE: 47

```
Ser Ser Phe Thr Ser Gly Ser Thr Phe Met Leu
1               5                   10
```

<210> SEQ ID NO 48
<211> LENGTH: 30
<212> TYPE: PRT
<213> ORGANISM: human

<400> SEQUENCE: 48

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30
```

<210> SEQ ID NO 49
<211> LENGTH: 14
<212> TYPE: PRT
<213> ORGANISM: human

<400> SEQUENCE: 49

```
Trp Val Arg Gln Ala Pro Gly Lys Gly Leu Glu Trp Val Ser
1               5                   10
```

<210> SEQ ID NO 50
<211> LENGTH: 32
<212> TYPE: PRT
<213> ORGANISM: human

<400> SEQUENCE: 50

```
Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Ser
            20                  25                  30
```

<210> SEQ ID NO 51
<211> LENGTH: 32
<212> TYPE: PRT
<213> ORGANISM: human

<400> SEQUENCE: 51

```
Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Asp
            20                  25                  30
```

<210> SEQ ID NO 52
<211> LENGTH: 32
<212> TYPE: PRT
<213> ORGANISM: human

<400> SEQUENCE: 52

```
Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Gly
            20                  25                  30
```

<210> SEQ ID NO 53
<211> LENGTH: 32
<212> TYPE: PRT
<213> ORGANISM: human

<400> SEQUENCE: 53

```
Arg Phe Ala Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Gly
            20                  25                  30
```

<210> SEQ ID NO 54
<211> LENGTH: 32
<212> TYPE: PRT
<213> ORGANISM: human

<400> SEQUENCE: 54

```
Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Thr
            20                  25                  30
```

<210> SEQ ID NO 55
<211> LENGTH: 32
<212> TYPE: PRT
<213> ORGANISM: human

<400> SEQUENCE: 55

```
Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Lys
            20                  25                  30
```

<210> SEQ ID NO 56
<211> LENGTH: 11
<212> TYPE: PRT
<213> ORGANISM: human

<400> SEQUENCE: 56

```
Trp Gly Gln Gly Lys Met Val Thr Val Ser Ser
1               5                   10
```

<210> SEQ ID NO 57
<211> LENGTH: 11
<212> TYPE: PRT
<213> ORGANISM: human

<400> SEQUENCE: 57

```
Trp Gly Gln Gly Thr Met Val Thr Val Ser Ser
1               5                   10
```

<210> SEQ ID NO 58
<211> LENGTH: 22
<212> TYPE: PRT
<213> ORGANISM: human

<400> SEQUENCE: 58

```
Gln Ser Ala Leu Thr Gln Pro Ala Ser Val Ser Gly Pro Gly Gln
1               5                   10                  15

Ser Ile Thr Ile Ser Cys
            20
```

<210> SEQ ID NO 59
<211> LENGTH: 22
<212> TYPE: PRT
<213> ORGANISM: human

<400> SEQUENCE: 59

```
Gln Ser Ala Leu Thr Gln Pro Ala Ser Val Ser Gly Ser Pro Gly Gln
```

```
                1               5                   10                  15
Ser Ile Thr Ile Ser Cys
                20

<210> SEQ ID NO 60
<211> LENGTH: 15
<212> TYPE: PRT
<213> ORGANISM: human

<400> SEQUENCE: 60

Trp Tyr Gln Arg His Pro Gly Lys Ala Pro Lys Leu Ile Leu Ser
1               5                   10                  15

<210> SEQ ID NO 61
<211> LENGTH: 15
<212> TYPE: PRT
<213> ORGANISM: human

<400> SEQUENCE: 61

Trp Tyr Gln Gln His Pro Gly Lys Ala Pro Lys Leu Met Ile Tyr
1               5                   10                  15

<210> SEQ ID NO 62
<211> LENGTH: 15
<212> TYPE: PRT
<213> ORGANISM: human

<400> SEQUENCE: 62

Trp Tyr Gln Gln His Pro Gly Lys Ala Pro Lys Leu Ile Leu Ser
1               5                   10                  15

<210> SEQ ID NO 63
<211> LENGTH: 32
<212> TYPE: PRT
<213> ORGANISM: human

<400> SEQUENCE: 63

Gly Val Ser Asn Arg Phe Ser Gly Ser Lys Ser Gly Asn Thr Ala Ser
1               5                   10                  15

Leu Ser Ile Ser Gly Leu Gln Ala Glu Asp Glu Ala Glu Tyr Tyr Cys
                20                  25                  30

<210> SEQ ID NO 64
<211> LENGTH: 32
<212> TYPE: PRT
<213> ORGANISM: human

<400> SEQUENCE: 64

Gly Val Ser Asn Arg Phe Ser Gly Ser Lys Ser Gly Asn Thr Ala Ser
1               5                   10                  15

Leu Ser Ile Ser Gly Leu Gln Ala Glu Asp Glu Ala Gly Tyr Tyr Cys
                20                  25                  30

<210> SEQ ID NO 65
<211> LENGTH: 32
<212> TYPE: PRT
<213> ORGANISM: human

<400> SEQUENCE: 65

Gly Val Ser Asn Arg Phe Ser Gly Ser Lys Ser Gly Asn Thr Ala Ser
1               5                   10                  15

Leu Thr Ile Ser Gly Leu Gln Ala Glu Asp Glu Ala Asp Tyr Tyr Cys
                20                  25                  30
```

<210> SEQ ID NO 66
<211> LENGTH: 32
<212> TYPE: PRT
<213> ORGANISM: human

<400> SEQUENCE: 66

Gly Val Ser Asn Arg Phe Ser Gly Ser Lys Ser Gly Asn Thr Ala Ser
1               5                   10                  15

Leu Ser Ile Ser Gly Leu Gln Ala Glu Asp Glu Ala Asp Tyr Tyr Cys
            20                  25                  30

<210> SEQ ID NO 67
<211> LENGTH: 10
<212> TYPE: PRT
<213> ORGANISM: human

<400> SEQUENCE: 67

Phe Gly Gly Gly Thr Lys Leu Thr Val Leu
1               5                   10

<210> SEQ ID NO 68
<211> LENGTH: 351
<212> TYPE: DNA
<213> ORGANISM: human

<400> SEQUENCE: 68
gaggtgcagc tgttggagtc tggggggaggc ttggtacagc ctgggggggtc cctgagactc      60 tcctgtgcag cctctggatt cacctttagc agctatgcca tgagctgggt ccgccaggct     120
ccagggaagg ggctggagtg ggtctcagct attagtggta gtggtggtag cacatactac     180
gcagactccg tgaagggccg gttcaccatc tccagagaca attccaagaa cacgctgtat     240
ctgcaaatga acagcctgag agccgaggac acggccgtgt attactgtgc gagttgggga     300
acggggacct tgtggccctg gggccaaggg aaaatggtca ccgtctcgag t             351

<210> SEQ ID NO 69
<211> LENGTH: 351
<212> TYPE: DNA
<213> ORGANISM: human
<220> FEATURE:
<221> NAME/KEY: misc_feature
<222> LOCATION: (330)..(330)
<223> OTHER INFORMATION: n is a, c, g, or t
<220> FEATURE:
<221> NAME/KEY: misc_feature
<222> LOCATION: (348)..(348)
<223> OTHER INFORMATION: n is a, c, g, or t

<400> SEQUENCE: 69
gaggtgcagc tgttggagtc tggggggaggc ttggtacagc ctgggggggtc cctgagactc      60 tcctgtgcag cctctggatt cacctttagc agctatgcca tgagctgggt ccgccaggct     120
ccagggaagg ggctggagtg ggtctcagct attagtggta gtggtggtag cacatactac     180
gcagactccg tgaagggccg gttcaccatc tccagagaca attccaagaa cacgctgtat     240
ctgcaaatga acagcctgag agccgaggac acggccgtgt attactgtgc gagttgggga     300
gacgggacct tgaacccgtg gggccaaggn aaaatggtca ccgtctcnag t             351

<210> SEQ ID NO 70
<211> LENGTH: 351
<212> TYPE: DNA
<213> ORGANISM: human

<400> SEQUENCE: 70

```
gaggtgcagc tgttggagtc tgggggaggc ttggtacagc ctgggggtc cctgagactc      60
tcctgtgcag cctctggatt cacctttagc agctatgcca tgagctgggt ccgccaggct    120
ccagggaagg ggctggagtg ggtctcagct attagtggta gtggtggtag cacatactac    180
gcagactccg tgaagggccg gttcaccatc tccagagaca attccaagaa cacgctgtat    240
ctgcaaatga acagcctgag agccgaggac acggccgtgt attactgtgc gagttgggga    300
ctggggagca acgaaaactg gggccaaggg acaatggtca ccgtctcgag t              351
```

<210> SEQ ID NO 71
<211> LENGTH: 351
<212> TYPE: DNA
<213> ORGANISM: human

<400> SEQUENCE: 71

```
gaggtgcagc tgttggagtc tgggggaggc ttggtacagc ctgggggtc cctgagactc      60
tcctgtgcag cctctggatt cacctttagc agctatgcca tgagctgggt ccgccaggct    120
ccagggaagg ggctggagtg ggtctcagct attagtggta gtggtggtag cacatactac    180
gcagactccg tgaagggccg gttcaccatc tccagagaca attccaagaa cacgctgtat    240
ctgcaaatga acagcctgag agccgaggac acggccgtgt attactgtgc ggacacgaac    300
tccgccaagt tcgaccctg gggccaaggg acaatggtca ccgtctcgag t               351
```

<210> SEQ ID NO 72
<211> LENGTH: 351
<212> TYPE: DNA
<213> ORGANISM: human

<400> SEQUENCE: 72

```
gaggtgcagc tgttggagtc tgggggaggc ttggtacagc ctgggggtc cctgagactc      60
tcctgtgcag cctctggatt cacctttagc agctatgcca tgagctgggt ccgccaggct    120
ccagggaagg ggctggagtg ggtctcagct attagtggta gtggtggtag cacatactac    180
gcagactccg tgaagggccg gttcaccatc tccagagaca attccaagaa cacgctgtat    240
ctgcaaatga acagcctgag agccgaggac acggccgtgt attactgtgc gggcacgggg    300
taccctcct tcgaccctg gggccaaggg acaatggtca ccgtctcgag t                351
```

<210> SEQ ID NO 73
<211> LENGTH: 351
<212> TYPE: DNA
<213> ORGANISM: human

<400> SEQUENCE: 73

```
gaggtgcagc tgttggagtc tgggggaggc ttggtacagc ctgggggtc cctgagactc      60
tcctgtgcag cctctggatt cacctttagc agctatgcca tgagctgggt ccgccaggct    120
ccagggaagg ggctggagtg ggtctcagct attagtggta gtggtggtag cacatactac    180
gcagactccg tgaagggccg gttcaccatc tccagagaca attccaagaa cacgctgtat    240
ctgcaaatga acagcctgag agccgaggac acggccgtgt attactgtgc gggcacggcc    300
aagccgagct tcgaccctg gggccaaggg acaatggtca ccgtctcgag t               351
```

<210> SEQ ID NO 74
<211> LENGTH: 351
<212> TYPE: DNA

<213> ORGANISM: human

<400> SEQUENCE: 74

| | | |
|---|---|---|
| gaggtgcagc tgttggagtc tgggggaggc ttggtacagc ctgggggtc cctgagactc | 60 |
| tcctgtgcag cctctggatt cacctttagc agctatgcca tgagctgggt ccgccaggct | 120 |
| ccagggaagg ggctggagtg ggtctcagct attagtggta gtggtggtag cacatactac | 180 |
| gcagactccg tgaagggccg gttcaccatc tccagagaca attccaagaa cacgctgtat | 240 |
| ctgcaaatga acagcctgag agccgaggac acggccgtgt attactgtgc ggggaacgag | 300 |
| aggccgtcgt tcgacccctg gggccaaggg acaatggtca ccgtctcgag t | 351 |

<210> SEQ ID NO 75
<211> LENGTH: 351
<212> TYPE: DNA
<213> ORGANISM: human

<400> SEQUENCE: 75

| | | |
|---|---|---|
| gaggtgcagc tgttggagtc tgggggaggc ttggtacagc ctgggggtc cctgagactc | 60 |
| tcctgtgcag cctctggatt cacctttagc agctatgcca tgagctgggt ccgccaggct | 120 |
| ccagggaagg ggctggagtg ggtctcagct attagtggta gtggtggtag cacatactac | 180 |
| gcagactccg tgaagggccg gttcgccatc tccagagaca attccaagaa cacgctgtat | 240 |
| ctgcaaatga acagcctgag agccgaggac acggccgtgt attactgtgc gggcagccgc | 300 |
| acggtgcagt tcgacccctg gggccaaggg acaatggtca ccgtctcgag t | 351 |

<210> SEQ ID NO 76
<211> LENGTH: 351
<212> TYPE: DNA
<213> ORGANISM: human

<400> SEQUENCE: 76

| | | |
|---|---|---|
| gaggtgcagc tgttggagtc tgggggaggc ttggtacagc ctgggggtc cctgagactc | 60 |
| tcctgtgcag cctctggatt cacctttagc agctatgcca tgagctgggt ccgccaggct | 120 |
| ccagggaagg ggctggagtg ggtctcagct attagtggta gtggtggtag cacatactac | 180 |
| gcagactccg tgaagggccg gttcaccatc tccagagaca attccaagaa cacgctgtat | 240 |
| ctgcaaatga acagcctgag agccgaggac acggccgtgt attactgtgc gacgaactcg | 300 |
| ccggggacgt tcgacccctg gggccaaggg acaatggtca ccgtctcgag t | 351 |

<210> SEQ ID NO 77
<211> LENGTH: 351
<212> TYPE: DNA
<213> ORGANISM: human

<400> SEQUENCE: 77

| | | |
|---|---|---|
| gaggtgcagc tgttggagtc tgggggaggc ttggtacagc ctgggggtc cctgagactc | 60 |
| tcctgtgcag cctctggatt cacctttagc agctatgcca tgagctgggt ccgccaggct | 120 |
| ccagggaagg ggctggagtg ggtctcagct attagtggta gtggtggtag cacatactac | 180 |
| gcagactccg tgaagggccg gttcaccatc tccagagaca attccaagaa cacgctgtat | 240 |
| ctgcaaatga acagcctgag agccgaggac acggccgtgt attactgtgc gaccatcgcg | 300 |
| cccggccggt tcgacccctg gggccaaggg acaatggtca ccgtctcgag t | 351 |

<210> SEQ ID NO 78
<211> LENGTH: 351

```
<212> TYPE: DNA
<213> ORGANISM: human

<400> SEQUENCE: 78
gaggtgcagc tgttggagtc tgggggaggc ttggtacagc ctgggggtc cctgagactc      60 tcctgtgcag cctctggatt cacctttagc agctatgcca tgagctgggt ccgccaggct    120
ccagggaagg ggctggagtg ggtctcagct attagtggta gtggtggtag cacatactac    180
gcagactccg tgaagggccg gttcaccatc tccagagaca attccaagaa cacgctgtat    240
ctgcaaatga acagcctgag agccgaggac acggccgtgt attactgtgc ggggctcgac    300
cgggtgtggt tcgaccctg gggccaaggg acaatggtca ccgtctcgag t              351

<210> SEQ ID NO 79
<211> LENGTH: 351
<212> TYPE: DNA
<213> ORGANISM: human

<400> SEQUENCE: 79
gaggtgcagc tgttggagtc tgggggaggc ttggtacagc ctgggggtc cctgagactc      60 tcctgtgcag cctctggatt cacctttagc agctatgcca tgagctgggt ccgccaggct    120
ccagggaagg ggctggagtg ggtctcagct attagtggta gtggtggtag cacatactac    180
gcagactccg tgaagggccg gttcaccatc tccagagaca attccaagaa cacgctgtat    240
ctgcaaatga acagcctgag agccgaggac acggccgtgt attactgtgc gagttgggga    300
ggaggctggt tcgaccctg gggccaaggg acaatggtca ccgtctcctc a              351

<210> SEQ ID NO 80
<211> LENGTH: 351
<212> TYPE: DNA
<213> ORGANISM: human

<400> SEQUENCE: 80
gaggtgcagc tgttggagtc tgggggaggc ttggtacagc ctgggggtc cctgagactc      60 tcctgtgcag cctctggatt cacctttagc agctatgcca tgagctgggt ccgccaggct    120
ccagggaagg ggctggagtg ggtctcagct attagtggta gtggtggtag cacatactac    180
gcagactccg tgaagggccg gttcaccatc tccagagaca attccaagaa cacgctgtat    240
ctgcaaatga acagcctgag agccgaggac acggccgtgt attactgtgc gaaatgggga    300
ggaggctggt tcgaccctg gggccaaggg acaatggtca ccgtctcctc a              351

<210> SEQ ID NO 81
<211> LENGTH: 333
<212> TYPE: DNA
<213> ORGANISM: human

<400> SEQUENCE: 81
cagtctgccc tgactcagcc tgcctccgtg tctgggtctc ctggacagtc gatcaccatc      60
tcctgcactg gaaccagtaa tgacgttggt gcttataatt atgtctcctg gtaccaacaa    120
cacccaggca aagcccccaa actcattctt tctgaggtca taaacggcc ctcagggggtt    180 tctaatcgct tctctggctc caagtctggc aacacggcct ctctgagcat ctctgggctc    240
caggctgagg acgaggctga ttattactgc agctcattta caagcggcct cccctgggtc    300
ctcttcggcg gagggaccaa gctgaccgtc cta                                  333

<210> SEQ ID NO 82
```

```
<211> LENGTH: 333
<212> TYPE: DNA
<213> ORGANISM: human

<400> SEQUENCE: 82
cagtctgccc tgactcagcc tgcctccgtg tctgggtctc ctggacagtc gatcaccatc    60
tcctgcactg gaaccagtaa tgacgttggt gcttataatt atgtctcctg gtaccaacaa   120
cacccaggca aagcccccaa actcattctt tctgaggtca ataaacggcc ctcaggggtt   180
tctaatcgct tctctggctc caagtctggc aacacggctt ctctgagcat ctctgggctc   240
caggctgagg acgaggctga ttattactgc agctcattta caagcgggct cccctgggtc   300
gtcttcggcg gagggaccaa gctgaccgtc cta                                333

<210> SEQ ID NO 83
<211> LENGTH: 333
<212> TYPE: DNA
<213> ORGANISM: human

<400> SEQUENCE: 83
cagtctgccc tgactcagcc tgcctccgtg tctgggtctc ctggacagtc gatcaccatc    60
tcctgcactg gaaccagtaa tgacgttggt gcttataatt atgtctcctg gtaccaacaa   120
cacccaggca aagcccccaa actcattctt tctgaggtca ataaacggcc ctcaggggtt   180
tctaatcgct tctctggctc caagtctggc aacacggcct ctctgagcat ctctgggctc   240
caggctgagg acgaggctga ttattactgc agctcattta caagcggcat cgtgttcaac   300
ctgttcggcg gagggaccaa gctgaccgtc cta                                333

<210> SEQ ID NO 84
<211> LENGTH: 333
<212> TYPE: DNA
<213> ORGANISM: human

<400> SEQUENCE: 84
cagtctgccc tgactcagcc tgcctccgtg tctgggtctc ctggacagtc gatcaccatc    60
tcctgcactg gaaccagtaa tgacgttggt gcttataatt atgtctcctg gtaccaacga   120
cacccaggca aagcccccaa actcattctt tctgaggtca ataaacggcc ctcagggtt    180
tctaatcgct tctctggctc caagtctggc aacacggcct ctctgagcat ctctgggctc   240
caggctgagg acgaggctga gtattactgc agcagctaca cgatggggag cacttttatg   300
ctattcggcg gagggaccaa gctgaccgtc cta                                333

<210> SEQ ID NO 85
<211> LENGTH: 333
<212> TYPE: DNA
<213> ORGANISM: human

<400> SEQUENCE: 85
cagtctgccc tgactcagcc tgcctccgtg tctgggtctc ctggacagtc gatcaccatc    60
tcctgcactg gaaccagtaa tgacgttggt gcttataatt atgtctcctg gtaccaacaa   120
cacccaggca aagcccccaa actcattctt tctgaggtca ataaacggcc ctcaggggtt   180
tctaatcgct tctctggctc caagtctggc aacacggcct ctctgagcat ctctgggctc   240
caggctgagg acgaggctgg ttattactgc acgagctacc gggccgggag cacttttatg   300
ctattcggcg gagggaccaa gctgaccgtc cta                                333
```

```
<210> SEQ ID NO 86
<211> LENGTH: 333
<212> TYPE: DNA
<213> ORGANISM: human

<400> SEQUENCE: 86
cagtctgccc tgactcagcc tgcctccgtg tctgggcctc ctggacagtc gatcaccatc      60
tcctgcactg gaaccagtaa tgacgttggt gcttataatt atgtctcctg gtaccaacaa     120
cacccaggca aagcccccaa actcattctt tctgaggtca ataaacggcc ctcagggggtt    180
tctaatcgct tctctggctc caagtctggc aacacggcct ctctgagcat ctctgggctc     240
caggctgagg acgaggctga ttattactgc acctcgtaca ccatgggcag cacttttatg     300
ctattcggcg gagggaccaa gctgaccgtc cta                                   333

<210> SEQ ID NO 87
<211> LENGTH: 333
<212> TYPE: DNA
<213> ORGANISM: human

<400> SEQUENCE: 87
cagtctgccc tgactcagcc tgcctccgtg tctgggtctc ctggacagtc gatcaccatc      60
tcctgcactg gaaccagtaa tgacgttggt gcttataatt atgtctcctg gtaccaacaa     120
cacccaggca aagcccccaa actcattctt tctgaggtca ataaacggcc ctcagggggtt    180
tctaatcgct tctctggctc caagtctggc aacacggcct ctctgagcat ctctgggctc     240
caggctgagg acgaggctga ttattactgc acctcgtacc gcatggacag cacttttatg     300
ctattcggcg gagggaccaa gctgaccgtc cta                                   333

<210> SEQ ID NO 88
<211> LENGTH: 333
<212> TYPE: DNA
<213> ORGANISM: human

<400> SEQUENCE: 88
cagtctgccc tgactcagcc tgcctccgtg tctgggtctc ctggacagtc gatcaccatc      60
tcctgcactg gaaccagtaa tgacgttggt gcttataatt atgtctcctg gtaccaacaa     120
cacccaggca aagcccccaa actcattctt tctgaggtca ataaacggcc ctcagggggtt    180
tctaatcgct tctctggctc caagtctggc aacacggcct ctctgagcat ctctgggctc     240
caggctgagg acgaggctga ttattactgc agctcattta caagcggcag cacttttatg     300
ctattcggcg gagggaccaa gctgaccgtc cta                                   333

<210> SEQ ID NO 89
<211> LENGTH: 333
<212> TYPE: DNA
<213> ORGANISM: human

<400> SEQUENCE: 89
cagtctgccc tgactcagcc tgcctccgtg tctgggtctc ctggacagtc gatcaccatc      60
tcctgcactg gaaccagtaa tgacgttggt gcttataatt atgtctcctg gtaccaacaa     120
cacccaggca aagcccccaa actcatgatt tatgaggtca ataaacggcc ctcagggggtt    180
tctaatcgct tctctggctc caagtctggc aacacggcct ctctgaccat ctctgggctc     240
caggctgagg acgaggctga ttattactgc agctcattta caagcggcag cacttttatg     300
ctattcggcg gagggaccaa gctgaccgtc cta                                   333
```

<210> SEQ ID NO 90
<211> LENGTH: 333
<212> TYPE: DNA
<213> ORGANISM: human

<400> SEQUENCE: 90

```
cagtctgccc tgactcagcc tgcctccgtg tctgggtctc ctggacagtc gatcaccatc      60
tcctgcactg gaaccagtaa tgacgttggt gcttataatt atgtctcctg gtaccaacaa     120
cacccaggca aagcccccaa actcattctt tctgaggtca ataaacggcc ctcagggggtt    180 tctaatcgct tctctggctc caagtctggc aacacggcct ctctgagcat ctctgggctc     240
caggctgagg acgaggctga ttattactgc acctcgtaca ccatgggcag cactttatg      300 ctattcggcg gagggaccaa gctgaccgtc cta                                  333
```

<210> SEQ ID NO 91
<211> LENGTH: 8
<212> TYPE: PRT
<213> ORGANISM: human

<400> SEQUENCE: 91

Asn Pro Lys Gly Gln Phe Asp Pro
1               5

<210> SEQ ID NO 92
<211> LENGTH: 8
<212> TYPE: PRT
<213> ORGANISM: human

<400> SEQUENCE: 92

Asn Ser Ala Gly Ser Phe Asp Pro
1               5

<210> SEQ ID NO 93
<211> LENGTH: 8
<212> TYPE: PRT
<213> ORGANISM: human

<400> SEQUENCE: 93

Ser Asn Gly Gly Leu Phe Asp Pro
1               5

<210> SEQ ID NO 94
<211> LENGTH: 8
<212> TYPE: PRT
<213> ORGANISM: human

<400> SEQUENCE: 94

Ser Asn Gly Gly Phe Phe Asp Pro
1               5

<210> SEQ ID NO 95
<211> LENGTH: 8
<212> TYPE: PRT
<213> ORGANISM: human

<400> SEQUENCE: 95

Ser Asp Leu Gly Glu Phe Asp Pro
1               5

<210> SEQ ID NO 96
<211> LENGTH: 8
<212> TYPE: PRT

```
<213> ORGANISM: human

<400> SEQUENCE: 96

Thr Asn Thr Gly Gln Phe Asp Pro
1               5

<210> SEQ ID NO 97
<211> LENGTH: 8
<212> TYPE: PRT
<213> ORGANISM: human

<400> SEQUENCE: 97

Thr Pro Arg Gly Leu Phe Asp Pro
1               5

<210> SEQ ID NO 98
<211> LENGTH: 8
<212> TYPE: PRT
<213> ORGANISM: human

<400> SEQUENCE: 98

Ser Asn Thr Gly Asn Phe Asp Pro
1               5

<210> SEQ ID NO 99
<211> LENGTH: 8
<212> TYPE: PRT
<213> ORGANISM: human

<400> SEQUENCE: 99

Ser Arg Thr Val Gln Phe Asp Pro
1               5

<210> SEQ ID NO 100
<211> LENGTH: 8
<212> TYPE: PRT
<213> ORGANISM: human

<400> SEQUENCE: 100

Leu Gly Val Pro Gln Phe Asp Pro
1               5

<210> SEQ ID NO 101
<211> LENGTH: 8
<212> TYPE: PRT
<213> ORGANISM: human

<400> SEQUENCE: 101

Ser Asp Asn Gly Thr Phe Asp Pro
1               5

<210> SEQ ID NO 102
<211> LENGTH: 8
<212> TYPE: PRT
<213> ORGANISM: human

<400> SEQUENCE: 102

Ile Ala Pro Gly Arg Phe Asp Pro
1               5

<210> SEQ ID NO 103
<211> LENGTH: 8
<212> TYPE: PRT
<213> ORGANISM: human
```

```
<400> SEQUENCE: 103

Asn Thr Thr Gly Thr Phe Asp Pro
1               5

<210> SEQ ID NO 104
<211> LENGTH: 8
<212> TYPE: PRT
<213> ORGANISM: human

<400> SEQUENCE: 104

Ser Asp Ala Gly Arg Phe Asp Pro
1               5

<210> SEQ ID NO 105
<211> LENGTH: 8
<212> TYPE: PRT
<213> ORGANISM: human

<400> SEQUENCE: 105

Ile Asn Glu Gly Arg Phe Asp Pro
1               5

<210> SEQ ID NO 106
<211> LENGTH: 8
<212> TYPE: PRT
<213> ORGANISM: human

<400> SEQUENCE: 106

Asn Ser Asn Gly Val Phe Asp Pro
1               5

<210> SEQ ID NO 107
<211> LENGTH: 8
<212> TYPE: PRT
<213> ORGANISM: human

<400> SEQUENCE: 107

Ser His Ser Gly Lys Phe Asp Pro
1               5

<210> SEQ ID NO 108
<211> LENGTH: 8
<212> TYPE: PRT
<213> ORGANISM: human

<400> SEQUENCE: 108

Asn Lys Lys Pro Pro Phe Asp Pro
1               5

<210> SEQ ID NO 109
<211> LENGTH: 8
<212> TYPE: PRT
<213> ORGANISM: human

<400> SEQUENCE: 109

Ser Asp Asn Gly Leu Phe Asp Pro
1               5

<210> SEQ ID NO 110
<211> LENGTH: 8
<212> TYPE: PRT
<213> ORGANISM: human

<400> SEQUENCE: 110
```

Trp Gly Ala Gly Glu Leu Asp His
1               5

<210> SEQ ID NO 111
<211> LENGTH: 8
<212> TYPE: PRT
<213> ORGANISM: human

<400> SEQUENCE: 111

Trp Gly Thr Gly Ala His Glu Asn
1               5

<210> SEQ ID NO 112
<211> LENGTH: 8
<212> TYPE: PRT
<213> ORGANISM: human

<400> SEQUENCE: 112

Asn Asn Val Gly Arg Phe Asp Pro
1               5

<210> SEQ ID NO 113
<211> LENGTH: 8
<212> TYPE: PRT
<213> ORGANISM: human

<400> SEQUENCE: 113

Thr Asp Arg Pro Val Phe Asp Pro
1               5

<210> SEQ ID NO 114
<211> LENGTH: 8
<212> TYPE: PRT
<213> ORGANISM: human

<400> SEQUENCE: 114

Ile Arg Ser Gly Met Phe Asp Pro
1               5

<210> SEQ ID NO 115
<211> LENGTH: 8
<212> TYPE: PRT
<213> ORGANISM: human

<400> SEQUENCE: 115

Thr Glu Gly Ala Leu Phe Asp Pro
1               5

<210> SEQ ID NO 116
<211> LENGTH: 8
<212> TYPE: PRT
<213> ORGANISM: human

<400> SEQUENCE: 116

Ser Asp Phe Gly Lys Phe Asp Pro
1               5

<210> SEQ ID NO 117
<211> LENGTH: 8
<212> TYPE: PRT
<213> ORGANISM: human

<400> SEQUENCE: 117

Asn Glu Leu Gly Ser Phe Asp Pro
1               5

<210> SEQ ID NO 118
<211> LENGTH: 8
<212> TYPE: PRT
<213> ORGANISM: human

<400> SEQUENCE: 118

Gln Glu Leu Pro Val Phe Asp Pro
1               5

<210> SEQ ID NO 119
<211> LENGTH: 8
<212> TYPE: PRT
<213> ORGANISM: human

<400> SEQUENCE: 119

Phe Arg Asp Thr Ala Phe Asp Pro
1               5

<210> SEQ ID NO 120
<211> LENGTH: 8
<212> TYPE: PRT
<213> ORGANISM: human

<400> SEQUENCE: 120

Ala Asp Met Gly Arg Phe Asp Pro
1               5

<210> SEQ ID NO 121
<211> LENGTH: 8
<212> TYPE: PRT
<213> ORGANISM: human

<400> SEQUENCE: 121

Leu Gly Val Pro Val Phe Asp Pro
1               5

<210> SEQ ID NO 122
<211> LENGTH: 8
<212> TYPE: PRT
<213> ORGANISM: human

<400> SEQUENCE: 122

Thr His Ala Gly Met Phe Asp Pro
1               5

<210> SEQ ID NO 123
<211> LENGTH: 8
<212> TYPE: PRT
<213> ORGANISM: human

<400> SEQUENCE: 123

Val Tyr Ala Gly Arg Phe Asp Pro
1               5

<210> SEQ ID NO 124
<211> LENGTH: 8
<212> TYPE: PRT
<213> ORGANISM: human

<400> SEQUENCE: 124

Asn Thr Gln Gly Arg Phe Asp Pro
1               5

```
<210> SEQ ID NO 125
<211> LENGTH: 8
<212> TYPE: PRT
<213> ORGANISM: human

<400> SEQUENCE: 125

Thr Asn Gly Gly Leu Phe Asp Pro
1               5

<210> SEQ ID NO 126
<211> LENGTH: 8
<212> TYPE: PRT
<213> ORGANISM: human

<400> SEQUENCE: 126

Ile Thr Thr Val Lys Phe Asp Pro
1               5

<210> SEQ ID NO 127
<211> LENGTH: 8
<212> TYPE: PRT
<213> ORGANISM: human

<400> SEQUENCE: 127

Arg Leu Val His Gly Phe Asp Pro
1               5

<210> SEQ ID NO 128
<211> LENGTH: 8
<212> TYPE: PRT
<213> ORGANISM: human

<400> SEQUENCE: 128

Ile Arg Leu Gly Thr Phe Asp Pro
1               5

<210> SEQ ID NO 129
<211> LENGTH: 8
<212> TYPE: PRT
<213> ORGANISM: human

<400> SEQUENCE: 129

Ser Glu Arg Pro Gln Phe Asp Pro
1               5

<210> SEQ ID NO 130
<211> LENGTH: 8
<212> TYPE: PRT
<213> ORGANISM: human

<400> SEQUENCE: 130

Thr Ser Arg Pro Leu Phe Asp Pro
1               5

<210> SEQ ID NO 131
<211> LENGTH: 8
<212> TYPE: PRT
<213> ORGANISM: human

<400> SEQUENCE: 131

Val Glu Ser Gly Arg Phe Asp Pro
1               5

<210> SEQ ID NO 132
<211> LENGTH: 8
```

```
<212> TYPE: PRT
<213> ORGANISM: human

<400> SEQUENCE: 132

Ser Glu Met Pro Met Phe Asp Pro
1               5

<210> SEQ ID NO 133
<211> LENGTH: 8
<212> TYPE: PRT
<213> ORGANISM: human

<400> SEQUENCE: 133

Val Asn Pro Gly Tyr Phe Asp Pro
1               5

<210> SEQ ID NO 134
<211> LENGTH: 8
<212> TYPE: PRT
<213> ORGANISM: human

<400> SEQUENCE: 134

Asn Asp Ile Ala Arg Phe Asp Pro
1               5

<210> SEQ ID NO 135
<211> LENGTH: 8
<212> TYPE: PRT
<213> ORGANISM: human

<400> SEQUENCE: 135

Val Gly Val Gly Gln Phe Asp Pro
1               5

<210> SEQ ID NO 136
<211> LENGTH: 8
<212> TYPE: PRT
<213> ORGANISM: human

<400> SEQUENCE: 136

Thr Arg Tyr Pro Thr Phe Asp Pro
1               5

<210> SEQ ID NO 137
<211> LENGTH: 8
<212> TYPE: PRT
<213> ORGANISM: human

<400> SEQUENCE: 137

Asn Ser Ala Gly Thr Phe Asp Pro
1               5

<210> SEQ ID NO 138
<211> LENGTH: 8
<212> TYPE: PRT
<213> ORGANISM: human

<400> SEQUENCE: 138

Val Asn Glu Gly Arg Phe Asp Pro
1               5

<210> SEQ ID NO 139
<211> LENGTH: 8
<212> TYPE: PRT
<213> ORGANISM: human
```

<400> SEQUENCE: 139

Asn Arg Thr Gly Arg Phe Asp Pro
1               5

<210> SEQ ID NO 140
<211> LENGTH: 8
<212> TYPE: PRT
<213> ORGANISM: human

<400> SEQUENCE: 140

Asn Ala Ser Ala Arg Phe Asp Pro
1               5

<210> SEQ ID NO 141
<211> LENGTH: 8
<212> TYPE: PRT
<213> ORGANISM: human

<400> SEQUENCE: 141

Ile Asn Thr Gly Met Phe Asp Pro
1               5

<210> SEQ ID NO 142
<211> LENGTH: 8
<212> TYPE: PRT
<213> ORGANISM: human

<400> SEQUENCE: 142

Asn Asp Asn Gly Arg Phe Asp Pro
1               5

<210> SEQ ID NO 143
<211> LENGTH: 8
<212> TYPE: PRT
<213> ORGANISM: human

<400> SEQUENCE: 143

Val Asp Gln Pro Ser Phe Asp Pro
1               5

<210> SEQ ID NO 144
<211> LENGTH: 8
<212> TYPE: PRT
<213> ORGANISM: human

<400> SEQUENCE: 144

Val Asp Arg Gly Gln Phe Asp Pro
1               5

<210> SEQ ID NO 145
<211> LENGTH: 8
<212> TYPE: PRT
<213> ORGANISM: human

<400> SEQUENCE: 145

Asn His Thr Gly Lys Phe Asp Pro
1               5

<210> SEQ ID NO 146
<211> LENGTH: 8
<212> TYPE: PRT
<213> ORGANISM: human

<400> SEQUENCE: 146

Thr Asn Thr Gly Arg Phe Asp Pro
1               5

<210> SEQ ID NO 147
<211> LENGTH: 8
<212> TYPE: PRT
<213> ORGANISM: human

<400> SEQUENCE: 147

Ser Asp Ser Gly Leu Phe Asp Pro
1               5

<210> SEQ ID NO 148
<211> LENGTH: 8
<212> TYPE: PRT
<213> ORGANISM: human

<400> SEQUENCE: 148

Asn Val Leu Ala Leu Phe Asp Pro
1               5

<210> SEQ ID NO 149
<211> LENGTH: 8
<212> TYPE: PRT
<213> ORGANISM: human

<400> SEQUENCE: 149

Asn Tyr Glu Ala Arg Phe Asp Pro
1               5

<210> SEQ ID NO 150
<211> LENGTH: 8
<212> TYPE: PRT
<213> ORGANISM: human

<400> SEQUENCE: 150

Pro Asp Asn Gly Thr Phe Asp Pro
1               5

<210> SEQ ID NO 151
<211> LENGTH: 8
<212> TYPE: PRT
<213> ORGANISM: human

<400> SEQUENCE: 151

Asn Arg Asn Gly Asn Phe Asp Pro
1               5

<210> SEQ ID NO 152
<211> LENGTH: 8
<212> TYPE: PRT
<213> ORGANISM: human

<400> SEQUENCE: 152

Thr Thr Gly Gly Arg Phe Asp Pro
1               5

<210> SEQ ID NO 153
<211> LENGTH: 8
<212> TYPE: PRT
<213> ORGANISM: human

<400> SEQUENCE: 153

Thr Gly Tyr Pro Ser Phe Asp Pro

```
1               5

<210> SEQ ID NO 154
<211> LENGTH: 8
<212> TYPE: PRT
<213> ORGANISM: human

<400> SEQUENCE: 154

Asn Asn Glu Gly Gln Phe Asp Pro
1               5

<210> SEQ ID NO 155
<211> LENGTH: 8
<212> TYPE: PRT
<213> ORGANISM: human

<400> SEQUENCE: 155

Asn Ser Lys Gly Arg Phe Asp Pro
1               5

<210> SEQ ID NO 156
<211> LENGTH: 8
<212> TYPE: PRT
<213> ORGANISM: human

<400> SEQUENCE: 156

Thr Glu Asn Pro Thr Phe Asp Pro
1               5

<210> SEQ ID NO 157
<211> LENGTH: 8
<212> TYPE: PRT
<213> ORGANISM: human

<400> SEQUENCE: 157

Thr Asn Gly Gly Arg Phe Asp Pro
1               5

<210> SEQ ID NO 158
<211> LENGTH: 8
<212> TYPE: PRT
<213> ORGANISM: human

<400> SEQUENCE: 158

Asn Ser Tyr Gly Ser Phe Asp Pro
1               5

<210> SEQ ID NO 159
<211> LENGTH: 8
<212> TYPE: PRT
<213> ORGANISM: human

<400> SEQUENCE: 159

Leu Glu Asn Val Val Phe Asp Pro
1               5

<210> SEQ ID NO 160
<211> LENGTH: 8
<212> TYPE: PRT
<213> ORGANISM: human

<400> SEQUENCE: 160

Ala Asn His Gly Arg Phe Asp Pro
1               5
```

```
<210> SEQ ID NO 161
<211> LENGTH: 8
<212> TYPE: PRT
<213> ORGANISM: human

<400> SEQUENCE: 161

Ala Asn Gly Gly Gln Phe Asp Pro
1               5

<210> SEQ ID NO 162
<211> LENGTH: 8
<212> TYPE: PRT
<213> ORGANISM: human

<400> SEQUENCE: 162

Trp Gly Asn Asp Ala Ser Leu Gly
1               5

<210> SEQ ID NO 163
<211> LENGTH: 8
<212> TYPE: PRT
<213> ORGANISM: human

<400> SEQUENCE: 163

Trp Gly Pro Thr Ala Ser Leu Asp
1               5

<210> SEQ ID NO 164
<211> LENGTH: 8
<212> TYPE: PRT
<213> ORGANISM: human

<400> SEQUENCE: 164

Trp Gly Arg Gly Thr Asn Glu Tyr
1               5

<210> SEQ ID NO 165
<211> LENGTH: 8
<212> TYPE: PRT
<213> ORGANISM: human

<400> SEQUENCE: 165

Trp Gly Gly Gly Gly His Tyr Asp
1               5

<210> SEQ ID NO 166
<211> LENGTH: 8
<212> TYPE: PRT
<213> ORGANISM: human

<400> SEQUENCE: 166

Trp Gly Ala Asp Ala Thr Leu Asp
1               5

<210> SEQ ID NO 167
<211> LENGTH: 8
<212> TYPE: PRT
<213> ORGANISM: human

<400> SEQUENCE: 167

Thr Glu Phe Gly Thr Phe Asp Pro
1               5

<210> SEQ ID NO 168
```

```
<211> LENGTH: 8
<212> TYPE: PRT
<213> ORGANISM: human

<400> SEQUENCE: 168

Asn Ala Thr Gly Thr Phe Asp Pro
1               5

<210> SEQ ID NO 169
<211> LENGTH: 8
<212> TYPE: PRT
<213> ORGANISM: human

<400> SEQUENCE: 169

Thr Asn Ser Ala Lys Phe Asp Pro
1               5

<210> SEQ ID NO 170
<211> LENGTH: 8
<212> TYPE: PRT
<213> ORGANISM: human

<400> SEQUENCE: 170

Val Asn Ser Gly Lys Phe Asp Pro
1               5

<210> SEQ ID NO 171
<211> LENGTH: 8
<212> TYPE: PRT
<213> ORGANISM: human

<400> SEQUENCE: 171

Ser Leu Arg Val Glu Phe Asp Pro
1               5

<210> SEQ ID NO 172
<211> LENGTH: 8
<212> TYPE: PRT
<213> ORGANISM: human

<400> SEQUENCE: 172

Asn Asp Arg Gly Met Phe Asp Pro
1               5

<210> SEQ ID NO 173
<211> LENGTH: 8
<212> TYPE: PRT
<213> ORGANISM: human

<400> SEQUENCE: 173

Asn Ser Pro Gly Thr Phe Asp Pro
1               5

<210> SEQ ID NO 174
<211> LENGTH: 8
<212> TYPE: PRT
<213> ORGANISM: human

<400> SEQUENCE: 174

Asn Thr Ala Gly Arg Phe Asp Pro
1               5

<210> SEQ ID NO 175
<211> LENGTH: 8
<212> TYPE: PRT
```

```
<213> ORGANISM: human

<400> SEQUENCE: 175

Val Asn Arg Gly Arg Phe Asp Pro
1               5

<210> SEQ ID NO 176
<211> LENGTH: 8
<212> TYPE: PRT
<213> ORGANISM: human

<400> SEQUENCE: 176

Thr Glu Lys Pro Met Phe Asp Pro
1               5

<210> SEQ ID NO 177
<211> LENGTH: 8
<212> TYPE: PRT
<213> ORGANISM: human

<400> SEQUENCE: 177

Trp Ser Val Ser Leu Phe Asp Pro
1               5

<210> SEQ ID NO 178
<211> LENGTH: 8
<212> TYPE: PRT
<213> ORGANISM: human

<400> SEQUENCE: 178

Met Glu Val Val Glu Phe Asp Pro
1               5

<210> SEQ ID NO 179
<211> LENGTH: 8
<212> TYPE: PRT
<213> ORGANISM: human

<400> SEQUENCE: 179

Val Asn His Gly Arg Phe Asp Pro
1               5

<210> SEQ ID NO 180
<211> LENGTH: 8
<212> TYPE: PRT
<213> ORGANISM: human

<400> SEQUENCE: 180

Thr Glu Val Gly Thr Phe Asp Pro
1               5

<210> SEQ ID NO 181
<211> LENGTH: 8
<212> TYPE: PRT
<213> ORGANISM: human

<400> SEQUENCE: 181

Thr Asp Lys Pro Val Phe Asp Pro
1               5

<210> SEQ ID NO 182
<211> LENGTH: 8
<212> TYPE: PRT
<213> ORGANISM: human
```

```
<400> SEQUENCE: 182

Leu Glu Leu Pro Arg Phe Asp Pro
1               5

<210> SEQ ID NO 183
<211> LENGTH: 8
<212> TYPE: PRT
<213> ORGANISM: human

<400> SEQUENCE: 183

Thr Asn His Ala Met Phe Asp Pro
1               5

<210> SEQ ID NO 184
<211> LENGTH: 8
<212> TYPE: PRT
<213> ORGANISM: human

<400> SEQUENCE: 184

Thr His Ser Gly Arg Phe Asp Pro
1               5

<210> SEQ ID NO 185
<211> LENGTH: 8
<212> TYPE: PRT
<213> ORGANISM: human

<400> SEQUENCE: 185

Asn Asp Arg Gly Gly Phe Asp Pro
1               5

<210> SEQ ID NO 186
<211> LENGTH: 8
<212> TYPE: PRT
<213> ORGANISM: human

<400> SEQUENCE: 186

Pro His Arg Gly Thr Phe Asp Pro
1               5

<210> SEQ ID NO 187
<211> LENGTH: 8
<212> TYPE: PRT
<213> ORGANISM: human

<400> SEQUENCE: 187

Thr Glu Leu Gly Gln Phe Asp Pro
1               5

<210> SEQ ID NO 188
<211> LENGTH: 8
<212> TYPE: PRT
<213> ORGANISM: human

<400> SEQUENCE: 188

Trp Gly Leu Gly Ser Asn Glu Asn
1               5

<210> SEQ ID NO 189
<211> LENGTH: 8
<212> TYPE: PRT
<213> ORGANISM: human

<400> SEQUENCE: 189
```

Trp Gly Asn Asp Ala Thr Trp Asn
1               5

<210> SEQ ID NO 190
<211> LENGTH: 8
<212> TYPE: PRT
<213> ORGANISM: human

<400> SEQUENCE: 190

Trp Gly Ser Thr Ala Ser Leu Asp
1               5

<210> SEQ ID NO 191
<211> LENGTH: 8
<212> TYPE: PRT
<213> ORGANISM: human

<400> SEQUENCE: 191

Trp Gly Gly Gly Gly His Gln Asp
1               5

<210> SEQ ID NO 192
<211> LENGTH: 8
<212> TYPE: PRT
<213> ORGANISM: human

<400> SEQUENCE: 192

Trp Gly Arg Gly Asp Trp Arg Ser
1               5

<210> SEQ ID NO 193
<211> LENGTH: 8
<212> TYPE: PRT
<213> ORGANISM: human

<400> SEQUENCE: 193

Trp Gly Ser Thr Ala Ser Leu Ser
1               5

<210> SEQ ID NO 194
<211> LENGTH: 8
<212> TYPE: PRT
<213> ORGANISM: human

<400> SEQUENCE: 194

Trp Gly His Gly Gly His Asp Thr
1               5

<210> SEQ ID NO 195
<211> LENGTH: 8
<212> TYPE: PRT
<213> ORGANISM: human

<400> SEQUENCE: 195

Trp Gly Pro Arg Ala Thr Leu Asp
1               5

<210> SEQ ID NO 196
<211> LENGTH: 8
<212> TYPE: PRT
<213> ORGANISM: human

<400> SEQUENCE: 196

Trp Gly Asn Gly Ala Phe Val Pro
1               5

<210> SEQ ID NO 197
<211> LENGTH: 8
<212> TYPE: PRT
<213> ORGANISM: human

<400> SEQUENCE: 197

Trp Gly Asn Asp Ala Thr Leu Ala
1               5

<210> SEQ ID NO 198
<211> LENGTH: 8
<212> TYPE: PRT
<213> ORGANISM: human

<400> SEQUENCE: 198

Trp Gly Ser Gly Asn Leu Asp Pro
1               5

<210> SEQ ID NO 199
<211> LENGTH: 8
<212> TYPE: PRT
<213> ORGANISM: human

<400> SEQUENCE: 199

Asn Glu Leu Pro Lys Phe Asp Pro
1               5

<210> SEQ ID NO 200
<211> LENGTH: 8
<212> TYPE: PRT
<213> ORGANISM: human

<400> SEQUENCE: 200

Ser Asp Gly Gly Thr Phe Asp Pro
1               5

<210> SEQ ID NO 201
<211> LENGTH: 8
<212> TYPE: PRT
<213> ORGANISM: human

<400> SEQUENCE: 201

Leu Asp Met Val Met Phe Asp Pro
1               5

<210> SEQ ID NO 202
<211> LENGTH: 8
<212> TYPE: PRT
<213> ORGANISM: human

<400> SEQUENCE: 202

Trp Gly Ser Gly Thr Met Asp Pro
1               5

<210> SEQ ID NO 203
<211> LENGTH: 8
<212> TYPE: PRT
<213> ORGANISM: human

<400> SEQUENCE: 203

Pro Asp Arg Gly Lys Phe Asp Pro
1               5

```
<210> SEQ ID NO 204
<211> LENGTH: 8
<212> TYPE: PRT
<213> ORGANISM: human

<400> SEQUENCE: 204

Thr His Asn Pro Val Phe Asp Pro
1               5

<210> SEQ ID NO 205
<211> LENGTH: 8
<212> TYPE: PRT
<213> ORGANISM: human

<400> SEQUENCE: 205

Asn Ser Ala Gly Arg Phe Asp Pro
1               5

<210> SEQ ID NO 206
<211> LENGTH: 8
<212> TYPE: PRT
<213> ORGANISM: human

<400> SEQUENCE: 206

Leu Asp Ser Val Val Phe Asp Pro
1               5

<210> SEQ ID NO 207
<211> LENGTH: 8
<212> TYPE: PRT
<213> ORGANISM: human

<400> SEQUENCE: 207

Trp Gly Thr Gly Gln His Glu Asn
1               5

<210> SEQ ID NO 208
<211> LENGTH: 8
<212> TYPE: PRT
<213> ORGANISM: human

<400> SEQUENCE: 208

Trp Gly Thr Gly His His Asp Pro
1               5

<210> SEQ ID NO 209
<211> LENGTH: 8
<212> TYPE: PRT
<213> ORGANISM: human

<400> SEQUENCE: 209

Asn Phe Lys Pro Ser Phe Asp Pro
1               5

<210> SEQ ID NO 210
<211> LENGTH: 8
<212> TYPE: PRT
<213> ORGANISM: human

<400> SEQUENCE: 210

Ala Asn Gly Gly Arg Phe Asp Pro
1               5

<210> SEQ ID NO 211
<211> LENGTH: 8
```

```
<212> TYPE: PRT
<213> ORGANISM: human

<400> SEQUENCE: 211

Trp Gly Thr Gly His Leu Glu Pro
1               5

<210> SEQ ID NO 212
<211> LENGTH: 8
<212> TYPE: PRT
<213> ORGANISM: human

<400> SEQUENCE: 212

Thr Gly Leu Pro Arg Phe Asp Pro
1               5

<210> SEQ ID NO 213
<211> LENGTH: 8
<212> TYPE: PRT
<213> ORGANISM: human

<400> SEQUENCE: 213

Ser Asn Val Gly Lys Phe Asp Pro
1               5

<210> SEQ ID NO 214
<211> LENGTH: 8
<212> TYPE: PRT
<213> ORGANISM: human

<400> SEQUENCE: 214

Asn Ala Val Ala Arg Phe Asp Pro
1               5

<210> SEQ ID NO 215
<211> LENGTH: 8
<212> TYPE: PRT
<213> ORGANISM: human

<400> SEQUENCE: 215

Thr Asp Arg Pro Gln Phe Asp Pro
1               5

<210> SEQ ID NO 216
<211> LENGTH: 8
<212> TYPE: PRT
<213> ORGANISM: human

<400> SEQUENCE: 216

Ser Leu Thr Val Asp Phe Asp Pro
1               5

<210> SEQ ID NO 217
<211> LENGTH: 8
<212> TYPE: PRT
<213> ORGANISM: human

<400> SEQUENCE: 217

Thr Glu Met Ala Gln Phe Asp Pro
1               5

<210> SEQ ID NO 218
<211> LENGTH: 8
<212> TYPE: PRT
<213> ORGANISM: human
```

<400> SEQUENCE: 218

Trp Gly Glu Gly His Leu Glu Tyr
1               5

<210> SEQ ID NO 219
<211> LENGTH: 8
<212> TYPE: PRT
<213> ORGANISM: human

<400> SEQUENCE: 219

Gln Lys Lys Val Glu Phe Asp Pro
1               5

<210> SEQ ID NO 220
<211> LENGTH: 8
<212> TYPE: PRT
<213> ORGANISM: human

<400> SEQUENCE: 220

Thr Gly Tyr Pro Val Phe Asn Pro
1               5

<210> SEQ ID NO 221
<211> LENGTH: 8
<212> TYPE: PRT
<213> ORGANISM: human

<400> SEQUENCE: 221

Ala Asn Ser Ala Lys Phe Asp Pro
1               5

<210> SEQ ID NO 222
<211> LENGTH: 8
<212> TYPE: PRT
<213> ORGANISM: human

<400> SEQUENCE: 222

Val Gly Arg Pro Gln Phe Asp Pro
1               5

<210> SEQ ID NO 223
<211> LENGTH: 8
<212> TYPE: PRT
<213> ORGANISM: human

<400> SEQUENCE: 223

Thr Tyr Asn Pro Met Phe Asp Pro
1               5

<210> SEQ ID NO 224
<211> LENGTH: 8
<212> TYPE: PRT
<213> ORGANISM: human

<400> SEQUENCE: 224

Thr Glu Arg Pro Val Phe Asp Pro
1               5

<210> SEQ ID NO 225
<211> LENGTH: 8
<212> TYPE: PRT
<213> ORGANISM: human

<400> SEQUENCE: 225

```
Leu Asp Leu Pro Arg Phe Asp Pro
1               5

<210> SEQ ID NO 226
<211> LENGTH: 8
<212> TYPE: PRT
<213> ORGANISM: human

<400> SEQUENCE: 226

Trp Gly Ser Gly Ser Ile Asp His
1               5

<210> SEQ ID NO 227
<211> LENGTH: 8
<212> TYPE: PRT
<213> ORGANISM: human

<400> SEQUENCE: 227

Leu Asp Arg Val Cys Ser Arg Trp
1               5

<210> SEQ ID NO 228
<211> LENGTH: 8
<212> TYPE: PRT
<213> ORGANISM: human

<400> SEQUENCE: 228

Asn Thr Leu Pro Val Phe Asp Pro
1               5

<210> SEQ ID NO 229
<211> LENGTH: 8
<212> TYPE: PRT
<213> ORGANISM: human

<400> SEQUENCE: 229

Ile Lys Pro Gly Arg Phe Asp Pro
1               5

<210> SEQ ID NO 230
<211> LENGTH: 8
<212> TYPE: PRT
<213> ORGANISM: human

<400> SEQUENCE: 230

Thr Gly Tyr Pro Val Phe Asp Pro
1               5

<210> SEQ ID NO 231
<211> LENGTH: 8
<212> TYPE: PRT
<213> ORGANISM: human

<400> SEQUENCE: 231

Ile Lys Pro Gly Met Phe Asp Pro
1               5

<210> SEQ ID NO 232
<211> LENGTH: 8
<212> TYPE: PRT
<213> ORGANISM: human

<400> SEQUENCE: 232

Asn Met Thr Pro Arg Phe Asp Pro
```

```
<210> SEQ ID NO 233
<211> LENGTH: 8
<212> TYPE: PRT
<213> ORGANISM: human

<400> SEQUENCE: 233

Thr Glu Arg Pro Ser Phe Asp Pro
1               5

<210> SEQ ID NO 234
<211> LENGTH: 8
<212> TYPE: PRT
<213> ORGANISM: human

<400> SEQUENCE: 234

Thr Asn Tyr Gly Thr Phe Asp Pro
1               5

<210> SEQ ID NO 235
<211> LENGTH: 8
<212> TYPE: PRT
<213> ORGANISM: human

<400> SEQUENCE: 235

Thr Ser Arg Pro Ser Phe Asp Pro
1               5

<210> SEQ ID NO 236
<211> LENGTH: 8
<212> TYPE: PRT
<213> ORGANISM: human

<400> SEQUENCE: 236

Thr Tyr Trp Pro Ala Phe Asp Pro
1               5

<210> SEQ ID NO 237
<211> LENGTH: 8
<212> TYPE: PRT
<213> ORGANISM: human

<400> SEQUENCE: 237

Ile Asp Met Pro Trp Phe Asp Pro
1               5

<210> SEQ ID NO 238
<211> LENGTH: 8
<212> TYPE: PRT
<213> ORGANISM: human

<400> SEQUENCE: 238

Trp Gly Thr Gly His His Asp Pro
1               5

<210> SEQ ID NO 239
<211> LENGTH: 8
<212> TYPE: PRT
<213> ORGANISM: human

<400> SEQUENCE: 239

Asn Ala Arg Pro Ser Phe Asp Pro
1               5
```

<210> SEQ ID NO 240
<211> LENGTH: 8
<212> TYPE: PRT
<213> ORGANISM: human

<400> SEQUENCE: 240

Asn Gln Ile Val His Phe Asp Pro
1               5

<210> SEQ ID NO 241
<211> LENGTH: 8
<212> TYPE: PRT
<213> ORGANISM: human

<400> SEQUENCE: 241

Asn Val Met Gly Arg Phe Asp Pro
1               5

<210> SEQ ID NO 242
<211> LENGTH: 8
<212> TYPE: PRT
<213> ORGANISM: human

<400> SEQUENCE: 242

Thr Asp Thr Pro Val Phe Asp Pro
1               5

<210> SEQ ID NO 243
<211> LENGTH: 8
<212> TYPE: PRT
<213> ORGANISM: human

<400> SEQUENCE: 243

Asn Arg Thr Val Trp Phe Asp Pro
1               5

<210> SEQ ID NO 244
<211> LENGTH: 8
<212> TYPE: PRT
<213> ORGANISM: human

<400> SEQUENCE: 244

Asn Arg Met Gly Ser Phe Asp Pro
1               5

<210> SEQ ID NO 245
<211> LENGTH: 8
<212> TYPE: PRT
<213> ORGANISM: human

<400> SEQUENCE: 245

Val Lys Pro Gly Phe Phe Asp Pro
1               5

<210> SEQ ID NO 246
<211> LENGTH: 8
<212> TYPE: PRT
<213> ORGANISM: human

<400> SEQUENCE: 246

Ile Asp Gln Gly Arg Phe Asp Pro
1               5

<210> SEQ ID NO 247

```
<211> LENGTH: 8
<212> TYPE: PRT
<213> ORGANISM: human

<400> SEQUENCE: 247

Gln Ser Leu Pro Gln Phe Asp Pro
1               5

<210> SEQ ID NO 248
<211> LENGTH: 8
<212> TYPE: PRT
<213> ORGANISM: human

<400> SEQUENCE: 248

Asn Glu Leu Gly Thr Phe Asp Pro
1               5

<210> SEQ ID NO 249
<211> LENGTH: 8
<212> TYPE: PRT
<213> ORGANISM: human

<400> SEQUENCE: 249

Gln Lys Lys Val Glu Phe Asp Pro
1               5

<210> SEQ ID NO 250
<211> LENGTH: 8
<212> TYPE: PRT
<213> ORGANISM: human

<400> SEQUENCE: 250

Ile Asp Thr Pro Thr Phe Asp Pro
1               5

<210> SEQ ID NO 251
<211> LENGTH: 8
<212> TYPE: PRT
<213> ORGANISM: human

<400> SEQUENCE: 251

Trp Gly Tyr Asp Ala Thr Leu Glu
1               5

<210> SEQ ID NO 252
<211> LENGTH: 8
<212> TYPE: PRT
<213> ORGANISM: human

<400> SEQUENCE: 252

Ser Asp Gly Gly Lys Phe Asp Pro
1               5

<210> SEQ ID NO 253
<211> LENGTH: 8
<212> TYPE: PRT
<213> ORGANISM: human

<400> SEQUENCE: 253

Leu Asp Leu Val Arg Phe Asp Pro
1               5

<210> SEQ ID NO 254
<211> LENGTH: 8
<212> TYPE: PRT
```

```
<213> ORGANISM: human

<400> SEQUENCE: 254

Ala Asn Ala Gly Leu Phe Asp Pro
1               5

<210> SEQ ID NO 255
<211> LENGTH: 8
<212> TYPE: PRT
<213> ORGANISM: human

<400> SEQUENCE: 255

Trp Gly Thr Gly Ser Asn Arg Asp
1               5

<210> SEQ ID NO 256
<211> LENGTH: 8
<212> TYPE: PRT
<213> ORGANISM: human

<400> SEQUENCE: 256

Ser Glu Thr Ile Asn Phe Asp Pro
1               5

<210> SEQ ID NO 257
<211> LENGTH: 11
<212> TYPE: PRT
<213> ORGANISM: human

<400> SEQUENCE: 257

Gly Ser Tyr Thr His Gly Ser Thr Phe Met Leu
1               5                   10

<210> SEQ ID NO 258
<211> LENGTH: 11
<212> TYPE: PRT
<213> ORGANISM: human

<400> SEQUENCE: 258

Ser Ser Phe Thr Ser Gly Ile Pro Trp Ala Val
1               5                   10

<210> SEQ ID NO 259
<211> LENGTH: 11
<212> TYPE: PRT
<213> ORGANISM: human

<400> SEQUENCE: 259

Ser Ser Phe Thr Ser Gly Val Pro Trp Ala Met
1               5                   10

<210> SEQ ID NO 260
<211> LENGTH: 11
<212> TYPE: PRT
<213> ORGANISM: human

<400> SEQUENCE: 260

Ser Ser Phe Thr Ser Gly Leu Gln Trp Val Val
1               5                   10

<210> SEQ ID NO 261
<211> LENGTH: 11
<212> TYPE: PRT
<213> ORGANISM: human
```

```
<400> SEQUENCE: 261

Ser Ser Phe Thr Ser Gln Ile Pro Trp Ala Leu
1               5                   10

<210> SEQ ID NO 262
<211> LENGTH: 11
<212> TYPE: PRT
<213> ORGANISM: human

<400> SEQUENCE: 262

Ser Ser Phe Thr Ser Ala Glu Gln Trp Val Met
1               5                   10

<210> SEQ ID NO 263
<211> LENGTH: 11
<212> TYPE: PRT
<213> ORGANISM: human

<400> SEQUENCE: 263

Ser Ser Phe Thr Ser Gln Pro Gln Phe Asn Leu
1               5                   10

<210> SEQ ID NO 264
<211> LENGTH: 11
<212> TYPE: PRT
<213> ORGANISM: human

<400> SEQUENCE: 264

Ser Ser Phe Thr Ser Gly Ser Thr Trp Val Leu
1               5                   10

<210> SEQ ID NO 265
<211> LENGTH: 11
<212> TYPE: PRT
<213> ORGANISM: human

<400> SEQUENCE: 265

Ser Ser Phe Thr Ser Ala Val Pro Trp Ala Ile
1               5                   10

<210> SEQ ID NO 266
<211> LENGTH: 11
<212> TYPE: PRT
<213> ORGANISM: human

<400> SEQUENCE: 266

Ser Ser Phe Thr Ser Gly Ala Val Phe Val Leu
1               5                   10

<210> SEQ ID NO 267
<211> LENGTH: 11
<212> TYPE: PRT
<213> ORGANISM: human

<400> SEQUENCE: 267

Ser Ser Phe Thr Ser Gly Ile Val Phe Asn Leu
1               5                   10

<210> SEQ ID NO 268
<211> LENGTH: 11
<212> TYPE: PRT
<213> ORGANISM: human

<400> SEQUENCE: 268
```

```
Ala Ser Tyr Arg Asp Gly Ser Thr Phe Met Leu
1               5                   10
```

<210> SEQ ID NO 269
<211> LENGTH: 11
<212> TYPE: PRT
<213> ORGANISM: human

<400> SEQUENCE: 269

```
Ala Ser Phe Gln Ser Gly Ser Thr Phe Met Leu
1               5                   10
```

<210> SEQ ID NO 270
<211> LENGTH: 11
<212> TYPE: PRT
<213> ORGANISM: human

<400> SEQUENCE: 270

```
Ala Ser Tyr Gln Ser Ala Ser Thr Phe Met Leu
1               5                   10
```

<210> SEQ ID NO 271
<211> LENGTH: 11
<212> TYPE: PRT
<213> ORGANISM: human

<400> SEQUENCE: 271

```
Thr Ser Tyr Thr Ala Ser Ser Thr Phe Met Leu
1               5                   10
```

<210> SEQ ID NO 272
<211> LENGTH: 11
<212> TYPE: PRT
<213> ORGANISM: human

<400> SEQUENCE: 272

```
Ser Ala Phe Gln Gln Ser Ser Thr Phe Met Leu
1               5                   10
```

<210> SEQ ID NO 273
<211> LENGTH: 11
<212> TYPE: PRT
<213> ORGANISM: human

<400> SEQUENCE: 273

```
Gly Ser Tyr Ser Gln Gln Ser Thr Phe Met Leu
1               5                   10
```

<210> SEQ ID NO 274
<211> LENGTH: 11
<212> TYPE: PRT
<213> ORGANISM: human

<400> SEQUENCE: 274

```
Gly Ala Tyr Ser Ala Gly Ser Thr Phe Met Leu
1               5                   10
```

<210> SEQ ID NO 275
<211> LENGTH: 11
<212> TYPE: PRT
<213> ORGANISM: human

<400> SEQUENCE: 275

```
Thr Ser Tyr Thr Gln Gly Ser Thr Phe Met Leu
1               5                   10
```

<210> SEQ ID NO 276
<211> LENGTH: 11
<212> TYPE: PRT
<213> ORGANISM: human

<400> SEQUENCE: 276

Ser Ser Phe Thr Ser Gly Arg Ala Phe Thr Cys
1               5                   10

<210> SEQ ID NO 277
<211> LENGTH: 11
<212> TYPE: PRT
<213> ORGANISM: human

<400> SEQUENCE: 277

Ser Ser Phe Thr Ser Gly Asp His Trp Val Leu
1               5                   10

<210> SEQ ID NO 278
<211> LENGTH: 11
<212> TYPE: PRT
<213> ORGANISM: human

<400> SEQUENCE: 278

Ser Ser Phe Thr Ser Arg Ile Pro Trp Ala Val
1               5                   10

<210> SEQ ID NO 279
<211> LENGTH: 11
<212> TYPE: PRT
<213> ORGANISM: human

<400> SEQUENCE: 279

Ser Ser Phe Thr Ser Gly Lys Ala Trp Val Ile
1               5                   10

<210> SEQ ID NO 280
<211> LENGTH: 11
<212> TYPE: PRT
<213> ORGANISM: human

<400> SEQUENCE: 280

Ser Ser Phe Thr Ser Ala Glu Ala Trp Ala Pro
1               5                   10

<210> SEQ ID NO 281
<211> LENGTH: 11
<212> TYPE: PRT
<213> ORGANISM: human

<400> SEQUENCE: 281

Ser Ser Phe Thr Ser Gly Asp Arg Phe Asn Leu
1               5                   10

<210> SEQ ID NO 282
<211> LENGTH: 11
<212> TYPE: PRT
<213> ORGANISM: human

<400> SEQUENCE: 282

Ser Ser Phe Thr Ser Tyr Lys Pro His Met Val
1               5                   10

-continued

```
<210> SEQ ID NO 283
<211> LENGTH: 11
<212> TYPE: PRT
<213> ORGANISM: human

<400> SEQUENCE: 283

Ser Ser Phe Thr Ser Gly Ile Gln Phe Asn Leu
1               5                   10

<210> SEQ ID NO 284
<211> LENGTH: 11
<212> TYPE: PRT
<213> ORGANISM: human

<400> SEQUENCE: 284

Ser Ser Phe Thr Ser Ala Ala Arg Phe Ala Leu
1               5                   10

<210> SEQ ID NO 285
<211> LENGTH: 11
<212> TYPE: PRT
<213> ORGANISM: human

<400> SEQUENCE: 285

Ser Ser Phe Thr Ser Gly Ser Arg Phe Val Leu
1               5                   10

<210> SEQ ID NO 286
<211> LENGTH: 11
<212> TYPE: PRT
<213> ORGANISM: human

<400> SEQUENCE: 286

Ser Ser Phe Thr Ser Ser Leu Pro Trp Ala Leu
1               5                   10

<210> SEQ ID NO 287
<211> LENGTH: 11
<212> TYPE: PRT
<213> ORGANISM: human

<400> SEQUENCE: 287

Ser Ser Phe Thr Ser Gly Ile Lys Phe Thr Leu
1               5                   10

<210> SEQ ID NO 288
<211> LENGTH: 11
<212> TYPE: PRT
<213> ORGANISM: human

<400> SEQUENCE: 288

Ser Ser Phe Thr Ser Ala Ile Pro Trp Ser Leu
1               5                   10

<210> SEQ ID NO 289
<211> LENGTH: 11
<212> TYPE: PRT
<213> ORGANISM: human

<400> SEQUENCE: 289

Ser Ser Phe Thr Ser Gly Glu Gln Phe Leu Leu
1               5                   10

<210> SEQ ID NO 290
<211> LENGTH: 11
```

```
<212> TYPE: PRT
<213> ORGANISM: human

<400> SEQUENCE: 290

Ser Ser Phe Thr Ser Gly Pro Arg Trp Asn Leu
1               5                   10

<210> SEQ ID NO 291
<211> LENGTH: 11
<212> TYPE: PRT
<213> ORGANISM: human

<400> SEQUENCE: 291

Ser Ser Phe Thr Ser Gly Ser Thr Phe Asn Leu
1               5                   10

<210> SEQ ID NO 292
<211> LENGTH: 11
<212> TYPE: PRT
<213> ORGANISM: human

<400> SEQUENCE: 292

Ser Ser Phe Thr Ser Gly Arg Arg Phe Val Leu
1               5                   10

<210> SEQ ID NO 293
<211> LENGTH: 11
<212> TYPE: PRT
<213> ORGANISM: human

<400> SEQUENCE: 293

Ser Ser Phe Thr Ser Gly Asn Val Trp Val Leu
1               5                   10

<210> SEQ ID NO 294
<211> LENGTH: 11
<212> TYPE: PRT
<213> ORGANISM: human

<400> SEQUENCE: 294

Ser Ser Phe Thr Ser Ala Pro Ala Phe Val Val
1               5                   10

<210> SEQ ID NO 295
<211> LENGTH: 11
<212> TYPE: PRT
<213> ORGANISM: human

<400> SEQUENCE: 295

Ser Ser Phe Thr Ser Gly Lys Thr Phe Val Leu
1               5                   10

<210> SEQ ID NO 296
<211> LENGTH: 11
<212> TYPE: PRT
<213> ORGANISM: human

<400> SEQUENCE: 296

Ser Ser Phe Thr Ser Asn Ile Pro Trp Ala Ile
1               5                   10

<210> SEQ ID NO 297
<211> LENGTH: 11
<212> TYPE: PRT
<213> ORGANISM: human
```

-continued

```
<400> SEQUENCE: 297

Ser Ser Phe Thr Ser Ser Ala His Phe Val Leu
1               5                   10

<210> SEQ ID NO 298
<211> LENGTH: 11
<212> TYPE: PRT
<213> ORGANISM: human

<400> SEQUENCE: 298

Ser Ser Phe Thr Ser Gly Pro Val Phe Asn Ile
1               5                   10

<210> SEQ ID NO 299
<211> LENGTH: 11
<212> TYPE: PRT
<213> ORGANISM: human

<400> SEQUENCE: 299

Ser Ser Phe Thr Ser Asp Arg Ala Phe Asn Leu
1               5                   10

<210> SEQ ID NO 300
<211> LENGTH: 11
<212> TYPE: PRT
<213> ORGANISM: human

<400> SEQUENCE: 300

Ser Ser Phe Thr Ser Glu Trp Leu Trp Val Leu
1               5                   10

<210> SEQ ID NO 301
<211> LENGTH: 11
<212> TYPE: PRT
<213> ORGANISM: human

<400> SEQUENCE: 301

Ser Ser Phe Thr Ser Gln Pro Arg Trp Ala Pro
1               5                   10

<210> SEQ ID NO 302
<211> LENGTH: 11
<212> TYPE: PRT
<213> ORGANISM: human

<400> SEQUENCE: 302

Ser Ser Phe Thr Ser Gly Ile Arg Phe Asn Leu
1               5                   10

<210> SEQ ID NO 303
<211> LENGTH: 11
<212> TYPE: PRT
<213> ORGANISM: human

<400> SEQUENCE: 303

Ser Ser Phe Thr Ser Gly Arg Ala Phe Asn Leu
1               5                   10

<210> SEQ ID NO 304
<211> LENGTH: 11
<212> TYPE: PRT
<213> ORGANISM: human

<400> SEQUENCE: 304
```

Ser Ser Phe Thr Ser Gly Pro Val Phe Asn Leu
1               5                   10

<210> SEQ ID NO 305
<211> LENGTH: 11
<212> TYPE: PRT
<213> ORGANISM: human

<400> SEQUENCE: 305

Ser Ser Phe Thr Ser Gly Gln Gln Trp Val Leu
1               5                   10

<210> SEQ ID NO 306
<211> LENGTH: 11
<212> TYPE: PRT
<213> ORGANISM: human

<400> SEQUENCE: 306

Ser Ser Phe Thr Ser Gly Ile Arg Phe Asn Val
1               5                   10

<210> SEQ ID NO 307
<211> LENGTH: 11
<212> TYPE: PRT
<213> ORGANISM: human

<400> SEQUENCE: 307

Ser Ser Phe Thr Ser Gly Val Thr Trp Leu Leu
1               5                   10

<210> SEQ ID NO 308
<211> LENGTH: 11
<212> TYPE: PRT
<213> ORGANISM: human

<400> SEQUENCE: 308

Ser Ser Phe Thr Ser Gly Arg Ile Phe Asn Leu
1               5                   10

<210> SEQ ID NO 309
<211> LENGTH: 11
<212> TYPE: PRT
<213> ORGANISM: human

<400> SEQUENCE: 309

Ser Ser Phe Thr Ser Gly Ile Pro Trp Ile Val
1               5                   10

<210> SEQ ID NO 310
<211> LENGTH: 11
<212> TYPE: PRT
<213> ORGANISM: human

<400> SEQUENCE: 310

Thr Ser Tyr Thr Leu Gly Ser Thr Phe Met Leu
1               5                   10

<210> SEQ ID NO 311
<211> LENGTH: 11
<212> TYPE: PRT
<213> ORGANISM: human

<400> SEQUENCE: 311

Thr Ser Tyr Thr His Gly Ser Thr Phe Met Leu

```
1               5                  10
```

<210> SEQ ID NO 312
<211> LENGTH: 11
<212> TYPE: PRT
<213> ORGANISM: human

<400> SEQUENCE: 312

```
Ser Ser Phe Thr Ser Gly Tyr Ala Trp Leu Leu
1               5                  10
```

<210> SEQ ID NO 313
<211> LENGTH: 11
<212> TYPE: PRT
<213> ORGANISM: human

<400> SEQUENCE: 313

```
Thr Ser Tyr Val Met Gly Ser Thr Phe Met Leu
1               5                  10
```

<210> SEQ ID NO 314
<211> LENGTH: 11
<212> TYPE: PRT
<213> ORGANISM: human

<400> SEQUENCE: 314

```
Ser Ser Phe Thr Ser Gly Ser Thr Phe Thr Leu
1               5                  10
```

<210> SEQ ID NO 315
<211> LENGTH: 11
<212> TYPE: PRT
<213> ORGANISM: human

<400> SEQUENCE: 315

```
Thr Ser Phe Thr Ser Gly Ser Thr Phe Met Leu
1               5                  10
```

<210> SEQ ID NO 316
<211> LENGTH: 11
<212> TYPE: PRT
<213> ORGANISM: human

<400> SEQUENCE: 316

```
Thr Ser Ser Thr Leu Gly Ser Thr Phe Met Leu
1               5                  10
```

<210> SEQ ID NO 317
<211> LENGTH: 11
<212> TYPE: PRT
<213> ORGANISM: human

<400> SEQUENCE: 317

```
Thr Arg Tyr Val Met Gly Ser Thr Phe Met Leu
1               5                  10
```

<210> SEQ ID NO 318
<211> LENGTH: 11
<212> TYPE: PRT
<213> ORGANISM: human

<400> SEQUENCE: 318

```
Thr Ser Tyr Arg Glu Gly Ser Thr Phe Met Leu
1               5                  10
```

<210> SEQ ID NO 319
<211> LENGTH: 11
<212> TYPE: PRT
<213> ORGANISM: human

<400> SEQUENCE: 319

Ala Ser Tyr Gln Ala Ser Ser Thr Phe Met Leu
1               5                   10

<210> SEQ ID NO 320
<211> LENGTH: 117
<212> TYPE: PRT
<213> ORGANISM: human

<400> SEQUENCE: 320

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Trp Gly Asp Gly Thr Leu Asn Pro Trp Gly Gln Gly Thr Met
            100                 105                 110

Val Thr Val Ser Ser
        115

<210> SEQ ID NO 321
<211> LENGTH: 117
<212> TYPE: PRT
<213> ORGANISM: human

<400> SEQUENCE: 321

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Thr Asn Ser Ala Lys Phe Asp Pro Trp Gly Gln Gly Thr Met
            100                 105                 110

Val Thr Val Ser Ser
        115

<210> SEQ ID NO 322
<211> LENGTH: 117
<212> TYPE: PRT

<213> ORGANISM: human

<400> SEQUENCE: 322

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asn Glu Arg Pro Ser Phe Asp Pro Trp Gly Gln Gly Thr Met
            100                 105                 110

Val Thr Val Ser Ser
        115

<210> SEQ ID NO 323
<211> LENGTH: 117
<212> TYPE: PRT
<213> ORGANISM: human

<400> SEQUENCE: 323

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Thr Asn Ser Ala Lys Phe Asp Pro Trp Gly Gln Gly Thr Met
            100                 105                 110

Val Thr Val Ser Ser
        115

<210> SEQ ID NO 324
<211> LENGTH: 117
<212> TYPE: PRT
<213> ORGANISM: human

<400> SEQUENCE: 324

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
             85                  90                  95

Ala Lys Thr Gly Tyr Pro Ser Phe Asp Pro Trp Gly Gln Gly Thr Met
            100                 105                 110

Val Thr Val Ser Ser
        115

<210> SEQ ID NO 325
<211> LENGTH: 117
<212> TYPE: PRT
<213> ORGANISM: human

<400> SEQUENCE: 325

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Ala Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
             85                  90                  95

Ala Lys Trp Gly Thr Gly Thr Leu Trp Pro Trp Gly Gln Gly Thr Met
            100                 105                 110

Val Thr Val Ser Ser
        115

<210> SEQ ID NO 326
<211> LENGTH: 111
<212> TYPE: PRT
<213> ORGANISM: human

<400> SEQUENCE: 326

Gln Ser Ala Leu Thr Gln Pro Ala Ser Val Ser Gly Ser Pro Gly Gln
  1               5                  10                  15

Ser Ile Thr Ile Ser Cys Thr Gly Thr Ser Asn Asp Val Gly Ala Tyr
             20                  25                  30

Asn Tyr Val Ser Trp Tyr Gln Gln His Pro Gly Lys Ala Pro Lys Leu
         35                  40                  45

Met Ile Ser Glu Val Asn Lys Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Phe Thr Ser Gly
             85                  90                  95

Leu Pro Trp Val Val Phe Gly Gly Gly Thr Lys Leu Thr Val Leu
            100                 105                 110

<210> SEQ ID NO 327
<211> LENGTH: 111
<212> TYPE: PRT
<213> ORGANISM: human
```

<400> SEQUENCE: 327

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Asn Asp Val Gly Ala Tyr
            20                  25                  30

Asn Tyr Val Ser Trp Tyr Gln Gln His Pro Gly Lys Ala Pro Lys Leu
        35                  40                  45

Met Ile Ser Glu Val Asn Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Met Gly
                85                  90                  95

Ser Thr Phe Met Leu Phe Gly Gly Gly Thr Lys Leu Thr Val Leu
            100                 105                 110

<210> SEQ ID NO 328
<211> LENGTH: 111
<212> TYPE: PRT
<213> ORGANISM: human

<400> SEQUENCE: 328

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Asn Asp Val Gly Ala Tyr
            20                  25                  30

Asn Tyr Val Ser Trp Tyr Gln Gln His Pro Gly Lys Ala Pro Lys Leu
        35                  40                  45

Met Ile Ser Glu Val Asn Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Thr Ser Tyr Thr Met Gly
                85                  90                  95

Ser Thr Phe Met Leu Phe Gly Gly Gly Thr Lys Leu Thr Val Leu
            100                 105                 110

<210> SEQ ID NO 329
<211> LENGTH: 111
<212> TYPE: PRT
<213> ORGANISM: human

<400> SEQUENCE: 329

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Asn Asp Val Gly Ala Tyr
            20                  25                  30

Asn Tyr Val Ser Trp Tyr Gln Gln His Pro Gly Lys Ala Pro Lys Leu
        35                  40                  45

Met Ile Ser Glu Val Asn Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Thr Ser Tyr Thr Met Gly
                85                  90                  95

```
Ser Thr Phe Met Leu Phe Gly Gly Gly Thr Lys Leu Thr Val Leu
            100                 105                 110
```

<210> SEQ ID NO 330
<211> LENGTH: 111
<212> TYPE: PRT
<213> ORGANISM: human

<400> SEQUENCE: 330

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Asn Asp Val Gly Ala Tyr
            20                  25                  30

Asn Tyr Val Ser Trp Tyr Gln Gln His Pro Gly Lys Ala Pro Lys Leu
        35                  40                  45

Met Ile Ser Glu Val Asn Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Thr Ser Tyr Arg Ala Gly
                85                  90                  95

Ser Thr Phe Met Leu Phe Gly Gly Gly Thr Lys Leu Thr Val Leu
            100                 105                 110
```

<210> SEQ ID NO 331
<211> LENGTH: 111
<212> TYPE: PRT
<213> ORGANISM: human

<400> SEQUENCE: 331

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Asn Asp Val Gly Ala Tyr
            20                  25                  30

Asn Tyr Val Ser Trp Tyr Gln Gln His Pro Gly Lys Ala Pro Lys Leu
        35                  40                  45

Met Ile Ser Glu Val Asn Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Phe Thr Ser Gly
                85                  90                  95

Leu Pro Trp Val Leu Phe Gly Gly Gly Thr Lys Leu Thr Val Leu
            100                 105                 110
```

<210> SEQ ID NO 332
<211> LENGTH: 351
<212> TYPE: DNA
<213> ORGANISM: human

<400> SEQUENCE: 332

```
gaggtgcagc tgttggagtc tgggggaggc ttggtacagc ctggggggtc cctgagactc      60
tcctgtgcag cctctggatt cacctttagc agctatgcca tgagctgggt ccgccaggct     120
ccagggaagg ggctggagtg ggtctcagct attagtggta gtggtggtag cacatactac     180
gcagactccg tgaagggccg gttcaccatc tccagagaca attccaagaa cacgctgtat     240
ctgcaaatga acagcctgag agccgaggac acggccgtgt attactgtgc gaaatgggga     300
```

```
gacgggacct tgaacccgtg gggccaaggg acaatggtca ccgtctcctc a       351
```

<210> SEQ ID NO 333
<211> LENGTH: 351
<212> TYPE: DNA
<213> ORGANISM: human

<400> SEQUENCE: 333

```
gaggtgcagc tgttggagtc tggggggaggc ttggtacagc ctgggggtc cctgagactc    60
tcctgtgcag cctctggatt cacctttagc agctatgcca tgagctgggt ccgccaggct   120
ccagggaagg ggctggagtg ggtctcagct attagtggta gtggtggtag cacatactac   180
gcagactccg tgaagggccg gttcaccatc tccagagaca attccaagaa cacgctgtat   240
ctgcaaatga acagcctgag agccgaggac acggccgtgt attactgtgc gaaaacgaac   300
tccgccaagt tcgacccctg gggccaaggg acaatggtca ccgtctcctc a            351
```

<210> SEQ ID NO 334
<211> LENGTH: 351
<212> TYPE: DNA
<213> ORGANISM: human

<400> SEQUENCE: 334

```
gaggtgcagc tgttggagtc tggggggaggc ttggtacagc ctgggggtc cctgagactc    60
tcctgtgcag cctctggatt cacctttagc agctatgcca tgagctgggt ccgccaggct   120
ccagggaagg ggctggagtg ggtctcagct attagtggta gtggtggtag cacatactac   180
gcagactccg tgaagggccg gttcaccatc tccagagaca attccaagaa cacgctgtat   240
ctgcaaatga acagcctgag agccgaggac acggccgtgt attactgtgc gaaaaacgag   300
aggccgtcgt tcgacccctg gggccaaggg acaatggtca ccgtctcctc a            351
```

<210> SEQ ID NO 335
<211> LENGTH: 351
<212> TYPE: DNA
<213> ORGANISM: human

<400> SEQUENCE: 335

```
gaggtgcagc tgttggagtc tggggggaggc ttggtacagc ctgggggtc cctgagactc    60
tcctgtgcag cctctggatt cacctttagc agctatgcca tgagctgggt ccgccaggct   120
ccagggaagg ggctggagtg ggtctcagct attagtggta gtggtggtag cacatactac   180
gcagactccg tgaagggccg gttcaccatc tccagagaca attccaagaa cacgctgtat   240
ctgcaaatga acagcctgag agccgaggac acggccgtgt attactgtgc gaaatgggga   300
gacgggacct tgaacccgtg gggccaaggg acaatggtca ccgtctcctc a            351
```

<210> SEQ ID NO 336
<211> LENGTH: 351
<212> TYPE: DNA
<213> ORGANISM: human

<400> SEQUENCE: 336

```
gaggtgcagc tgttggagtc tggggggaggc ttggtacagc ctgggggtc cctgagactc    60
tcctgtgcag cctctggatt cacctttagc agctatgcca tgagctgggt ccgccaggct   120
ccagggaagg ggctggagtg ggtctcagct attagtggta gtggtggtag cacatactac   180
gcagactccg tgaagggccg gttcaccatc tccagagaca attccaagaa cacgctgtat   240
ctgcaaatga acagcctgag agccgaggac acggccgtgt attactgtgc gaaaacgggg   300
```

```
tacccctcct tcgacccctg gggccaaggg acaatggtca ccgtctcctc a           351
```

<210> SEQ ID NO 337
<211> LENGTH: 351
<212> TYPE: DNA
<213> ORGANISM: human

<400> SEQUENCE: 337

```
gaggtgcagc tgttggagtc tgggggaggc ttggtacagc ctgggggtc cctgagactc    60
tcctgtgcag cctctggatt cacctttagc agctatgcca tgagctgggt ccgccaggct   120
ccagggaagg ggctggagtg ggtctcagct attagtggta gtggtggtag cacatactac   180
gcagactccg tgaagggccg gttcaccatc tccagagaca attccaagaa cacgctgtat   240
ctgcaaatga acagcctgag agccgaggac acggccgtgt attactgtgc gaaatgggga   300
acggggacct tgtggccctg gggccaaggg acaatggtca ccgtctcctc a           351
```

<210> SEQ ID NO 338
<211> LENGTH: 333
<212> TYPE: DNA
<213> ORGANISM: human

<400> SEQUENCE: 338

```
cagtctgccc tgactcagcc tgcctccgtg tctgggtctc ctggacagtc gatcaccatc    60
tcctgcactg gaaccagtaa tgacgttggt gcttataatt atgtctcctg gtaccaacaa   120
cacccaggca aagcccccaa actcatgatt tctgaggtca ataaacggcc ctcagggggtt   180
tctaatcgct tctctggctc caagtctggc aacacggcct ctctgaccat ctctgggctc   240
caggctgagg acgaggctga ttattactgc agctcattta caagcgggct cccctgggtc   300
gtcttcggcg gagggaccaa gctgaccgtc cta                                333
```

<210> SEQ ID NO 339
<211> LENGTH: 333
<212> TYPE: DNA
<213> ORGANISM: human

<400> SEQUENCE: 339

```
cagtctgccc tgactcagcc tgcctccgtg tctgggtctc ctggacagtc gatcaccatc    60
tcctgcactg gaaccagtaa tgacgttggt gcttataatt atgtctcctg gtaccaacaa   120
cacccaggca aagcccccaa actcatgatt tctgaggtca ataaacggcc ctcagggggtt   180
tctaatcgct tctctggctc caagtctggc aacacggcct ctctgaccat ctctgggctc   240
caggctgagg acgaggctga ttattactgc agcagctaca cgatggggag cacttttatg   300
ctattcggcg gagggaccaa gctgaccgtc cta                                333
```

<210> SEQ ID NO 340
<211> LENGTH: 333
<212> TYPE: DNA
<213> ORGANISM: human

<400> SEQUENCE: 340

```
cagtctgccc tgactcagcc tgcctccgtg tctgggtctc ctggacagtc gatcaccatc    60
tcctgcactg gaaccagtaa tgacgttggt gcttataatt atgtctcctg gtaccaacaa   120
cacccaggca aagcccccaa actcatgatt tctgaggtca ataaacggcc ctcagggggtt   180
tctaatcgct tctctggctc caagtctggc aacacggcct ctctgaccat ctctgggctc   240
```

```
caggctgagg acgaggctga ttattactgc acctcgtaca ccatgggcag cacttttatg    300
ctattcggcg gagggaccaa gctgaccgtc cta                                 333
```

<210> SEQ ID NO 341
<211> LENGTH: 333
<212> TYPE: DNA
<213> ORGANISM: human

<400> SEQUENCE: 341

```
cagtctgccc tgactcagcc tgcctccgtg tctgggtctc ctggacagtc gatcaccatc     60
tcctgcactg gaaccagtaa tgacgttggt gcttataatt atgtctcctg gtaccaacaa    120
cacccaggca aagcccccaa actcatgatt tctgaggtca ataaacggcc ctcagggggtt   180 tctaatcgct tctctggctc caagtctggc aacacggcct ctctgaccat ctctgggctc    240
caggctgagg acgaggctga ttattactgc acctcgtaca ccatgggcag cacttttatg    300
ctattcggcg gagggaccaa gctgaccgtc cta                                 333
```

<210> SEQ ID NO 342
<211> LENGTH: 333
<212> TYPE: DNA
<213> ORGANISM: human

<400> SEQUENCE: 342

```
cagtctgccc tgactcagcc tgcctccgtg tctgggtctc ctggacagtc gatcaccatc     60
tcctgcactg gaaccagtaa tgacgttggt gcttataatt atgtctcctg gtaccaacaa    120
cacccaggca aagcccccaa actcatgatt tctgaggtca ataaacggcc ctcagggggtt   180 tctaatcgct tctctggctc caagtctggc aacacggcct ctctgaccat ctctgggctc    240
caggctgagg acgaggctga ttattactgc acctcgtaca ccatgggcag cacttttatg    300
ctattcggcg gagggaccaa gctgaccgtc cta                                 333
```

<210> SEQ ID NO 343
<211> LENGTH: 333
<212> TYPE: DNA
<213> ORGANISM: human

<400> SEQUENCE: 343

```
cagtctgccc tgactcagcc tgcctccgtg tctgggtctc ctggacagtc gatcaccatc     60
tcctgcactg gaaccagtaa tgacgttggt gcttataatt atgtctcctg gtaccaacaa    120
cacccaggca aagcccccaa actcatgatt tctgaggtca ataaacggcc ctcagggggtt   180 tctaatcgct tctctggctc caagtctggc aacacggcct ctctgaccat ctctgggctc    240
caggctgagg acgaggctga ttattactgc agctcattta caagcgggtt gccgtgggtg    300
ctcttcggcg gagggaccaa gctgaccgtc cta                                 333
```

<210> SEQ ID NO 344
<211> LENGTH: 330
<212> TYPE: PRT
<213> ORGANISM: human

<400> SEQUENCE: 344

```
Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
```

```
                35                  40                  45
Gly Val His Thr Phe Pro Ala Val Leu Gln Ser Ser Gly Leu Tyr Ser
             50                  55                  60
Leu Ser Ser Val Val Thr Val Pro Ser Ser Leu Gly Thr Gln Thr
65                  70                  75                  80
Tyr Ile Cys Asn Val Asn His Lys Pro Ser Asn Thr Lys Val Asp Lys
                 85                  90                  95
Lys Val Glu Pro Lys Ser Cys Asp Lys Thr His Thr Cys Pro Pro Cys
                100                 105                 110
Pro Ala Pro Glu Leu Leu Gly Gly Pro Ser Val Phe Leu Phe Pro Pro
                115                 120                 125
Lys Pro Lys Asp Thr Leu Met Ile Ser Arg Thr Pro Glu Val Thr Cys
            130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
                180                 185                 190
His Gln Asp Trp Leu Asn Gly Lys Glu Tyr Lys Cys Lys Val Ser Asn
            195                 200                 205
Lys Ala Leu Pro Ala Pro Ile Glu Lys Thr Ile Ser Lys Ala Lys Gly
210                 215                 220
Gln Pro Arg Glu Pro Gln Val Tyr Thr Leu Pro Pro Ser Arg Glu Glu
225                 230                 235                 240
Met Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
                260                 265                 270
Asn Tyr Lys Thr Thr Pro Pro Val Leu Asp Ser Asp Gly Ser Phe Phe
            275                 280                 285
Leu Tyr Ser Lys Leu Thr Val Asp Lys Ser Arg Trp Gln Gln Gly Asn
        290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 345
<211> LENGTH: 106
<212> TYPE: PRT
<213> ORGANISM: human

<400> SEQUENCE: 345

Gly Gln Pro Lys Ala Ala Pro Ser Val Thr Leu Phe Pro Pro Ser Ser
1               5                   10                  15
Glu Glu Leu Gln Ala Asn Lys Ala Thr Leu Val Cys Leu Ile Ser Asp
                20                  25                  30
Phe Tyr Pro Gly Ala Val Thr Val Ala Trp Lys Ala Asp Ser Ser Pro
            35                  40                  45
Val Lys Ala Gly Val Glu Thr Thr Thr Pro Ser Lys Gln Ser Asn Asn
        50                  55                  60
Lys Tyr Ala Ala Ser Ser Tyr Leu Ser Leu Thr Pro Glu Gln Trp Lys
65                  70                  75                  80
```

-continued

```
Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 346
<211> LENGTH: 19
<212> TYPE: PRT
<213> ORGANISM: human

<400> SEQUENCE: 346

Met Glu Trp Ser Trp Val Phe Leu Phe Phe Leu Ser Val Thr Thr Gly
1               5                   10                  15

Val His Ser

<210> SEQ ID NO 347
<211> LENGTH: 20
<212> TYPE: PRT
<213> ORGANISM: human

<400> SEQUENCE: 347

Met Ser Val Pro Thr Gln Val Leu Gly Leu Leu Leu Leu Trp Leu Thr
1               5                   10                  15

Asp Ala Arg Cys
            20
```

P-CADHERIN ANTIBODIES

This application is a continuation of U.S. application Ser. No. 12/249,843, now U.S. Pat. No. 7,928,214, filed Oct. 10, 2008 which is a continuation of U.S. application Ser. No. 11/410,610, now U.S. Pat. No. 7,452,537, filed Apr. 25, 2006, which claims priority to U.S. Provisional Application No. 60/675,311 filed on Apr. 26, 2005, which is incorporated herein by reference in its entirety.

REFERENCE TO SEQUENCE LISTING

This application is being filed electronically via EFS-Web and includes an electronically submitted sequence listing in .txt format. The .txt file contains a sequence listing entitled "PC32778C_SequenceListing.txt" created on Apr. 1, 2011 and having a size of 99 KB. The sequence listing contained in this .txt file is part of the specification and is herein incorporated by reference in its entirety.

FIELD OF THE INVENTION

The present invention relates to antibodies and antigen-binding portions thereof that bind to P-cadherin. The invention also relates to nucleic acid molecules encoding such antibodies and antigen-binding portions, methods of making P-cadherin antibodies and antigen-binding portions, compositions comprising these antibodies and antigen-binding portions and methods of using the antibodies, antigen-binding portions, and compositions.

BACKGROUND OF THE INVENTION

Cadherins are a superfamily of transmembrane glycoproteins that regulate cell-cell adhesion during development and tissue homeostasis (Gumbiner *J. Cell. Biol.*, 148:399-404 (2000); Yagi, et al., *Genes Dev.*, 14:1169-1180 (2000)). The intracellular domains of cadherins interact with cytoplasmic proteins such as catenins and p120, which form the basis of cadherin attachment to the actin cytoskeleton. Cadherins have five extracellular $Ca^{2+}$ binding domains and a small cytoplasmic domain that is highly conserved among the classical cadherins. Members of the classical cadherin family include P-cadherin, E-cadherin, and N-cadherin. Cellular adhesion molecules such as cadherins are considered to play a significant role in the cellular connections of cancer and metastatic cells (Furukawa, et al., *Microscopy Res. Technique* 38 (4):343-352 (1997)). P-cadherin expression in normal adult tissues is low and is restricted primarily to myoepithelial cells and the basal layers of stratified epithelium (Shimoyama, et al. *Cancer Res.* 49:2128-33 (1989)). P-cadherin is upregulated in inflammatory bowel diseases such as Crohn's disease and colitis (Hardy, et al., *Gut* 50:513-519 (2002)). A large body of evidence now also reveals that aberrant P-cadherin expression is associated with cell proliferation and with tumors of the colon, breast, lung, thyroid, and cervix (Gamallo, *Modern Pathology*, 14:650-654, (2001); and Stefansson, et al., *J. Clin. Oncol.* 22(7):1242-1252 (2004)). Human P-cadherin was reported to be the antigen recognized by the NCC-CAD-299 monoclonal antibody raised against a vulvar epidermoid carcinoma (Shimoyama, et al., *Cancer Res.*, 49:2128-2133 (1989)). Modulation of P-cadherin mediated adhesion and intracellular signaling is expected to result in decreased proliferation and survival of tumor cells in vivo. Accordingly, in view of the pivotal role that P-cadherin appears to possess in cell proliferation and solid tumor progression, it is desirable to generate antibodies to P-cadherin that can provide a therapeutic benefit to patients with a variety of cancers.

SUMMARY OF THE INVENTION

In one aspect of the present invention is a P-cadherin antibody or antigen-binding portion thereof wherein the antibody or antigen-binding portion thereof has at least one of several functional properties as described below in A) thru K).

A) For example, in one embodiment the antibodies or antigen-binding portions thereof have a greater binding affinity for P-cadherin ($K_D(P)$) than for E-cadherin ($K_D(E)$). In one embodiment, the antibodies or antigen-binding portions thereof of the present invention have a $K_D(E)/K_D(P)$ that is greater than or equal to 1.5. In a further embodiment the antibodies or antigen-binding portions thereof of the present invention have a $K_D(E)/K_D(P)$ that is greater than or equal 2, greater than or equal to 3, greater than or equal to 5, greater than or equal to 10, greater than or equal to 20, greater than or equal to 50, greater than or equal to 100, greater than or equal to 200, greater than or equal to 500, or greater than or equal to 1000. Typically there is no upper limit on the value of $K_D(E)/K_D(P)$ because the $K_D(E)$ value can be very small, such as 0. For practical purposes, however, an upper limit of $K_D(E)/K_D(P)$ can be $1 \times 10^6$. Such $K_D$ values for both P-cadherin and for E-cadherin can be measured by any technique known to those of skill in the art, such as by ELISA, RIA, flow cytometry, or surface plasmon resonance, such as BIACORE™.

B) In another embodiment, the antibody or portion thereof binds to P-cadherin with a $K_D$ of 1000 nM or less as measured by surface plasmon resonance. In a further embodiment, the antibody or portion binds to P-cadherin with a $K_D$ of less than 500 nM, less than 100 nM, less than 50 nM, less than 20 nM, less than 10 nM, less than 1 nM, less than 500 pM, or less than 100 pM, as measured by surface plasmon resonance. Typically, there is no lower limit on the value of $K_D$. For practical purposes, however, the lower limit can be assumed to be about 1 pM.

C) In another embodiment, the antibody or portion thereof has an off rate ($k_{off}$) for P-cadherin of less than or equal to $0.01^{s-1}$ as measured by surface plasmon resonance. For example, in certain embodiments the antibody or portion has a $k_{off}$ for P-cadherin of less than $0.005^{s-1}$, less than $0.004^{s-1}$, less than $0.003^{s-1}$, less than $0.002^{s-1}$, or less than $0.001^{s-1}$. Typically, there is no lower limit for the value of $k_{off}$. For practical purposes, however, the lower limit can be assumed to be about $1 \times 10^{-7\ s-1}$.

D) In another embodiment, the P-cadherin antibody or portion thereof has an $IC_{50}$ of 100 nM or less as measured by a P-cadherin dependent cell adhesion assay. In a further embodiment, said $IC_{50}$ is less than 50 nM, less than 40 nM, less than 20 nM, less than 10 nM, less than 1 nM, less than 500 pM, less than 200 pM, less than 100 pM, or less than 10 pM, as measured by a P-cadherin dependent cell adhesion assay. Typically, there is no lower limit for the value of $IC_{50}$ as measured by a P-cadherin dependent cell adhesion assay. For practical purposes, however, the lower limit can be assumed to be about 1 pM.

E) In another embodiment, the P-cadherin antibody or portion thereof has an $IC_{50}$ of 100 nM or less as measured by a P-cadherin dependent cell aggregation assay. In a further embodiment, said $IC_{50}$ is less than 50 nM, less than 40 nM, less than 20 nM, less than 10 nM, less than 1 nM, less than 500 pM, less than 200 pM, less than 100 pM, or less than 1 pM, as measured by a P-cadherin dependent cell aggregation assay. Typically, there is no lower limit for the value of $IC_{50}$ as measured by a P-cadherin dependent cell aggregation assay. For practical purposes, however, the lower limit can be assumed to be about 1 pM.

F) In another embodiment, the P-cadherin antibody or portion thereof increases spheroid disruption in a P-cadherin-dependent spheroid disruption assay by a factor of at least 2 as compared to a control sample with no IgG present. In a further embodiment, the P-cadherin antibody or portion thereof increases spheroid disruption in a P-cadherin-dependent spheroid disruption assay by a factor of at least 3, at least 4, at least 6, at least 10, or at least 15 as compared to a control sample with no IgG present.

G) In another embodiment, the P-cadherin antibody or portion thereof competes for binding to P-cadherin with an antibody selected from the group consisting of 194-e06; 194-a02; 194-b09; 195-e11; 194-g09; 196-h02; 194-e01; 196-d10; 196-g03; 196-e06; 195-a09; 198-a09; 200-h06; g-194-b09; g-194-g09; g-196-g03; g-196-h02; g-194-e01; g-194-e06; 129-1c4; and g-129-1c4.

H) In another embodiment, the P-cadherin antibody or portion thereof cross-competes for binding to P-cadherin with an antibody selected from the group consisting of 194-e06; 194-a02; 194-b09; 195-e11; 194-g09; 196-h02; 194-e01; 196-d10; 196-g03; 196-e06; 195-a09; 198-a09; 200-h06; g-194-b09; g-194-g09; g-196-g03; g-196-h02; g-194-e01; g-194-e06129-1c4; and g-129-1c4.

I) In another embodiment, the P-cadherin antibody or portion thereof binds to the same epitope of P-cadherin as an antibody selected from the group consisting of 194-e06; 194-a02; 194-b09; 195-e11; 194-g09; 196-h02; 194-e01; 196-d10; 196-g03; 196-e06; 195-a09; 198-a09; 200-h06; g-194-b09; g-194-g09; g-196-g03; g-196-h02; g-194-e01; g-194-e06; 129-1c4; and g-129-1c4.

J) In another embodiment, the P-cadherin antibody or portion thereof binds to P-cadherin with substantially the same $K_D$ as an antibody selected from the group consisting of 194-e06; 194-a02; 194-b09; 195-e11; 194-g09; 196-h02; 194-e01; 196-d10; 196-g03; 196-e06; 195-a09; 198-a09; 200-h06; g-194-b09; g-194-g09; g-196-g03; g-196-h02; g-194-e01; g-194-e06; 129-1c4; and g-129-1c4.

K) In another embodiment, the P-cadherin antibody or portion thereof binds to P-cadherin with substantially the same $k_{off}$ as an antibody selected from the group consisting of 194-e06; 194-a02; 194-b09; 195-e11; 194-g09; 196-h02; 194-e01; 196-d10; 196-g03; 196-e06; 195-a09; 198-a09; 200-h06; g-194-b09; g-194-g09; g-196-g03; g-196-h02; g-194-e01; g-194-e06; 129-1c4; and g-129-1c4.

A further aspect of the present invention is an antibody or antigen-binding portion thereof with at least one of the functional properties described previously in A) thru K), comprising a $V_H$ domain that is at least 90% identical in amino acid sequence to any one of SEQ ID NOs: 1 to 13 and 320 to 325. In one embodiment, said $V_H$ domain is at least 91%, at least 93%, at least 95%, at least 97%, at least 99%, or 100% identical in amino acid sequence to any one of SEQ ID NOs: 1 to 12 and 320 to 325.

In a further embodiment, the antibody or portion thereof has at least one of the functional properties described previously in A) thru K), comprising a $V_H$ domain that is any one of SEQ ID NOs: 1 to 13 and 320 to 325, or differs from any one of SEQ ID Nos: 1 to 13 and 320 to 325 by having at least one conservative amino acid substitution. For example, the $V_H$ domain can differ by 1, 2, 3, 4, 5, 6, 7, 8, 9, or 10 conversative amino acid substitutions from any one of SEQ ID NOs: 1 to 13 and 320 to 325. In a further embodiment, any of these conservative amino acid substitutions can occur in the CDR1, CDR2, and/or CDR3 regions.

A further aspect of the present invention is an antibody or antigen-binding portion thereof with at least one of the functional properties described previously in A) thru K), comprising a $V_L$ domain that is at least 90% identical in amino acid sequence to any one of SEQ ID NOs: 14 to 23 and 326 to 331. In one embodiment, said $V_L$ domain is at least 91%, at least 93%, at least 95%, at least 97%, at least 99%, or 100% identical in amino acid sequence to any one of SEQ ID NOs: 14 to 23 and 326 to 331.

In a further embodiment, the antibody or portion thereof has at least one of the functional properties described previously in A) thru K), and comprises a $V_L$ domain that is any one of SEQ ID NOs: 14 to 23 and 326 to 331, or differs from any one of SEQ ID Nos: 14 to 23 and 326 to 331 by having at least one conservative amino acid substitution. For example, the $V_L$ domain can differ by 1, 2, 3, 4, 5, 6, 7, 8, 9, or 10 conversative amino acid substitutions from any one of SEQ ID NOs: 14 to 23 and 326 to 331. In a further embodiment, any of these conservative amino acid substitutions can occur in the CDR1, CDR2, and/or CDR3 regions.

Another aspect of the present invention is an antibody or antigen-binding portion thereof with at least one of the functional properties described previously in A) thru K), wherein the $V_L$ and $V_H$ domains are each at least 90% identical in amino acid sequence to the $V_L$ and $V_H$ domains, respectively, of any one of antibodies 194-e06; 194-a02; 194-b09; 195-e11; 194-g09; 196-h02; 194-e01; 196-d10; 196-g03; 196-e06; 195-a09; 198-a09; 200-h06; g-194-b09; g-194-g09; g-196-g03; g-196-h02; g-194-e01; g-194-e06; 129-1c4; and g-129-1c4. For example, the $V_L$ and $V_H$ domains are each at least 91%, 93%, 95%, 97%, 99% or 100% identical in amino acid sequences to the $V_L$ and $V_H$ domains, respectively, of any one of antibodies 194-e06; 194-a02; 194-b09; 195-e11; 194-g09; 196-h02; 194-e01; 196-d10; 196-g03; 196-e06; 195-a09; 198-a09; 200-h06; g-194-b09; g-194-g09; g-196-g03; g-196-h02; g-194-e01; g-194-e06; 129-1c4; and g-129-1c4.

In another aspect of the present invention is an antibody or antigen-binding portion thereof that is selected from the group consisting of: a) an antibody or portion thereof that comprises a $V_H$ domain as set forth in SEQ ID NO: 1, and a $V_L$ domain as set forth in SEQ ID NO: 14; b) an antibody or portion thereof that comprises a $V_H$ domain as set forth in SEQ ID NO: 2, and a $V_L$ domain as set forth in SEQ ID NO: 14; c) an antibody or portion thereof that comprises a $V_H$ domain as set forth in SEQ ID NO: 2 and a $V_L$ domain as set forth in SEQ ID NO: 15; d) an antibody or portion thereof that comprises a $V_H$ domain as set forth in SEQ ID NO: 3, and a $V_L$ domain as set forth in SEQ ID NO: 16; e) an antibody or portion thereof that comprises a $V_H$ domain as set forth in SEQ ID NO: 4 and a $V_L$ domain as set forth in SEQ ID NO: 17; f) an antibody or portion thereof that comprises a $V_H$ domain as set forth in SEQ ID NO: 4 and a $V_L$ domain as set forth in SEQ ID NO: 23; g) an antibody or portion thereof that comprises a $V_H$ domain as set forth in SEQ ID NO: 5 and a $V_L$ domain as set forth in SEQ ID NO: 18; h) an antibody or portion thereof that comprises a $V_H$ domain as set forth in SEQ ID NO: 6 and a $V_L$ domain as set forth in SEQ ID NO: 23; i) an antibody or portion thereof that comprises a $V_H$ domain as set forth in SEQ ID NO: 7 and a $V_L$ domain as set forth in SEQ ID NO: 23; j) an antibody or portion thereof that comprises a $V_H$ domain as set forth in SEQ ID NO: 8 and a $V_L$ domain as set forth in SEQ ID NO: 23; k) an antibody or portion thereof that comprises a $V_H$ domain as set forth in SEQ ID NO: 9 and a $V_L$ domain as set forth in SEQ ID NO: 23; l) an antibody or portion thereof that comprises a $V_H$ domain as set forth in SEQ ID NO: 10 and a $V_L$ domain as set forth in SEQ ID NO: 19; m) an antibody or portion thereof that comprises a V$_H$ domain as set forth in SEQ ID NO: 11 and a V$_L$ domain as set forth in SEQ ID NO: 20; n) an antibody or portion thereof that comprises a V$_H$ domain as set forth in SEQ ID NO: 12 and a V$_L$ domain as set forth in SEQ ID NO: 21; o) an antibody or portion thereof that comprises a V$_H$ domain as set forth in SEQ ID NO: 13 and a V$_L$ domain as set forth in SEQ ID NO: 22; p) an antibody or portion thereof that comprises a V$_H$ domain as set forth in SEQ ID NO: 320 and a V$_L$ domain as set forth in SEQ ID NO: 326; q) an antibody or antigen-binding portion thereof that comprises a V$_H$ domain as set forth in SEQ ID NO: 321 and a V$_L$ domain as set forth in SEQ ID NO: 327; r) an antibody or portion thereof that comprises a V$_H$ domain as set forth in SEQ ID NO: 322 and a V$_L$ domain as set forth in SEQ ID NO: 328; s) an antibody or portion thereof that comprises a V$_H$ domain as set forth in SEQ ID NO: 323 and a V$_L$ domain as set forth in SEQ ID NO: 329; t) an antibody or portion thereof that comprises a V$_H$ domain as set forth in SEQ ID NO: 324 and a V$_L$ domain as set forth in SEQ ID NO: 330; and u) an antibody or portion thereof that comprises a V$_H$ domain as set forth in SEQ ID NO: 325, and a V$_L$ domain as set forth in SEQ ID NO: 331.

In a further embodiment, for any of the antibodies or portions thereof as described above in groups a) to u) the V$_H$ and/or V$_L$ domains can differ from the specific SEQ ID NOs recited therein by at least one conservative amino acid substitution. For example, the V$_H$ and/or V$_L$ domains can differ from the recited SEQ ID NO by 1, 2, 3, 4, 5, 6, 7, 8, 9, or 10 conservative amino acid substitutions. In a further embodiment, any of these conservative amino acid substitutions can occur in the CDR1, CDR2, and/or CDR3 regions.

In another embodiment, the present invention provides an antibody or antigen-binding portion thereof with at least one of the functional properties described previously in A) thru K), comprising a V$_H$ domain that is independently selected from any one of SEQ ID NOs: 1 to 13 and 320 to 325, or a sequence that differs from any one of SEQ ID NOs: 1 to 13 and 320 to 325 by at least one conservative amino acid substitution, and further comprises a V$_L$ domain that is independently selected from any one of SEQ ID NOs: 14 to 23 and 326 to 331, or a sequence that differs from any one of SEQ ID NOs: 14 to 23 and 326 to 331 by at least one conservative amino acid substitution. For example, the V$_H$ and V$_L$ domains can each independently differ from any one of SEQ ID NOs: 1 to 13, 320 to 325, 14 to 23, and 326 to 331 by 1, 2, 3, 4, 5, 6, 7, 8, 9, or 10 conservative amino acid substitutions.

In a further embodiment, the present invention provides an antibody or antigen-binding portion thereof with at least one of the functional properties described previously in A) thru K), wherein said antibody or portion comprises a V$_H$ CDR3 selected from any one of SEQ ID NOs: 26 to 37 and 91 to 256, or a sequence that differs from any one of SEQ ID NOs: 26 to 37 and 91 to 256 by at least one conservative amino acid substitution. For example, the V$_H$ CDR3 can differ from any one of SEQ ID NOs: 26 to 37 and 91 to 256 by 1, 2, 3, or 4 conservative amino acid substitutions.

In a further embodiment, the present invention provides an antibody or antigen-binding portion thereof with at least one of the functional properties described previously in A) thru K), wherein said antibody or antigen-binding portion comprises a V$_L$ CDR3 selected from any one of SEQ ID NOs: 40 to 47 and 257 to 319, or a sequence that differs from any one of SEQ ID NOs: 40 to 47 and 257 to 319 by at least one conservative amino acid substitution. For example, the V$_L$ CDR3 can differ from any one of SEQ ID NOs: 40 to 47 and 257 to 319 by 1, 2, 3, 4, or 5 conservative amino acid substitutions.

In a further embodiment, the present invention provides an antibody or antigen-binding portion thereof, wherein said antibody or antigen-binding portion comprises: a V$_H$ CDR1 as set forth in SEQ ID NO: 24, or a sequence that differs from SEQ ID NO: 24 by at least one conservative amino acid substitution; a V$_H$ CDR2 as set forth in SEQ ID NO: 25 or a sequence that differs from SEQ ID NO: 25 by at least one conservative amino acid substitution; and a V$_H$ CDR3 that is independently selected from any one of SEQ ID NOs: 26 to 37 and 91 to 256, or a sequence that differs from any one of SEQ ID NOs: 26 to 37 and 91 to 256 by at least one conservative amino acid substitution. For example, the V$_H$ CDR1, CDR2, and CDR3 sequences mentioned above can each independently differ from the respective recited SEQ ID NOs by 1, 2, 3, 4 or 5 conservative amino acid substitutions.

In another embodiment, the present invention provides an antibody or antigen-binding portion thereof, wherein said antibody or antigen-binding portion comprises: a V$_L$ CDR1 as set forth in SEQ ID NO: 38, or a sequence that differs from SEQ ID NO: 38 by at least one conservative amino acid substitution; a V$_L$ CDR2 as set forth in SEQ ID NO: 39, or a sequence that differs from SEQ ID NO: 39 by at least one conservative amino acid substitution; and a V$_L$ CDR3 that is independently selected from any one of SEQ ID NOs: 40 to 47 and 257 to 319, or a sequence that differs from any one of SEQ ID NOs: 40 to 47 and 257 to 319 by at least one conservative amino acid substitution. For example, the V$_L$ CDR1, CDR2, and CDR3 sequences mentioned above can each independently differ from the respective recited SEQ ID NOs by 1, 2, 3, 4 or 5 conservative amino acid substitutions.

The present invention further provides an antibody or antigen-binding portion thereof, wherein said antibody or antigen-binding portion comprises: a V$_H$ CDR1 as set forth in SEQ ID NO: 24; a V$_H$ CDR2 as set forth in SEQ ID NO: 25; a V$_H$ CDR3 selected from any one of SEQ ID NOs: 26 to 37 and 91 to 256; a V$_L$ CDR1 as set forth in SEQ ID NO: 38; a V$_L$ CDR2 as set forth in SEQ ID NO: 39; and a V$_L$ CDR3 selected from any one of SEQ ID NOs: 40 to 47 and 257 to 319. In a further embodiment, the V$_H$ and V$_L$ CDR1, CDR2, and CDR3 sequences mentioned can also each independently differ from the specific SEQ ID NOs recited above by at least one conservative amino acid substitution. For example, the CDR1, CDR2, and CDR3 sequences can each independently differ by 1, 2, 3, 4, or 5 conservative amino acid substitutions from the respective specific SEQ ID NOs recited above.

The present invention further provides an antibody or antigen-binding portion thereof wherein said antibody or antigen-binding portion comprises the V$_H$ and V$_L$ CDR1, the V$_H$ and V$_L$ CDR2, and the V$_H$ and V$_L$ CDR3 as found in any of antibodies 194-e06; 194-a02; 194-b09; 195-e11; 194-g09; 196-h02; 194-e01; 196-d10; 196-g03; 196-e06; 195-a09; 198-a09; 200-h06; g-194-b09; g-194-g09; g-196-g03; g-196-h02; g-194-e01; g-194-e06; 129-1c4; and g129-1c4.

The present invention further provides an antibody or antigen-binding portion thereof, comprising a V$_H$ domain selected from any one of SEQ ID NOs: 1 to 13 and 320 to 325, or differs from any one of SEQ ID NOs: 1 to 13 and 320 to 325 by 1 to 10 conservative amino acid substitutions.

The present invention further provides an antibody or antigen-binding portion thereof, comprising a V$_L$ domain selected from any one of SEQ ID NOs: 14 to 23 and 326 to 331, or differs from any one of SEQ ID NOs: 14 to 23 and 326 to 331 by 1 to 10 conservative amino acid substitutions.

The present invention further provides an antibody or antigen-binding portion thereof, comprising a V$_H$ domain that is independently selected from any one of SEQ ID NOs: 1 to 13 and 320 to 325, or a sequence that differs from any one of SEQ ID NOs: 1 to 13 and 320 to 325 by 1 to 10 conservative amino acid substitutions, and further comprising a $V_L$ domain that is independently selected from any one of SEQ ID NOs: 14 to 23 and 326 to 331, or a sequence that differs from any one of SEQ ID NOs: 14 to 23 and 326 to 331 by 1 to 10 conservative amino acid substitutions.

The present invention further provides an antibody or antigen-binding portion thereof, wherein said antibody or antigen-binding portion comprises: a $V_H$ CDR1 as set forth in SEQ ID NO: 24, or a sequence that differs from SEQ ID NO: 24 by 1 to 4 conservative amino acid substitutions; a $V_H$ CDR2 as set forth in SEQ ID NO: 25, or a sequence that differs from SEQ ID NO: 25 by 1 to 4 conservative amino acid substitutions; and a $V_H$ CDR3 that is selected from any one of SEQ ID NOs: 26 to 37 and 91 to 256, or a sequence that differs from any one of SEQ ID NOs: 26 to 37 and 91 to 256 by 1 to 4 conservative amino acid substitutions.

The present invention further provides an antibody or antigen-binding portion thereof, wherein said antibody or antigen-binding portion comprises: a $V_L$ CDR1 as set forth in SEQ ID NO: 38, or a sequence that differs from SEQ ID NO: 38 by 1 to 4 conservative amino acid substitutions; a $V_L$ CDR2 as set forth in SEQ ID NO: 39, or a sequence that differs from SEQ ID NO: 39 by 1 to 4 conservative amino acid substitutions; and a $V_L$ CDR3 that is selected from any one of SEQ ID NOs: 40 to 47 and 257 to 319, or a sequence that differs from any one of SEQ ID NOs: 40 to 47 and 257 to 319 by 1 to 4 conservative amino acid substitutions.

The present invention further provides an antibody or antigen-binding portion thereof with at least one of the functional properties described previously in A) thru K), wherein said antibody or antigen-binding portion comprises: a $V_H$ FR1 as set forth in SEQ ID NO: 48; a $V_H$ FR2 as set forth in SEQ ID NO: 49; a $V_H$ FR3 selected from any one of SEQ ID NOs: 50 to 55; a $V_H$ FR4 selected from any one of SEQ ID NOs: 56 and 57; a $V_L$ FR1 selected from any one of SEQ ID NOs: 58 and 59; a $V_L$ FR2 selected from any one of SEQ ID NOs: 60 to 62; a $V_L$ FR3 selected from any one of SEQ ID NOs: 63 to 66; and a $V_L$ FR4 as set forth in SEQ ID NO: 67. In a further embodiment, the $V_H$ and $V_L$ FR1, FR2, FR3, and FR4 sequences mentioned can also each independently differ from the specific SEQ ID NOs. recited above by at least one conservative amino acid substitution. For example, the FR1, FR2, FR3, and FR4 sequences can each independently differ by 1, 2, 3, 4, 5, 6, 7, 8, 9, or 10 conservative amino acid substitutions from the respective specific SEQ ID NOs recited above. In a still further embodiment, any of the FR1, FR2, FR3, and FR4 sequences can each independently be mutated to match the respective germline framework sequence.

In a further embodiment of the present invention is any of the antibodies described herein wherein the antibody is an IgG, an IgM, an IgE, an IgA, or an IgD molecule, or is derived therefrom. For example, the antibody can be an $IgG_1$ or $IgG_2$. For example, in one embodiment IgG is an $IgG_1$ wherein the heavy chain constant region comprises SEQ ID NO: 344 and wherein the light chain constant region comprises SEQ ID NO: 345, with the proviso that the C-terminal lysine residue of SEQ ID NO: 344 is optionally cleaved.

Another embodiment provides any of the antibodies or antigen-binding portions described above which is an Fab fragment, an F(ab')$_2$ fragment, an F$_v$ fragment, a single chain Fv fragment, a single chain $V_H$ fragment, a single chain $V_L$ fragment, a humanized antibody, a chimeric antibody or a bispecific antibody. Another embodiment provides any of the antibodies or antigen-binding portions thereof described herein, which are isolated.

In a further embodiment is a derivatized antibody or antigen-binding portion comprising any of the antibodies or portions thereof as described herein and at least one additional molecular entity. For example, the at least one additional molecular entity can be another antibody (e.g., a bispecific antibody or a diabody), a detection agent, a label, a cytotoxic agent, a pharmaceutical agent, and/or a protein or peptide that can mediate association of the antibody or antibody portion with another molecule (such as a streptavidin core region or a polyhistidine tag). For example, useful detection agents with which an antibody or antigen-binding portion of the invention may be derivatized include fluorescent compounds, including fluorescein, fluorescein isothiocyanate, rhodamine, 5-dimethylamine-1-naphthalenesulfonyl chloride, phycoerythrin, lanthanide phosphors, and the like. An antibody can also be labeled with enzymes that are useful for detection, such as horseradish peroxidase, β-galactosidase, luciferase, alkaline phosphatase, glucose oxidase, and the like. In a further embodiment the antibodies or portions thereof of the present invention can also be labeled with biotin, or with a predetermined polypeptide epitope recognized by a secondary reporter (e.g., leucine zipper pair sequences, binding sites for secondary antibodies, metal binding domains, epitope tags). In a still further embodiment of the present invention, any of the antibodies or portions thereof can also be derivatized with a chemical group such as polyethylene glycol (PEG), a methyl or ethyl group, or a carbohydrate group.

In some embodiments, the P-cadherin antibodies or antigen binding portions disclosed herein are attached to a solid support.

In some embodiments, the C-terminal lysine of the heavy chain of any of the P-cadherin antibodies of the invention is cleaved. In various embodiments of the invention, the heavy and light chains of the P-cadherin antibodies may optionally include a N-terminal signal sequence. For example the heavy chain signal sequence can be SEQ ID NO: 346, and the light chain signal sequence can be SEQ ID NO: 347.

In a further embodiment, the present invention relates to any of the antibodies or antigen-binding portions thereof as described herein wherein the antibodies or antigen-binding portions thereof are of human origin.

The present invention also provides a pharmaceutical composition comprising any of the antibodies or antigen-binding portions thereof as described above and a pharmaceutically acceptable carrier.

In another embodiment, the invention relates to an isolated nucleic acid molecule comprising a nucleotide sequence that encodes any of the antibodies or antigen binding portions thereof as described herein. In one particular embodiment is an isolated nucleic acid molecule comprising a nucleotide sequence as set forth in any one of SEQ ID NOs: 68 to 90 and 332 to 343. The invention further relates to a vector comprising any of the nucleic acid molecules described herein, wherein the vector optionally comprises an expression control sequence operably linked to the nucleic acid molecule.

Another embodiment provides a host cell comprising any one of the vectors described herein or comprising any one of the nucleic acid molecules described herein. The present invention also provides an isolated cell line that produces any of the antibodies or antigen-binding portions as described herein or that produces the heavy chain or light chain of any of said antibodies or said antigen-binding portions.

In another embodiment, the present invention relates to a method for producing a P-cadherin antibody or antigen-binding portion thereof, comprising culturing any of the host cells or cell lines described herein under suitable conditions and recovering said antibody or antigen-binding portion.

The present invention also relates to a non-human transgenic animal or transgenic plant comprising any of the nucleic acids described herein, wherein the non-human transgenic animal or transgenic plant expresses said nucleic acid.

The present invention further provides a method for isolating an antibody or antigen-binding portion thereof that binds to P-cadherin, comprising the step of isolating the antibody from the non-human transgenic animal or transgenic plant as described herein.

The present invention also provides a method for treating abnormal cell growth in a mammal in need thereof, comprising the step of administering to said mammal any of the antibodies or antigen-binding portions thereof, or any of the pharmaceutical compositions, as described herein. The present invention further provides a method for treating abnormal cell growth in a mammal in need thereof with an antibody or antigen-binding portion thereof that binds to P-cadherin comprising the steps of administering to said mammal an effective amount of any of the nucleic acid molecules described herein under suitable conditions that allow expression of said nucleic acid molecules. In another embodiment, the method of treating abnormal cell growth further comprises administering an amount of one or more substances selected from anti-tumor agents, anti-angiogenesis agents, signal transduction inhibitors, and antiproliferative agents, which amounts are together effective in treating said abnormal cell growth. In particular embodiments, said abnormal cell growth is cancerous.

The present invention further provides a method for reducing P-cadherin-dependent cellular aggregation comprising contacting the cells with any of the antibodies or antigen-binding portions thereof described herein or any of the pharmaceutical compositions described herein.

Another aspect of the present invention is an antibody or antigen-binding portion thereof comprising a heavy chain variable region amino acid sequence that utilizes a human $V_H$-3 family gene. In one embodiment, for example, the human $V_H$-3 family gene is $V_H$-3-23.

Another aspect of the present invention provides any of the antibodies or antigen-binding portions thereof as described herein, where said antibody or antigen-binding portion is a human antibody. In a further aspect, said antibody or antigen-binding portion is a human recombinant antibody.

The invention also provides a method for producing a P-cadherin antibody or antigen-binding portion thereof comprising the steps of synthesizing a library of human antibodies on phage, screening the library with P-cadherin, or an antigenic portion thereof, isolating phage that bind P-cadherin, and obtaining the antibody from the phage.

DEFINITIONS AND GENERAL TECHNIQUES

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclature used in connection with, and techniques of, cell and tissue culture, molecular biology, immunology, microbiology, genetics and protein and nucleic acid chemistry and hybridization described herein are those well known and commonly used in the art.

The methods and techniques of the present invention are generally performed according to conventional methods well known in the art and as described in various general and more specific references that are cited and discussed throughout the present specification unless otherwise indicated. See, e.g., Sambrook, et al. *Molecular Cloning: A Laboratory Manual*, 3rd ed., Cold Spring Harbor Laboratory Press, Cold Spring Harbor, N.Y. (2000); Ausubel, et al., *Short Protocols in Molecular Biology: A Compendium of Methods from Current Protocols in Molecular Biology*, Wiley, John & Sons, Inc. (2002); Harlow and Lane *Using Antibodies: A Laboratory Manual*, Cold Spring Harbor Laboratory Press, Cold Spring Harbor, N.Y. (1998); and Coligan, et al., *Short Protocols in Protein Science*, Wiley, John & Sons, Inc. (2003), the disclosures of which are incorporated herein by reference. Enzymatic reactions and purification techniques are performed according to manufacturer's specifications, as commonly accomplished in the art or as described herein. The nomenclature used in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, delivery, and treatment of patients.

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 120 or more amino acids primarily responsible for antigen recognition. The carboxy-terminal portion of each chain defines a constant region primarily responsible for effector function. Human light chains are classified as kappa and lambda light chains. Heavy chains are classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 3 or more amino acids. See generally, *Fundamental Immunology*, Ch. 7 (Paul, W., ed., 2nd ed. Raven Press, N.Y. (1989)) (incorporated herein by reference in its entirety for all purposes). The variable regions of each heavy/light chain pair ($V_H$ and $V_L$) form the antibody binding site. Thus, an intact IgG antibody, for example, has two binding sites. Except in bifunctional or bispecific antibodies, the two binding sites are the same.

The variable regions of the heavy and light chains exhibit the same general structure of relatively conserved framework regions (FR) joined by three hyper variable regions, also called complementarity determining regions or CDRs. The term "variable" refers to the fact that certain portions of the variable domains differ extensively in sequence among antibodies and are used in the binding and specificity of each particular antibody for its particular antigen. The variability, however, is not evenly distributed throughout the variable domains of antibodies, but is concentrated in the CDRs, which are separated by the more highly conserved FRs. The CDRs from the two chains of each pair are aligned by the FRs, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with the definitions of Kabat Sequences of Proteins of Immunological Interest (National Institutes of Health, Bethesda, Md. (1987 and 1991)), or Chothia & Lesk *J. Mol. Biol.*, 196:901-917 (1987); Chothia, et al., *Nature* 342:878-883 (1989), the disclosures of which are herein incorporated by reference.

The following terms, unless otherwise indicated, shall be understood to have the following meanings:

Unless specifically indicated otherwise, the term "P-cadherin" refers to human P-cadherin, which is an integral membrane protein and a member of the classical cadherin family of transmembrane glycoproteins that regulate cell-cell adhesion. The cloning and sequence of human P-cadherin has been reported, e.g. Shimoyama, et al., J. *Cell Biol.* 109 (4 Pt 1), 1787-1794 (1989), the disclosure of which is herein incorporated by reference. The term P-cadherin is intended to include recombinant human P-cadherin and recombinant chimeric forms of P-cadherin, which can be prepared by standard recombinant expression methods or purchased commercially (R&D Systems 861-PC-100).

Unless specifically indicated otherwise, as used herein the term "E-cadherin" refers to human E-cadherin, which is an integral membrane protein and a member of the classical cadherin family of transmembrane glycoproteins that regulate cell-cell adhesion. E-cadherin is described, for example, in Takeichi, *Science,* 251: 1451-1455 (1991), the disclosure of which is herein incorporated by reference. The term E-cadherin is intended to include recombinant human E-cadherin and recombinant chimeric forms of E-cadherin, which can be prepared by standard recombinant expression methods or purchased commercially (R&D 648-EC-100).

The term "polypeptide" encompasses native or artificial proteins, protein fragments and polypeptide analogs of a protein sequence. A polypeptide may be monomeric or polymeric.

The term "isolated protein", "isolated polypeptide" or "isolated antibody" is a protein, polypeptide or antibody that by virtue of its origin or source of derivation (1) is not associated with naturally associated components that accompany it in its native state, (2) is free of other proteins from the same species, (3) is expressed by a cell from a different species, or (4) does not occur in nature. Thus, a polypeptide that is chemically synthesized or synthesized in a cellular system different from the cell from which it naturally originates will be "isolated" from its naturally associated components. A protein may also be rendered substantially free of naturally associated components by isolation, using protein purification techniques well known in the art.

Examples of isolated antibodies include a P-cadherin antibody that has been affinity purified using P-cadherin, and a P-cadherin antibody that has been synthesized by a cell line in vitro.

A protein or polypeptide is "substantially pure," "substantially homogeneous," or "substantially purified" when at least about 60 to 75% of a sample exhibits a single species of polypeptide. The polypeptide or protein may be monomeric or multimeric. A substantially pure polypeptide or protein can typically comprise about 50%, 60%, 70%, 80% or 90% w/w of a protein sample, more usually about 95%, and preferably can be over 99% pure. Protein purity or homogeneity may be indicated by a number of means well known in the art, such as polyacrylamide gel electrophoresis of a protein sample, followed by visualizing a single polypeptide band upon staining the gel with a stain well known in the art. For certain purposes, higher resolution may be provided by using HPLC or other means well known in the art for purification.

The term "polypeptide fragment" as used herein refers to a polypeptide that has an amino-terminal and/or carboxy-terminal deletion, but where the remaining amino acid sequence is identical to the corresponding positions in the naturally-occurring sequence. In some embodiments, fragments are at least 5, 6, 8 or 10 amino acids long. In other embodiments, the fragments are at least 14, at least 20, at least 50, or at least 70, 80, 90, 100, 150 or 200 amino acids long.

The term "analog" or "polypeptide analog" as used herein refers to a polypeptide that comprises a segment that has substantial identity to some reference amino acid sequence and has substantially the same function or activity as the reference amino acid sequence. Typically, polypeptide analogs comprise a conservative amino acid substitution (or insertion or deletion) with respect to the reference sequence. Analogs can be at least 20 or 25 amino acids long, or can be at least 50, 60, 70, 80, 90, 100, 150 or 200 amino acids long or longer, and can often be as long as the full-length polypeptide. Some embodiments of the invention include polypeptide fragments or polypeptide analog antibodies with 1, 2, 3, 4, 5, 6, 7, 8, 9, 10, 11, 12, 13, 14, 15, 16 or 17 substitutions from the germline amino acid sequence. Fragments or analogs of antibodies or immunoglobulin molecules can be readily prepared by those of ordinary skill in the art following the teachings of this specification.

In certain embodiments, amino acid substitutions to a P-cadherin antibody or antigen-binding portion thereof are those which: (1) reduce susceptibility to proteolysis, (2) reduce susceptibility to oxidation, (3) alter binding affinity for forming protein complexes, and (4) confer or modify other physicochemical or functional properties of such analogs, but still retain specific binding to P-cadherin. Analogs can include various substitutions to the normally-occurring peptide sequence. For example, single or multiple amino acid substitutions, preferably conservative amino acid substitutions, may be made in the normally-occurring sequence, for example in the portion of the polypeptide outside the domain(s) forming intermolecular contacts. Amino acid substitutions can also be made in the domain(s) that form intermolecular contacts that can improve the activity of the polypeptide. A conservative amino acid substitution should not substantially change the structural characteristics of the parent sequence; e.g., a replacement amino acid should not alter the anti-parallel β-sheet that makes up the immunoglobulin binding domain that occurs in the parent sequence, or disrupt other types of secondary structure that characterizes the parent sequence. In general, glycine and proline would not be used in an anti-parallel β-sheet. Examples of art-recognized polypeptide secondary and tertiary structures are described in *Proteins, Structures and Molecular Principles* (Creighton, Ed., W. H. Freeman and Company, New York (1984)); Introduction to Protein Structure (C. Branden and J. Tooze, eds., Garland Publishing, New York, N.Y. (1991)); and Thornton, et al., *Nature,* 354:105 (1991), incorporated herein by reference.

As used herein, the term "antibody" is synonymous with immunoglobulin and is to be understood as commonly known in the art. In particular, the term antibody is not limited by any particular method of producing the antibody. For example, the term antibody includes, without limitation, recombinant antibodies, monoclonal antibodies, and polyclonal antibodies.

The term "antigen-binding portion" of an antibody (or simply "antibody portion"), as used herein, refers to one or more fragments of an antibody that retain the ability to specifically bind to an antigen (e.g., P-cadherin). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_H 1$ domains; (ii) a F(ab')$_2$ fragment, a bivalent fragment comprising two Fab fragments linked by a disulfide bridge at the hinge region; (iii) a Fd fragment consisting of the $V_H$ and $C_H 1$ domains; (iv) a Fv fragment consisting of the $V_L$ and $V_H$ domains of a single arm of an antibody, (v) a dAb fragment (Ward, et al., *Nature*, (1989) 341:544-546), which consists of a $V_H$ domain; and (vi) an isolated complementarity determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv)); see e.g., Bird, et al., *Science* (1988) 242:423-426 and Huston, et al., *Proc. Natl. Acad. Sci. USA*, 85:5879-5883 (1988)). Such single chain antibodies are also intended to be encompassed within the term "antigen-binding portion" of an antibody. Other forms of single chain antibodies, such as diabodies are also encompassed. Diabodies are bivalent, bispecific antibodies in which $V_H$ and $V_L$ domains are expressed on a single polypeptide chain, but using a linker that is too short to allow for pairing between the two domains on the same chain, thereby forcing the domains to pair with complementary domains of another chain and creating two antigen binding sites (see e.g., Holliger, et al., *Proc. Natl. Acad. Sci. USA*, 90:6444-6448 (1993); Poljak, et al. *Structure*, 2:1121-1123 (1994)).

Still further, an antibody or antigen-binding portion thereof may be part of larger immunoadhesion molecules, formed by covalent or noncovalent association of the antibody or antibody portion with one or more other proteins or peptides. Examples of such immunoadhesion molecules include use of the streptavidin core region to make a tetrameric scFv molecule (Kipriyanov, et al., *Human Antibodies and Hybridomas*, 6:93-101 (1995)) and use of a cysteine residue, a marker peptide and a C-terminal polyhistidine tag to make bivalent and biotinylated scFv molecules (Kipriyanov, et al., *Mol. Immunol.*, 31:1047-1058 (1994)). Other examples include where one or more CDRs from an antibody are incorporated into a molecule either covalently or noncovalently to make it an immunoadhesin that specifically binds to an antigen of interest, such as P-cadherin. In such embodiments, the CDR(s) may be incorporated as part of a larger polypeptide chain, may be covalently linked to another polypeptide chain, or may be incorporated noncovalently. Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein.

Where an "antibody" is referred to herein with respect to the present invention, it should be understood that an antigen-binding portion thereof may also be used. An antigen-binding portion competes with the intact antibody for specific binding. See generally, *Fundamental Immunology*, Ch. 7 (Paul, W., ed., 2nd ed. Raven Press, N.Y. (1989)) (incorporated by reference in its entirety for all purposes). Antigen-binding portions may be produced by recombinant DNA techniques or by enzymatic or chemical cleavage of intact antibodies. In some embodiments, antigen-binding portions include Fab, Fab', F(ab')$_2$, Fd, Fv, dAb, and complementarity determining region (CDR) fragments, single-chain antibodies (scFv), chimeric antibodies, diabodies and polypeptides that contain at least a portion of an antibody that is sufficient to confer specific antigen binding to the polypeptide. In embodiments having one or more binding sites, the binding sites may be identical to one another or may be different.

As used herein, the term "human antibody" means any antibody in which the variable and constant domain sequences are human sequences. The term encompasses antibodies with sequences derived from human genes, but which have been changed, e.g. to decrease possible immunogenicity, increase affinity, eliminate cysteines that might cause undesirable folding, etc. The term also encompasses such antibodies produced recombinantly in non-human cells, which might impart glycosylation not typical of human cells. These antibodies may be prepared in a variety of ways, as described below.

The term "chimeric antibody" as used herein means an antibody that comprises regions from two or more different antibodies, including antibodies from different species. For example, one or more of the CDRs of a chimeric antibody can be derived from a human P-cadherin antibody. In one example, the CDRs from a human antibody can be combined with CDRs from a non-human antibody, such as mouse or rat. In another example, all of the CDRs can be derived from human P-cadherin antibodies. In another example, the CDRs from more than one human P-cadherin antibody can be combined in a chimeric antibody. For instance, a chimeric antibody may comprise a CDR1 from the light chain of a first human P-cadherin antibody, a CDR2 from the light chain of a second human P-cadherin antibody and a CDR3 from the light chain of a third human P-cadherin antibody, and CDRs from the heavy chain may be derived from one or more other P-cadherin antibodies. Further, the framework regions may be derived from one of the P-cadherin antibodies from which one or more of the CDRs are taken or from one or more different human antibodies. Further, the term "chimeric antibody" is intended to encompass any of the above mentioned combinations where the combinations involved human and non-human antibodies.

As used herein, the term "humanized antibody" refers to antibodies of non-human origin, wherein the amino acid residues that are characteristic of antibody sequences of the non-human species are replaced with residues found in the corresponding positions of human antibodies. This "humanization" process is thought to reduce the immunogenicity in humans of the resulting antibody. It will be appreciated that antibodies of non-human origin can be humanized using techniques well known in the art. See, e.g. Winter, et al., *Immunol. Today*, 14:43-46 (1993). The antibody of interest may be engineered by recombinant DNA techniques to substitute the CH1, CH2, CH3, hinge domains, and/or the framework domain with the corresponding human sequence. See, e.g. WO 92/02190, and U.S. Pat. Nos. 5,530,101, 5,585,089, 5,693,761, 5,693,792, 5,714,350, and 5,777,085). The term "humanized antibody", as used herein, includes within its meaning, chimeric human antibodies and CDR-grafted antibodies. Chimeric human antibodies of the invention include the $V_H$ and $V_L$ of an antibody of a non-human species and the $C_H$ and $C_L$ domains of a human antibody. The CDR-transplanted antibodies of the invention result from the replacement of CDRs of the $V_H$ and $V_L$ of a human antibody with those of the $V_H$ and $V_L$, respectively, of an antibody of an animal other than a human.

As used herein, the term "ELISA" refers to an enzyme-linked immunosorbent assay. This assay is well known to those of skill in the art. Examples of this assay can be found in Vaughan, T. J., et al., *Nat. Biotech.*, 14:309-314 (1996), as well as in Example 7 of the present application.

The term "surface plasmon resonance", as used herein, refers to an optical phenomenon that allows for the analysis of real-time biospecific interactions by detection of alterations in protein concentrations within a biosensor matrix, for example using the BIACORE™ system (Pharmacia Biosensor AB, Uppsala, Sweden and Piscataway, N.J.). For further descriptions, see Jonsson et al., *Ann. Biol. Clin.*, 51:19-26 (1993); Jonsson, et al., *Biotechniques*, 11:620-627 (1991);

Jonsson, et al., *J. Mol. Recognit.*, 8:125-131 (1995); and Johnsson, et al., *Anal. Biochem.*, 198:268-277 (1991).

The term "$K_D$" refers to the binding affinity equilibrium constant of a particular antibody-antigen interaction. An antibody is said to specifically bind an antigen when the $K_D$ is ≤1 mM, preferably 100 nM and most preferably 10 nM. A $K_D$ binding affinity constant can be measured by surface plasmon resonance, for example using the BIACORE™ system as discussed in Example 6.

The term "$k_{off}$" refers to the dissociation rate constant of a particular antibody-antigen interaction. A $k_{off}$ dissociation rate constant can be measured by surface plasmon resonance, for example using the BIACORE™ system as discussed in Example 6.

As used herein, the term "P-cadherin dependent cell adhesion assay" refers to an assay used to measure the ability of a P-cadherin antibody to block the adhesion of cells to a receptor P-cadherin that has been immobilized on a solid support. This type of assay can be carried out, for example, by immobilizing P-cadherin on a solid support, such as plastic. Cells over-expressing P-cadherin are then allowed to adhere to the solid support via P-cadherin-P-cadherin interactions. The level of adhesion can then be quantified with and without a P-cadherin antibody. Adhesion as a function of antibody concentration can then be used to determine an $IC_{50}$ value. Example 3 provides further details of a P-cadherin-dependent cell adhesion assay that was used to measure $IC_{50}$ values for P-cadherin antibodies.

As used herein, the term "P-cadherin dependent cell aggregation assay" refers to an assay for measuring the ability of a P-cadherin antibody to block aggregation of cells expressing P-cadherin on their surfaces. For example, this type of assay can use a cell line that over-expresses P-cadherin, wherein the cells are placed into suspension and allowed to form P-cadherin-dependent aggregates. The aggregation assay is then used to quantify the ability of a P-cadherin antibody to prevent this aggregation by measuring the size of cellular aggregates that result with and without the antibody. Cell aggregate size as a function of P-cadherin antibody concentration can then be used to determine an $IC_{50}$ value. Example 4 provides further details of a P-cadherin-dependent aggregation assay that was used to measure $IC_{50}$ values for several P-cadherin antibodies.

As used herein, the term "P-cadherin-dependent spheroid disruption assay" refers to an assay for measuring the ability of a P-cadherin antibody to disrupt pre-formed P-cadherin-dependent cellular aggregations. By measuring the size reduction of aggregates as a function of antibody concentration, an $IC_{50}$ value can be determined. Example 5 provides further details of a P-cadherin-dependent spheroid disruption assay that was used to measure $IC_{50}$ values for P-cadherin antibodies.

As used herein, the term "molecular selectivity" refers to the binding affinity of an antibody for a specific antigen being greater than for a related antigen. For example, the antibodies of the present invention can be selective for P-cadherin over E-cadherin, meaning that the binding affinity of the antibody for P-cadherin is at least 2 times greater, for example 4 times, or 10 times, or 50 times, or 100 times or more, than for E-cadherin. Such binding affinities can be measured using standard techniques known to those of skill in the art.

The term "epitope" includes any protein determinant capable of specific binding to an immunoglobulin or T-cell receptor or otherwise interacting with a molecule. Epitopic determinants generally consist of chemically active surface groupings of molecules such as amino acids or carbohydrate or sugar side chains and generally have specific three dimensional structural characteristics, as well as specific charge characteristics. An epitope may be "linear" or "conformational." In a linear epitope, all of the points of interaction between the protein and the interacting molecule (such as an antibody) occur linearly along the primary amino acid sequence of the protein. In a conformational epitope, the points of interaction occur across amino acid residues on the protein that are separated from one another. Once a desired epitope on an antigen is determined, it is possible to generate antibodies to that epitope, e.g., using the techniques described in the present invention. Alternatively, during the discovery process, the generation and characterization of antibodies may elucidate information about desirable epitopes. From this information, it is then possible to competitively screen antibodies for binding to the same epitope. An approach to achieve this is to conduct cross-competition studies to find antibodies that competitively bind with one another, i.e. the antibodies compete for binding to the antigen. A high throughput process for "binning" antibodies based upon their cross-competition is described in International Patent Publication No. WO 03/48731.

The term "compete", as used herein with regard to an antibody, means that a first antibody, or an antigen-binding portion thereof, competes for binding with a second antibody, or an antigen-binding portion thereof, where binding of the first antibody with its cognate epitope is detectably decreased in the presence of the second antibody compared to the binding of the first antibody in the absence of the second antibody. The alternative, where the binding of the second antibody to its epitope is also detectably decreased in the presence of the first antibody, can, but need not be the case. That is, a first antibody can inhibit the binding of a second antibody to its epitope without that second antibody inhibiting the binding of the first antibody to its respective epitope. However, where each antibody detectably inhibits the binding of the other antibody with its cognate epitope or ligand, whether to the same, greater, or lesser extent, the antibodies are said to "cross-compete" with each other for binding of their respective epitope(s). Both competing and cross-competing antibodies are encompassed by the present invention. Regardless of the mechanism by which such competition or cross-competition occurs (e.g., steric hindrance, conformational change, or binding to a common epitope, or portion thereof, and the like), the skilled artisan would appreciate, based upon the teachings provided herein, that such competing and/or cross-competing antibodies are encompassed and can be useful for the methods disclosed herein.

As used herein, the term "utilizes" with reference to a particular gene means that the amino acid sequence of a particular region in an antibody was ultimately derived from that gene during B-cell maturation. For example, the phrase "a heavy chain variable region amino acid sequence that utilizes a human $V_H$-3 family gene" refers to the situation where the $V_H$ region of the antibody was derived from the VH-3 family of gene segments during B-cell maturation. In human B-cells, there are more than 30 distinct functional heavy chain variable genes with which to generate antibodies. Use of a particular heavy chain variable gene, therefore, is indicative of a preferred binding motif of the antibody-antigen interaction with respect to the combined properties of binding to the antigen and functional activity. As will be appreciated, gene utilization analysis provides only a limited overview of antibody structure. As human B-cells stocastically generate V-D-J heavy or V-J kappa light chain transcripts, there are a number of secondary processes that occur, including, without limitation, somatic hypermutation, n-additions, and CDR3 extensions. See, for example, Mendez et al. *Nature Genetics* 15:146-156 (1997).

As used herein, the twenty conventional amino acids and their abbreviations follow conventional usage. See *Immunology—A Synthesis* (2$^{nd}$ Edition, E. S. Golub and D. R. Gren, Eds., Sinauer Associates, Sunderland, Mass. (1991)), incorporated herein by reference.

The term "polynucleotide" as referred to herein means a polymeric form of nucleotides of at least 10 bases in length, either ribonucleotides or deoxynucleotides or a modified form of either type of nucleotide. The term includes single and double stranded forms.

The term "isolated polynucleotide" as used herein means a polynucleotide of genomic, cDNA, or synthetic origin or some combination thereof, which by virtue of its origin the "isolated polynucleotide" (1) is not associated with all or a portion of polynucleotides with which the "isolated polynucleotide" is found in nature, (2) is operably linked to a polynucleotide to which it is not linked in nature, or (3) does not occur in nature as part of a larger sequence.

The term "naturally occurring nucleotides" as used herein includes deoxyribonucleotides and ribonucleotides. The term "modified nucleotides" as used herein includes nucleotides with modified or substituted sugar groups and the like. The term "oligonucleotide linkages" referred to herein includes oligonucleotides linkages such as phosphorothioate, phosphorodithioate, phosphoroselenoate, phosphorodiselenoate, phosphoroanilothioate, phoshoraniladate, phosphoroamidate, and the like. See e.g., LaPlanche, et al., *Nucl. Acids Res.*, 14:9081 (1986); Stec, et al., *J. Am. Chem. Soc.*, 106:6077 (1984); Stein, et al., *Nucl. Acids Res.*, 16:3209 (1988); Zon, et al., *Anti-Cancer Drug Design*, 6:539 (1991); Zon, et al., *Oligonucleotides and Analogues: A Practical Approach*, pp. 87-108 (F. Eckstein, Ed., Oxford University Press, Oxford England (1991)); U.S. Pat. No. 5,151,510; Uhlmann and Peyman, *Chemical Reviews*, 90:543 (1990), the disclosures of which are hereby incorporated by reference. An oligonucleotide can include a label for detection, if desired.

"Operably linked" sequences include both expression control sequences that are contiguous with the gene of interest and expression control sequences that act in trans or at a distance to control the gene of interest.

The term "expression control sequence" as used herein means polynucleotide sequences that are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences.

The term "vector", as used herein, means a nucleic acid molecule capable of transporting another nucleic acid to which it has been linked. In some embodiments, the vector is a plasmid, i.e., a circular double stranded piece of DNA into which additional DNA segments may be ligated. In some embodiments, the vector is a viral vector, wherein additional DNA segments may be ligated into the viral genome. In some embodiments, the vectors are capable of autonomous replication in a host cell into which they are introduced (e.g., bacterial vectors having a bacterial origin of replication and episomal mammalian vectors). In other embodiments, the vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors").

The term "recombinant host cell" (or simply "host cell"), as used herein, means a cell into which a recombinant expression vector has been introduced. It should be understood that "recombinant host cell" and "host cell" mean not only the particular subject cell but also the progeny of such a cell. Because certain modifications may occur in succeeding generations due to either mutation or environmental influences, such progeny may not, in fact, be identical to the parent cell, but are still included within the scope of the term "host cell" as used herein.

As used herein, the term "germline" refers to the nucleotide sequences of the antibody genes and gene segments as they are passed from parents to offspring via the germ cells. This germline sequence is distinguished from the nucleotide sequences encoding antibodies in mature B cells which have been altered by recombination and hypermutation events during the course of B cell maturation.

The term "percent sequence identity" in the context of nucleic acid sequences means the residues in two sequences that are the same when aligned for maximum correspondence. The length of sequence identity comparison may be over a stretch of at least about nine nucleotides, usually at least about 18 nucleotides, more usually at least about 24 nucleotides, typically at least about 28 nucleotides, more typically at least about 32 nucleotides, and preferably at least about 36, 48 or more nucleotides. There are a number of different algorithms known in the art which can be used to measure nucleotide sequence identity. For instance, polynucleotide sequences can be compared using FASTA, Gap or Bestfit, which are programs in Wisconsin Package Version 10.0, Genetics Computer Group (GCG), Madison, Wis. FASTA, which includes, e.g., the programs FASTA2 and FASTA3, provides alignments and percent sequence identity of the regions of the best overlap between the query and search sequences (Pearson, *Methods Enzymol.*, 183:63-98 (1990); Pearson, *Methods Mol. Biol.*, 132:185-219 (2000); Pearson, *Methods Enzymol.*, 266:227-258 (1996); Pearson, *J. Mol. Biol.* 276:71-84 (1998); incorporated herein by reference). Unless otherwise specified, default parameters for a particular program or algorithm are used. For instance, percent sequence identity between nucleic acid sequences can be determined using FASTA with its default parameters (a word size of 6 and the NOPAM factor for the scoring matrix) or using Gap with its default parameters as provided in GCG Version 6.1, incorporated herein by reference.

A reference to a nucleotide sequence encompasses its complement unless otherwise specified. Thus, a reference to a nucleic acid having a particular sequence should be understood to encompass its complementary strand, with its complementary sequence.

The term "substantial similarity" or "substantial sequence similarity," when referring to a nucleic acid or fragment thereof, means that when optimally aligned with appropriate nucleotide insertions or deletions with another nucleic acid (or its complementary strand), there is nucleotide sequence identity in at least about 85%, preferably at least about 90%, and more preferably at least about 95%, 96%, 97%, 98% or 99% of the nucleotide bases, as measured by any well-known algorithm of sequence identity, such as FASTA, BLAST or Gap, as discussed above.

The term "percent sequence identity" in the context of amino acid sequences means the residues in two sequences that are the same when aligned for maximum correspondence. The length of sequence identity comparison may be over a stretch of at least about five amino acids, usually at least about 20 amino acids, more usually at least about 30 amino acids, typically at least about 50 amino acids, more typically at least about 100 amino acids, and even more typically about 150, 200 or more amino acids. There are a number of different algorithms known in the art that can be used to measure amino acid sequence identity. For instance, amino acid sequences can be compared using FASTA, Gap or Bestfit, which are programs in Wisconsin Package Version 10.0, Genetics Computer Group (GCG), Madison, Wis.

As applied to polypeptides, the term "substantial identity" or "substantial similarity" means that two amino acid sequences, when optimally aligned, such as by the programs GAP or BESTFIT using default gap weights as supplied with the programs, share at least 70%, 75% or 80% sequence identity, preferably at least 90% or 95% sequence identity, and more preferably at least 97%, 98% or 99% sequence identity. In certain embodiments, residue positions that are not identical differ by conservative amino acid substitutions.

As the ther is used herein, a "conservative amino acid substitution" is one in which an amino acid residue is substituted by another amino acid residue having a side chain R group with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity may be adjusted upwards to correct for the conservative nature of the substitution. Means for making this adjustment are well-known to those of skill in the art. See, e.g., Pearson, *Methods Mol. Biol.*, 243:307-31 (1994). Examples of groups of amino acids that have side chains with similar chemical properties include 1) aliphatic side chains: glycine, alanine, valine, leucine, and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartic acid and glutamic acid; and 7) sulfur-containing side chains: cysteine and methionine. For example, conservative amino acids substitution groups can be: valine-leucine-isoleucine, phenylalanine-tyrosine, lysine-arginine, alanine-valine, glutamate-aspartate, and asparagine-glutamine.

Alternatively, a conservative replacement is any change having a positive value in the PAM250 log-likelihood matrix disclosed in Gonnet et al., *Science* 256:1443-45 (1992), incorporated herein by reference. A "moderately conservative" replacement is any change having a nonnegative value in the PAM250 log-likelihood matrix.

Sequence identity for polypeptides is typically measured using sequence analysis software. Protein analysis software matches sequences using measures of similarity assigned to various substitutions, deletions and other modifications, including conservative amino acid substitutions. For instance, GCG contains programs such as "Gap" and "Bestfit" which can be used with default parameters as specified by the programs to determine sequence homology or sequence identity between closely related polypeptides, such as homologous polypeptides from different species of organisms or between a wild type protein and an analog thereof. See, e.g., GCG Version 6.1 (University of Wisconsin, WI). Polypeptide sequences also can be compared using FASTA using default or recommended parameters, see GCG Version 6.1. FASTA (e.g., FASTA2 and FASTA3) provides alignments and percent sequence identity of the regions of the best overlap between the query and search sequences (Pearson, *Methods Enzymol.*, 183:63-98 (1990); Pearson, *Methods Mol. Biol.*, 132:185-219 (2000)). Another preferred algorithm when comparing a sequence of the invention to a database containing a large number of sequences from different organisms is the computer program BLAST, especially blastp or tblastn, using default parameters as supplied with the programs. See, e.g., Altschul, et al., *J. Mol. Biol.*, 215:403-410 (1990); Altschul, et al., *Nucleic Acids Res.*, 25:3389-402 (1997).

The length of polypeptide sequences compared for homology will generally be at least about 16 amino acid residues, usually at least about 20 residues, more usually at least about 24 residues, typically at least about 28 residues, and preferably more than about 35 residues. When searching a database containing sequences from a large number of different organisms, it is preferable to compare amino acid sequences.

As used herein, the terms "label" or "labeled" refers to incorporation of another molecule in the antibody. In one embodiment, the label is a detectable marker, e.g., incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). In another embodiment, the label or marker can be therapeutic, e.g., a drug conjugate or toxin. Various methods of labeling polypeptides and glycoproteins are known in the art and may be used. Examples of labels for polypeptides include, but are not limited to, the following: radioisotopes or radionuclides (e.g., $^{3}$H, $^{14}$C, $^{15}$N, $^{35}$S, $^{90}$Y, $^{99}$Tc, $^{111}$In, $^{125}$I, $^{131}$I), fluorescent labels (e.g., FITC, rhodamine, lanthanide phosphors), enzymatic labels (e.g., horseradish peroxidase, β-galactosidase, luciferase, alkaline phosphatase), chemiluminescent markers, biotinyl groups, predetermined polypeptide epitopes recognized by a secondary reporter (e.g., leucine zipper pair sequences, binding sites for secondary antibodies, metal binding domains, epitope tags), magnetic agents, such as gadolinium chelates, toxins such as pertussis toxin, taxol, cytochalasin B, gramicidin D, ethidium bromide, emetine, mitomycin, etoposide, tenoposide, vincristine, vinblastine, colchicine, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. In some embodiments, labels are attached by spacer arms of various lengths to reduce potential steric hindrance.

"Therapeutically effective amount" refers to that amount of the therapeutic agent being administered which will relieve to some extent one or more of the symptoms of the disorder being treated. In reference to the treatment of cancer, a therapeutically effective amount refers to that amount which has at least one of the following effects: reducing the size of the tumor; inhibiting (that is, slowing to some extent, preferably stopping) tumor metastasis; inhibiting to some extent (that is, slowing to some extent, preferably stopping) tumor growth, and relieving to some extent (or, preferably, eliminating) one or more symptoms associated with the cancer.

"Treat", "treating" and "treatment" refer to a method of alleviating or abrogating a biological disorder and/or its attendant symptoms. With regard to cancer, these terms simply mean that the life expectancy of an individual affected with a cancer will be increased or that one or more of the symptoms of the disease will be reduced.

"Contacting" refers to bringing an antibody or antigen binding portion thereof of the present invention and a target P-cadherin, or epitope thereof, together in such a manner that the antibody can affect the biological activity of the P-cadherin. Such "contacting" can be accomplished "in vitro," i.e., in a test tube, a petri dish, or the like. In a test tube, contacting may involve only an antibody or antigen binding portion thereof and P-cadherin or epitope thereof or it may involve whole cells. Cells may also be maintained or grown in cell culture dishes and contacted with antibodies or antigen binding portions thereof in that environment. In this context, the ability of a particular antibody or antigen binding portion thereof to affect a P-cadherin-related disorder, i.e., the $IC_{50}$ of the antibody, can be determined before use of the antibody in vivo with more complex living organisms is attempted. For cells outside the organism, multiple methods exist, and are well-known to those skilled in the art, to contact P-cadherin with the antibodies or antigen-binding portions thereof.

"Abnormal cell growth", as used herein, unless otherwise indicated, refers to cell growth that is independent of normal regulatory mechanisms (e.g., loss of contact inhibition), including the abnormal growth of normal cells and the growth of abnormal cells. This includes, but is not limited to, the abnormal growth of: tumor cells (tumors) that proliferate by expressing a mutated tyrosine kinase or overexpression of a receptor tyrosine kinase; benign and malignant cells of other proliferative diseases in which aberrant tyrosine kinase activation occurs; any tumors that proliferate by receptor tyrosine kinases; any tumors that proliferate by aberrant serine/threonine kinase activation; benign and malignant cells of other proliferative diseases in which aberrant serine/threonine kinase activation occurs; tumors, both benign and malignant, expressing an activated Ras oncogene; tumor cells, both benign and malignant, in which the Ras protein is activated as a result of oncogenic mutation in another gene; benign and malignant cells of other proliferative diseases in which aberrant Ras activation occurs. Examples of such benign proliferative diseases are psoriasis, benign prostatic hypertrophy, human papilloma virus (HPV), and restinosis. "Abnormal cell growth" also refers to and includes the abnormal growth of cells, both benign and malignant, resulting from activity of the enzyme farnesyl protein transferase.

The terms "abnormal cell growth" and "hyperproliferative disorder" are used interchangeably in this application.

"In vitro" refers to procedures performed in an artificial environment such as, e.g., without limitation, in a test tube or culture medium.

"In vivo" refers to procedures performed within a living organism such as, without limitation, a mouse, rat or rabbit.

BRIEF DESCRIPTION OF THE DRAWINGS

FIG. 1 shows the amino acid and nucleic acid sequences of SEQ ID NOs: 1-347.

DETAILED DESCRIPTION OF THE INVENTION

Human P-Cadherin Antibodies

This invention pertains to isolated human antibodies, or antigen-binding portions thereof, that bind to human P-cadherin. Preferably, the human antibodies are recombinant human P-cadherin antibodies that have greater affinity for P-cadherin than for E-cadherin. Various aspects of the invention relate to such antibodies and antigen-binding portions, and pharmaceutical compositions thereof, as well as nucleic acids, recombinant expression vectors and host cells for making such antibodies and antigen-binding portions. Methods of using the antibodies and antigen-binding portions of the present invention to detect human P-cadherin or to inhibit human P-cadherin activity, either in vitro or in vivo, are also encompassed by the invention.

The P-cadherin amino acid and nucleotide sequences from several species, including human, are known (see e.g. Accession No. NM_001793.3). Human P-cadherin, or antigenic portions thereof, can be prepared according to methods well known to those in the art, or can be purchased from commercial vendors (e.g. R&D Systems 861-PC-100).

In certain embodiments, antibodies of the present invention are IgGs designated as: 194-e06; 194-a02; 194-b09; 195-e11; 194-g09; 196-h02; 194-e01; 196-d10; 196-g03; 196-e06; 195-a09; 198-a09; 200-h06; g-194-b09; g-194-g09; g-196-g03; g-196-h02; g-194-e01; g-194-e06; 129-1c4; and g-129-1c4. As discussed in greater detail in Example 1, high throughput screening of a scFv phage display library was used to identify the 129-1c4 scFv, which was subsequently converted to an IgG. 129-1c4 represents the lead antibody identified during initial phage display screening and is the parent antibody of a lineage from which several other antibodies of the present invention were derived. Several of such derived antibodies are designated as 194-e06; 194-a02; 194-b09; 195-e11; 194-g09; 196-h02; 194-e01; 196-d10; 196-g03; 196-e06; 195-a09; 198-a09; and 200-h06 and represent optimized antibodies within the 129-1c4 parent lineage. The g-129-1c4 antibody is the germline version of the 129-1c4 parent antibody where certain amino acids in the framework regions of the $V_H$ and $V_L$ domains were mutated to match those in the germline framework regions. Any of the antibodies mentioned above can also be germlined so that the framework region sequences are identical to the germline framework sequences as in g-129-1c4. For example in one embodiment of the present invention, the antibodies g-194-b09, g-194-g09, g-196-g03, g-196-h02, g-194-e01, g-195-e11, g-200-h06, and g-194-e06 are the germlined versions of 194-b09, 194-g09, 196-g03, 196-h02, 194-e01, 195-e11, 200-h06, and 194-e06, respectively. The specific amino acids that were mutated to arrive at the germlined versions are apparent to those of skill in the art by comparing the sequences of a germlined vs. a non-germlined antibody. As discussed below, specific amino acid sequences of the antibodies of the present invention are described in Tables 1-3 and FIG. 1.

Antibodies of the present invention were generated with a strong bias towards the utilization of the $V_H3$ gene family of heavy chain variable regions. In particular, the 129-1c4 parent antibody derived from the $V_H3$-23 variable gene segment. In human B-cells, there are more than 30 distinct functional heavy chain variable genes with which to generate antibodies. Bias, therefore, is indicative of a preferred binding motif of the antibody-antigen interaction with respect to the combined properties of binding to the antigen and functional activity.

As will be appreciated, gene utilization analysis provides only a limited overview of antibody structure. As human B-cells stochastically generate V-D-J heavy or V-J kappa light chain transcripts, there are a number of secondary processes that occur, including, without limitation, somatic hypermutation, n-additions, and CDR3 extensions. See, for example, Mendez et al. *Nature Genetics* 15:146-156 (1997) and U.S.

published patent application 2003-0070185, filed Feb. 19, 2002. Accordingly, to further examine antibody structure of the present invention, predicted amino acid sequences of the antibodies were generated from the cDNAs obtained from the clones. In addition, N-terminal amino acid sequences were obtained through protein sequencing. FIG. 1 provides nucleotide and amino acid sequences of the heavy and light chain variable regions of several of the antibodies of the present invention.

Each of the specific antibodies mentioned above can be described by their variable domain sequences of the heavy ($V_H$) and light ($V_L$) chains as indicated in Tables 1 and 2. The specific sequences referred to by these SEQ ID NOs. are shown in FIG. 1. As indicated in Tables 1 and 2, the corresponding $V_H$ and $V_L$ amino acid and DNA sequences of the antibodies mentioned above are described by SEQ ID NOs: 1-23, 68-90, and 320-343.

TABLE 1

Human P-cadherin antibodies

| | Sequence Identifier (SEQ ID NO:) | | | |
|---|---|---|---|---|
| | $V_H$ | | $V_L$ | |
| Antibody | Amino acid | DNA | Amino acid | DNA |
| 194-e06 | 1 | 68 | 14 | 81 |
| 194-a02 | 2 | 69 | 14 | 81 |
| 194-b09 | 2 | 69 | 15 | 82 |
| 195-e11 | 3 | 70 | 16 | 83 |
| 194-g09 | 4 | 71 | 17 | 84 |
| 196-h02 | 4 | 71 | 23 | 90 |
| 194-e01 | 5 | 72 | 18 | 85 |
| 196-d10 | 6 | 73 | 23 | 90 |
| 196-g03 | 7 | 74 | 23 | 90 |
| 196-e06 | 8 | 75 | 23 | 90 |
| 195-a09 | 9 | 76 | 23 | 90 |
| 198-a09 | 10 | 77 | 19 | 86 |
| 200-h06 | 11 | 78 | 20 | 87 |
| 129-1c4 | 12 | 79 | 21 | 88 |

TABLE 2

Germlined Human P-cadherin antibodies

| | Sequence Identifier (SEQ ID NO:) | | | |
|---|---|---|---|---|
| | $V_H$ | | $V_L$ | |
| Antibody | Amino acid | DNA | Amino acid | DNA |
| g-194-b09 | 320 | 332 | 326 | 338 |
| g-194-g09 | 321 | 333 | 327 | 339 |
| g-196-g03 | 322 | 334 | 328 | 340 |
| g-196-h02 | 323 | 335 | 329 | 341 |
| g-194-e01 | 324 | 336 | 330 | 342 |
| g-194-e06 | 325 | 337 | 331 | 343 |
| g-129-1c4 | 13 | 80 | 22 | 89 |

Additional antibodies and antigen-binding portions of the present invention can also be described as comprising the various CDR and FR sequences that make up the heavy and light chain variable regions of the antibodies indicated in Tables 1 and 2. Accordingly, SEQ ID NOs. that correspond to various CDR and FR sequences of antibodies of the present invention are indicated in Table 3. Furthermore, numerous randomized mutations in the heavy and light chain CDR3 regions of the 129-1c4 parent antibody were also performed, which yielded improved P-cadherin affinity ranging from 10- to 417-fold improvement as measured by an epitope competition assay (see Example 8). The SEQ ID NOs. of these mutated $V_H$ and $V_L$ CDR3 sequences (SEQ ID NOs: 91-256, and 257-319) are also included in Table 3 below.

TABLE 3

| SEQ ID NOs: | Description |
|---|---|
| 24 | $V_H$ CDR1 |
| 25 | $V_H$ CDR2 |
| 26-37, 91-256 | $V_H$ CDR3 |
| 38 | $V_L$ CDR1 |
| 39 | $V_L$ CDR2 |
| 40-47, 257-319 | $V_L$ CDR3 |
| 48 | $V_H$ FR1 |
| 49 | $V_H$ FR2 |
| 50-55 | $V_H$ FR3 |
| 56, 57 | $V_H$ FR4 |
| 58, 59 | $V_L$ FR1 |
| 60-62 | $V_L$ FR2 |
| 63-66 | $V_L$ FR3 |
| 67 | $V_L$ FR4 |

Methods of Producing Antibodies

Phage Display Libraries

The antibodies or antigen-binding portions of the present invention can be prepared according to several methods known in the art. For example, phage display techniques can be used to provide libraries containing a repertoire of antibodies with varying affinities for P-cadherin. These libraries can then be screened to identify and isolate antibodies with the desired affinity for P-cadherin.

For example, recombinant human P-cadherin antibodies of the present invention can be isolated by screening a recombinant combinatorial antibody library. Preferably the library is a scFv phage display library, generated using human $V_L$ and $V_H$ cDNAs prepared from mRNA isolated from human B cells. Methods for preparing and screening such libraries are known in the art. Kits for generating phage display libraries are commercially available (e.g., the Pharmacia Recombinant Phage Antibody System, catalog no. 27-9400-01; and the Stratagene SurfZAP™ phage display kit, catalog no. 240612). There are also other methods and reagents that can be used in generating and screening antibody display libraries (see, e.g., U.S. Pat. No. 5,223,409; PCT Publication Nos. WO 92/18619, WO 91/17271, WO 92/20791, WO 92/15679, WO 93/01288, WO 92/01047, and WO 92/09690; Fuchs et al., Bio/Technology 9:1370-1372 (1991); Hay, et al., Hum. Antibod. Hybridomas, 3:81-85 (1992); Huse, et al., Science, 246: 1275-1281 (1989); McCafferty et al., Nature, 348:552-554 (1990); Griffiths, et al., EMBO J., 12:725-734 (1993); Hawkins, et al., J. Mol. Biol., 226:889-896 (1992); Clackson, et al., Nature 352:624-628 (1991); Gram, et al., Proc. Natl. Acad. Sci. USA, 89:3576-3580 (1992); Garrad, et al., Bio/Technology, 9:1373-1377 (1991); Hoogenboom, et al., Nuc. Acid Res., 19:4133-4137 (1991); Barbas, et al., Proc. Natl. Acad. Sci. USA, 88:7978-7982 (1991); and Griffiths, et al., EMBO J., 13:3245-3260 (1994); which are all incorporated herein by reference).

Another method for preparing a library of antibodies for use in phage display techniques comprises the steps of immunizing a non-human animal comprising human immunoglobulin loci with P-cadherin or an antigenic portion thereof to create an immune response, extracting antibody-producing cells from the immunized animal; isolating RNA encoding heavy and light chains of antibodies of the invention from the extracted cells, reverse transcribing the RNA to produce cDNA, amplifying the cDNA using primers, and inserting the cDNA into a phage display vector such that antibodies are expressed on the phage. For production of such repertoires, it is unnecessary to immortalize the B cells from the immunized animal. Rather, the primary B cells can be used directly as a source of DNA. The mixture of cDNAs obtained from B cells, e.g., derived from spleens, is used to prepare an expression library, for example, a phage display library transfected into E. coli. Ultimately, clones from the library are identified that produce binding affinities of a desired magnitude for the antigen and the DNA encoding the product responsible for such binding is recovered and manipulated for standard recombinant expression. Phage display libraries may also be constructed using previously manipulated nucleotide sequences and screened in a similar fashion. In general, the cDNAs encoding heavy and light chains are independently supplied or linked to form Fv analogs for production in the phage library. The phage library is then screened for the antibodies with the highest affinities for P-cadherin and the genetic material is recovered from the appropriate clone. Further rounds of screening can increase affinity of the original antibody isolated.

In one embodiment, to isolate and produce human P-cadherin antibodies with the desired characteristics, a human P-cadherin antibody as described herein is first used to select human heavy and light chain sequences having similar binding activity toward P-cadherin, using the epitope imprinting methods described in PCT Publication No. WO 93/06213, incorporated herein by reference. The antibody libraries used in this method are preferably scFv libraries prepared and screened as described in PCT Publication No. WO 92/01047, McCafferty, et al., *Nature*, 348:552-554 (1990); and Griffiths, et al., *EMBO J.* 12:725-734 (1993), all incorporated herein by reference. The scFv antibody libraries can be screened using human P-cadherin as the antigen. The phage library is screened for the antibodies with the highest affinities for P-cadherin and the genetic material recovered from the appropriate clone. Further rounds of screening can increase affinity of the original antibody isolated.

Once initial human $V_L$ and $V_H$ domains are selected, "mix and match" experiments can then be performed, in which different pairs of the initially selected $V_L$ and $V_H$ segments are screened for P-cadherin binding to select preferred $V_L/V_H$ pair combinations. These mix and match experiments can also be performed after the $V_H$ and $V_L$ segments have been randomly mutated for optimized binding as described below. Additionally, to further improve the quality of the antibody, the $V_L$ and $V_H$ segments of the preferred $V_L/V_H$ pair(s) can be randomly mutated, preferably within the CDR3 region of $V_H$ and/or $V_L$, in a process analogous to the in vivo somatic mutation process responsible for affinity maturation of antibodies during a natural immune response. This in vitro affinity maturation can be accomplished, for example, by amplifying $V_H$ and $V_L$ domains using PCR primers complimentary to the $V_H$ CDR3 or $V_L$ CDR3, respectively, which primers have been "spiked" with a random mixture of the four nucleotide bases at certain positions such that the resultant PCR products encode $V_H$ and $V_L$ segments into which random mutations have been introduced into the $V_H$ and/or $V_L$ CDR3 regions. These randomly mutated $V_H$ and $V_L$ segments can be re-screened for binding to P-cadherin, and sequences that exhibit high affinity and a low off rate for P-cadherin can be selected. As discussed previously, several $V_H$ and $V_L$ CDR3 sequences of the present invention that were randomly mutated and showed improved affinity are indicated by SEQ ID NOs: 91-256 and 257-319.

Following screening and isolation of a P-cadherin antibody of the invention from a recombinant immunoglobulin display library, nucleic acids encoding the selected antibody can be recovered from the display package (e.g., from the phage genome) and subcloned into other expression vectors by standard recombinant DNA techniques. If desired, the nucleic acid can further be manipulated to create other antibody forms of the invention, as described below. To express a recombinant human antibody isolated by screening of a combinatorial library, the DNA encoding the antibody is cloned into a recombinant expression vector and introduced into a host cell, as described below.

Immunization

In another embodiment, human P-cadherin antibodies can be produced by immunizing a non-human, transgenic animal comprising within its genome some or all of human immunoglobulin heavy chain and light chain loci with a P-cadherin antigen. For example, the non-human animal can be a XENOMOUSE™ animal. (Abgenix, Inc., Fremont, Calif.).

XENOMOUSE™ mice are engineered mouse strains that comprise large fragments of human immunoglobulin heavy chain and light chain loci and are deficient in mouse antibody production. See, e.g., Green, et al., *Nature Genetics*, 7:13-21 (1994) and U.S. Pat. Nos. 5,916,771, 5,939,598, 5,985,615, 5,998,209, 6,075,181, 6,091,001, 6,114,598, 6,130,364, 6,162,963 and 6,150,584. See also WO 91/10741, WO 94/02602, WO 96/34096, WO 96/33735, WO 98/16654, WO 98/24893, WO 98/50433, WO 99/45031, WO 99/53049, WO 00/09560, and WO 00/037504.

The methods disclosed in these documents can be modified as described in U.S. Pat. No. 5,994,619, which is hereby incorporated by reference. U.S. Pat. No. 5,994,619 describes methods for producing novel cultured inner cell mass (CICM) cells and cell lines, derived from pigs and cows, and transgenic CICM cells into which heterologous DNA has been inserted. CICM transgenic cells can be used to produce cloned transgenic embryos, fetuses, and offspring. The '619 patent also describes methods of producing transgenic animals that are capable of transmitting the heterologous DNA to their progeny. Examples of non-human animals that can be used with these methods include rats, sheep, pigs, goats, cattle, chicken, and horses.

XENOMOUSE™ mice produce an adult-like human repertoire of fully human antibodies and generate antigen-specific human antibodies. In some embodiments, the XENOMOUSE™ mice contain approximately 80% of the human antibody V gene repertoire through introduction of megabase sized, germline configuration fragments of the human heavy chain loci and kappa light chain loci in yeast artificial chromosome (YAC). In other embodiments, XENOMOUSE™ mice further contain approximately all of the human lambda light chain locus. See Mendez, et al., *Nature Genetics*, 15:146-156 (1997), Green and Jakobovits, *J. Exp. Med.*, 188: 483-495 (1998), and WO 98/24893, the disclosures of which are hereby incorporated by reference.

In some embodiments, the non-human animal comprising human immunoglobulin genes are animals that have a human immunoglobulin "minilocus". In the minilocus approach, an exogenous Ig locus is mimicked through the inclusion of individual genes from the Ig locus. Thus, one or more $V_H$ genes, one or more $D_H$ genes, one or more $J_H$ genes, a mu constant domain, and a second constant domain (preferably a gamma constant domain) are formed into a construct for insertion into an animal. This approach is described in U.S. Pat. Nos. 5,545,807, 5,545,806, 5,569,825, 5,625,126, 5,633, 425, 5,661,016, 5,770,429, 5,789,650, 5,814,318, 5,591,669, 5,612,205, 5,721,367, 5,789,215, and 5,643,763, hereby incorporated by reference.

Non-human animals as described above can then be immunized with a P-cadherin antigen as described below under conditions that permit antibody production. Antibody-producing cells are isolated from the animals, and nucleic acids encoding the heavy and light chains of P-cadherin antibody of interest are isolated from the isolated antibody-producing cells or from an immortalized cell line produced from such cells. These nucleic acids are subsequently engineered using techniques known to those of skill in the art and as described further below to reduce the amount of non-human sequence, i.e., to humanize the antibody to reduce the immune response in humans.

In some embodiments, the P-cadherin antigen can be isolated and/or purified P-cadherin. In some embodiments, the P-cadherin antigen is human P-cadherin. In other embodiments, the P-cadherin antigen can be a cell that expresses or over-expresses P-cadherin. In other embodiments, the P-cadherin antigen is a recombinant protein expressed from yeast, insect cells, bacteria such as E. coli, or other resources by recombinant technology. Immunization of animals can be by any method known in the art. See, e.g., Harlow and Lane, *Antibodies: A Laboratory Manual*, New York: Cold Spring Harbor Press (1990). Methods for immunizing non-human animals such as mice, rats, sheep, goats, pigs, cattle and horses are well known in the art. See, e.g., Harlow and Lane, supra, and U.S. Pat. No. 5,994,619. For example, the P-cadherin antigen can be administered with an adjuvant to stimulate the immune response. Exemplary adjuvants include complete or incomplete Freund's adjuvant, RIBI (muramyl dipeptides) or ISCOM (immunostimulating complexes). Such adjuvants may protect the polypeptide from rapid dispersal by sequestering it in a local deposit, or they may contain substances that stimulate the host to secrete factors that are chemotactic for macrophages and other components of the immune system. Preferably, if a polypeptide is being administered, the immunization schedule will involve two or more administrations of the polypeptide, spread out over several weeks.

For example, following immunization of a transgenic animal as described above with P-cadherin, primary cells (e.g. spleen or peripheral blood B cells) can be isolated from the immunized transgenic animal and individual cells producing antibodies specific for the desired antigen can be identified. Polyadenylated mRNA from each individual cell is then isolated and reverse transcription polymerase chain reaction (RT-PCR) is performed using sense primers that anneal to variable region sequences (e.g., degenerate primers that recognize most or all of the FR1 regions of human heavy and light chain variable region genes and anti-sense primers that anneal to constant or joining region sequences). cDNAs of the heavy and light chain variable domains are then cloned and expressed in any suitable host cell, e.g., a myeloma cell, as chimeric antibodies with respective immunoglobulin constant regions, such as the heavy chain and K or A constant domains. See Babcook, et al., *Proc. Natl. Acad. Sci. USA*, 93:7843-48, (1996), incorporated herein by reference. P-cadherin antibodies may then be identified and isolated as described herein.

Recombinant Methods of Producing Antibodies

An antibody, or antibody portion, of the invention can be prepared by recombinant expression of immunoglobulin light and heavy chain genes in a host cell. For example, to express an antibody recombinantly, a host cell is transfected with one or more recombinant expression vectors carrying DNA fragments encoding the immunoglobulin light and heavy chains of the antibody such that the light and heavy chains are expressed in the host cell and, preferably, secreted into the medium in which the host cells are cultured, from which medium the antibodies can be recovered. Standard recombinant DNA methodologies are used to obtain antibody heavy and light chain genes, to incorporate these genes into recombinant expression vectors and to introduce the vectors into host cells, such as those described in Sambrook, Fritsch and Maniatis (eds), *Molecular Cloning; A Laboratory Manual, Second Edition*, Cold Spring Harbor, N.Y., (1989), Ausubel, F. M., et al. (eds.) *Current Protocols in Molecular Biology*, Greene Publishing Associates, (1989) and in U.S. Pat. No. 4,816,397, the disclosures of which are incorporated herein by reference.

Mutations and Modifications

To express the P-cadherin antibodies of the present invention, DNA fragments encoding $V_H$ and $V_L$ regions can first be obtained using any of the methods described above. Various mutations, deletions, and/or additions can also be introduced into the DNA sequences using standard methods known to those of skill in the art. For example, mutagenesis can be carried out using standard methods, such as PCR-mediated mutagenesis, in which the mutated nucleotides are incorporated into the PCR primers such that the PCR product contains the desired mutations or site-directed mutagenesis. One type of substitution, for example, that may be made is to change one or more cysteines in the antibody, which may be chemically reactive, to another residue, such as, without limitation, alanine or serine. For example, there can be a substitution of a non-canonical cysteine. The substitution can be made in a CDR or framework region of a variable domain or in the constant domain of an antibody. In some embodiments, the cysteine is canonical.

The antibodies may also be mutated in the variable domains of the heavy and/or light chains, e.g., to alter a binding property of the antibody. For example, a mutation may be made in one or more of the CDR regions to increase or decrease the $K_D$ of the antibody for P-cadherin, to increase or decrease $k_{off}$, or to alter the binding specificity of the antibody. Techniques in site-directed mutagenesis are well-known in the art. See, e.g., Sambrook, et al. and Ausubel, et al., supra, which is incorporated herein by reference. For example, as discussed in greater detail in Example 8, numerous variant $V_H$ and $V_L$ CDR3 sequences of the 129-1c4 parent were made according to the procedures discussed above, and are indicated as SEQ ID NOs: 91 to 256 ($V_H$ CDR3 variants) and SEQ ID NOs: 257 to 319 ($V_L$ CDR3 variants) in FIG. 1.

A mutation may also be made in a framework region or constant domain to increase the half-life of a P-cadherin antibody. See, e.g., PCT Publication No. WO 00/09560, incorporated herein by reference. A mutation in a framework region or constant domain can also be made to alter the immunogenicity of the antibody, to provide a site for covalent or non-covalent binding to another molecule, or to alter such properties as complement fixation, FcR binding and antibody-dependent cell-mediated cytotoxicity (ADCC). According to the invention, a single antibody may have mutations in any one or more of the CDRs or framework regions of the variable domain or in the constant domain.

In a process known as "germlining", certain amino acids in the $V_H$ and $V_L$ sequences can be mutated to match those found naturally in germline $V_H$ and $V_L$ sequences. In particular, the amino acid sequences of the framework regions in the $V_H$ and $V_L$ sequences can be mutated to match the germline sequences to reduce the risk of immunogenicity when the antibody is administered. Germline DNA sequences for human $V_H$ and $V_L$ genes are known in the art (see e.g., the "Vbase" human germline sequence database; see also Kabat, E. A., et al. (1991) *Sequences of Proteins of Immunological Interest, Fifth Edition*, U.S. Department of Health and Human Services, NIH Publication No. 91-3242; Tomlinson, et al. (1992) *J. Mol. Biol.* 227:776-798; and Cox, et al. *Eur. J. Immunol.* 24:827-836 (1994); the contents of each of which are expressly incorporated herein by reference).

Another type of amino acid substitution that may be made is to remove potential proteolytic sites in the antibody. Such sites may occur in a CDR or framework region of a variable domain or in the constant domain of an antibody. Substitution of cysteine residues and removal of proteolytic sites may decrease the risk of heterogeneity in the antibody product and thus increase its homogeneity. Another type of amino acid substitution is to eliminate asparagine-glycine pairs, which form potential deamidation sites, by altering one or both of the residues. In another example, the C-terminal lysine of the heavy chain of a P-cadherin antibody of the invention can be cleaved. In various embodiments of the invention, the heavy and light chains of the P-cadherin antibodies may optionally include a N-terminal signal sequence, such as those indicated by SEQ ID NOs: 346 and 347.

Once DNA fragments encoding the $V_H$ and $V_L$ segments of the present invention are obtained, these DNA fragments can be further manipulated by standard recombinant DNA techniques, for example to convert the variable region genes to full-length antibody chain genes, to Fab fragment genes, or to a scFv gene. In these manipulations, a $V_L$- or $V_H$-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the $V_H$ region can be converted to a full-length heavy chain gene by operatively linking the $V_H$-encoding DNA to another DNA molecule encoding heavy chain constant regions ($CH_1$, $CH_2$ and $CH_3$). The sequences of human heavy chain constant region genes are known in the art (see e.g., Kabat, E. A., et al. (1991) *Sequences of Proteins of Immunological Interest*, Fifth Ed., U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 or IgG2 constant region. The IgG1 constant region sequence can be any of the various alleles or allotypes known to occur among different individuals, such as Gm(1), Gm(2), Gm(3), and Gm(17). These allotypes represent naturally occurring amino acid substitution in the IgG1 constant regions. For example, the heavy chain IgG1 constant region can be SEQ ID NO: 344. For a Fab fragment heavy chain gene, the $V_H$-encoding DNA can be operatively linked to another DNA molecule encoding only the heavy chain CH1 constant region. The CH1 heavy chain constant region may be derived from any of the heavy chain genes.

The isolated DNA encoding the $V_L$ region can be converted to a full-length light chain gene (as well as a Fab light chain gene) by operatively linking the $V_L$-encoding DNA to another DNA molecule encoding the light chain constant region, $C_L$. The sequences of human light chain constant region genes are known in the art (see e.g., Kabat, E. A., et al. (1991) *Sequences of Proteins of Immunological Interest*, Fifth Ed., U.S. Department of Health and Human Services, NIH Publication No. 91-3242) and DNA fragments encompassing these regions can be obtained by standard PCR amplification. The light chain constant region can be a kappa or lambda constant region. The kappa constant region may be any of the various alleles known to occur among different individuals, such as Inv(1), Inv(2), and Inv(3). The lambda constant region may be derived from any of the three lambda genes. For example the light chain IgG1 constant region can be SEQ ID NO: 347.

To create a scFv gene, the $V_H$- and $V_L$-encoding DNA fragments are operatively linked to another fragment encoding a flexible linker, e.g., encoding the amino acid sequence $(Gly_4$-$Ser)_3$, such that the $V_H$ and $V_L$ sequences can be expressed as a contiguous single-chain protein, with the $V_L$ and $V_H$ regions joined by the flexible linker (see e.g., Bird et al. *Science* 242:423-426 (1988); Huston et al. *Proc. Natl. Acad. Sci. USA* 85:5879-5883 (1988); McCafferty, et al., *Nature*, 348:552-554 (1990)). The single chain antibody may be monovalent, if only a single $V_H$ and $V_L$ are used, bivalent, if two $V_H$ and $V_L$ are used, or polyvalent, if more than two $V_H$ and $V_L$ are used. Bispecific or polyvalent antibodies may be generated that bind specifically to P-cadherin and to another molecule.

In another embodiment, a fusion antibody or immunoadhesin may be made that comprises all or a portion of a P-cadherin antibody of the invention linked to another polypeptide. In another embodiment, only the variable domains of the P-cadherin antibody are linked to the polypeptide. In another embodiment, the $V_H$ domain of a P-cadherin antibody is linked to a first polypeptide, while the $V_L$ domain of a P-cadherin antibody is linked to a second polypeptide that associates with the first polypeptide in a manner such that the $V_H$ and $V_L$ domains can interact with one another to form an antigen binding site. In another preferred embodiment, the $V_H$ domain is separated from the $V_L$ domain by a linker such that the $V_H$ and $V_L$ domains can interact with one another. The $V_H$-linker-$V_L$ antibody is then linked to the polypeptide of interest. In addition, fusion antibodies can be created in which two (or more) single-chain antibodies are linked to one another. This is useful if one wants to create a divalent or polyvalent antibody on a single polypeptide chain, or if one wants to create a bispecific antibody.

In other embodiments, other modified antibodies may be prepared using P-cadherin antibody encoding nucleic acid molecules. For instance, "Kappa bodies" (Ill, et al., *Protein Eng.* 10: 949-57 (1997)), "Minibodies" (Martin, et al., *EMBO J.*, 13: 5303-9 (1994)), "Diabodies" (Holliger, et al., *Proc. Natl. Acad. Sci. USA*, 90: 6444-6448 (1993)), or "Janusins" (Traunecker, et al., *EMBO J.*, 10:3655-3659 (1991) and Traunecker, et al., *Int. J. Cancer*, (Suppl.) 7:51-52 (1992)) may be prepared using standard molecular biological techniques following the teachings of the specification.

Bispecific antibodies or antigen-binding fragments can be produced by a variety of methods including fusion of hybridomas or linking of Fab' fragments. See, e.g., Songsivilai & Lachmann, *Clin. Exp. Immunol.*, 79:315-321 (1990), Kostelny, et al., *J. Immunol.*, 148:1547-1553 (1992). In addition, bispecific antibodies may be formed as "diabodies" or "Janusins." In some embodiments, the bispecific antibody binds to two different epitopes of P-cadherin. In some embodiments, the modified antibodies described above are prepared using one or more of the variable domains or CDR regions from a human P-cadherin antibody provided herein.

Vectors and Host Cells

To express the antibodies and antigen-binding portions of the invention, DNAs encoding partial or full-length light and heavy chains, obtained as described above, are inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. Expression vectors include plasmids, retroviruses, adenoviruses, adeno-associated viruses (AAV), plant viruses such as cauliflower mosaic virus, tobacco mosaic virus, cosmids, YACs, EBV derived episomes, and the like. The antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vectors. In a preferred embodiment, both genes are inserted into the same expression vector. The antibody genes are inserted into the expression vector by standard methods (e.g., ligation of complementary restriction sites on the antibody gene fragment and vector, or blunt end ligation if no restriction sites are present).

A convenient vector is one that encodes a functionally complete human $C_H$ or $C_L$ immunoglobulin sequence, with appropriate restriction sites engineered so that any $V_H$ or $V_L$ sequence can easily be inserted and expressed, as described above. In such vectors, splicing usually occurs between the splice donor site in the inserted J region and the splice acceptor site preceding the human C domain, and also at the splice regions that occur within the human $C_H$ exons. Polyadenylation and transcription termination occur at native chromosomal sites downstream of the coding regions. The recombinant expression vector also can encode a signal peptide that facilitates secretion of the antibody chain from a host cell. The antibody chain gene may be cloned into the vector such that the signal peptide is linked in-frame to the amino terminus of the immunoglobulin chain. The signal peptide can be an immunoglobulin signal peptide or a heterologous signal peptide (i.e., a signal peptide from a non-immunoglobulin protein).

In addition to the antibody chain genes, the recombinant expression vectors of the invention carry regulatory sequences that control the expression of the antibody chain genes in a host cell. It will be appreciated by those skilled in the art that the design of the expression vector, including the selection of regulatory sequences may depend on such factors as the choice of the host cell to be transformed, the level of expression of protein desired, and so forth. Preferred regulatory sequences for mammalian host cell expression include viral elements that direct high levels of protein expression in mammalian cells, such as promoters and/or enhancers derived from retroviral LTRs, cytomegalovirus (CMV) (such as the CMV promoter/enhancer), Simian Virus 40 (SV40) (such as the SV40 promoter/enhancer), adenovirus, (e.g., the adenovirus major late promoter (AdMLP)), polyoma and strong mammalian promoters such as native immunoglobulin and actin promoters. For further description of viral regulatory elements, and sequences thereof, see e.g., U.S. Pat. No. 5,168,062, U.S. Pat. No. 4,510,245 and U.S. Pat. No. 4,968,615. Methods for expressing antibodies in plants, including a description of promoters and vectors, as well as transformation of plants is known in the art. See, e.g., U.S. Pat. No. 6,517,529, incorporated herein by reference. Methods of expressing polypeptides in bacterial cells or fungal cells, e.g., yeast cells, are also well known in the art.

In addition to the antibody chain genes and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216, 4,634,665 and 5,179,017, incorporated herein by reference). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification), the neomycin phosphotransferase gene (for G418 selection), and the glutamate synthetase gene.

Nucleic acid molecules encoding P-cadherin antibodies and vectors comprising these nucleic acid molecules can be used for transfection of a suitable mammalian, plant, bacterial or yeast host cell. Transformation can be by any known method for introducing polynucleotides into a host cell. Methods for introduction of heterologous polynucleotides into mammalian cells are well known in the art and include dextran-mediated transfection, calcium phosphate precipitation, polybrene-mediated transfection, protoplast fusion, electroporation, encapsulation of the polynucleotide(s) in liposomes, and direct microinjection of the DNA into nuclei. In addition, nucleic acid molecules may be introduced into mammalian cells by viral vectors. Methods of transforming cells are well known in the art. See, e.g., U.S. Pat. Nos. 4,399,216, 4,912,040, 4,740,461, and 4,959,455, incorporated herein by reference). Methods of transforming plant cells are well known in the art, including, e.g., *Agrobacterium*-mediated transformation, biolistic transformation, direct injection, electroporation and viral transformation. Methods of transforming bacterial and yeast cells are also well known in the art.

Mammalian cell lines available as hosts for expression are well known in the art and include many immortalized cell lines available from the American Type Culture Collection (ATCC). These include, for example, Chinese hamster ovary (CHO) cells, NSO cells, SP2 cells, HEK-293T cells, NIH-3T3 cells, HeLa cells, baby hamster kidney (BHK) cells, African green monkey kidney cells (COS), human hepatocellular carcinoma cells (e.g., Hep G2), A549 cells, and a number of other cell lines. Cell lines of particular preference are selected through determining which cell lines have high expression levels. Other cell lines that may be used are insect cell lines, such as Sf9 or Sf21 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods. Plant host cells include, e.g., *Nicotiana, Arabidopsis*, duckweed, corn, wheat, potato, and so forth. Bacterial host cells include *E. coli* and *Streptomyces* species. Yeast host cells include *Schizosaccharomyces pombe, Saccharomyces cerevisiae* and *Pichia pastoris*.

Further, expression of antibodies of the invention from production cell lines can be enhanced using a number of known techniques. For example, the glutamine synthetase (the GS system) and DHFR gene expression systems are common approaches for enhancing expression under certain conditions. High expressing cell clones can be identified using conventional techniques, such as limited dilution cloning and Microdrop technology. The GS system is discussed in European Patent Nos. 0 216 846, 0 256 055, 0 323 997 and 0 338 841.

It is likely that antibodies expressed by different cell lines or in transgenic animals will have different glycosylation from each other. However, all antibodies encoded by the nucleic acid molecules provided herein, or comprising the amino acid sequences provided herein are part of the present invention, regardless of the glycosylation of the antibodies.

Transgenic Animals and Plants

P-cadherin antibodies of the invention also can be produced transgenically through the generation of a mammal or plant that is transgenic for the immunoglobulin heavy and light chain sequences of interest and production of the antibody in a recoverable form therefrom. In connection with the transgenic production in mammals, P-cadherin antibodies can be produced in, and recovered from, the milk of goats, cows, or other mammals. See, e.g., U.S. Pat. Nos. 5,827,690, 5,756,687, 5,750,172, and 5,741,957, incorporated herein by reference. In some embodiments, non-human transgenic animals that comprise human immunoglobulin loci are immunized with P-cadherin or an immunogenic portion thereof, as described above. Methods for making antibodies in plants are described, e.g., in U.S. Pat. Nos. 6,046,037 and 5,959,177, incorporated herein by reference.

In some embodiments, non-human transgenic animals or plants are produced by introducing one or more nucleic acid molecules encoding a P-cadherin antibody, or antigen binding portion thereof, of the invention into the animal or plant by standard transgenic techniques. See Hogan and U.S. Pat. No. 6,417,429, supra. The transgenic cells used for making the transgenic animal can be embryonic stem cells or somatic cells or a fertilized egg. The transgenic non-human organisms can be chimeric, nonchimeric heterozygotes, and nonchimeric homozygotes. See, e.g., Hogan et al., *Manipulating the Mouse Embryo: A Laboratory Manual, 2$^{nd}$* ed., Cold Spring Harbor Press (1999); Jackson, et al., *Mouse Genetics and Transgenics: A Practical Approach*, Oxford University Press (2000); and Pinkert, *Transgenic Animal Technology: A Laboratory Handbook*, Academic Press (1999), all incorporated herein by reference. In some embodiments, the transgenic non-human animals have a targeted disruption and replacement by a targeting construct that encodes a heavy chain and/or a light chain of interest. The P-cadherin antibodies may be made in any transgenic animal. In a preferred embodiment, the non-human animals are mice, rats, sheep, pigs, goats, cattle or horses. The non-human transgenic animal expresses said encoded polypeptides in blood, milk, urine, saliva, tears, mucus and other bodily fluids.

Class Switching

The class (e.g. IgG, IgM, IgE, IgA, or IgD) and subclass (e.g. IgG1, IgG2, IgG3, or IgG4) of P-cadherin antibodies may be determined by any method known in the art. In general, the class and subclass of an antibody may be determined using antibodies that are specific for a particular class and subclass of antibody. Such antibodies are commercially available. The class and subclass can be determined by ELISA, or Western Blot as well as other techniques. Alternatively, the class and subclass may be determined by sequencing all or a portion of the constant domains of the heavy and/or light chains of the antibodies, comparing their amino acid sequences to the known amino acid sequences of various class and subclasses of immunoglobulins, and determining the class and subclass of the antibodies. The P-cadherin antibodies of the present invention can be an IgG, an IgM, an IgE, an IgA, or an IgD molecule. For example, the P-cadherin antibodies can be an IgG that is an IgG1, IgG2, IgG3, or an IgG4 subclass. In one embodiment, the P-cadherin antibodies can have a heavy chain constant region indicated by SEQ ID NO: 344 and a light chain constant region indicated by SEQ ID NO: 345.

One aspect of the invention provides a method for converting the class or subclass of a P-cadherin antibody to another class or subclass. In some embodiments, a nucleic acid molecule encoding a $V_L$ or $V_H$ that does not include sequences encoding $C_L$ or $C_H$ is isolated using methods well-known in the art. The nucleic acid molecule then is operatively linked to a nucleic acid sequence encoding a $C_L$ or $C_H$ from a desired immunoglobulin class or subclass. This can be achieved using a vector or nucleic acid molecule that comprises a $C_L$ or $C_H$ chain, as described above. For example, a P-cadherin antibody that was originally IgM can be class switched to an IgG. Further, the class switching may be used to convert one IgG subclass to another, e.g., from IgG1 to IgG2. Another method for producing an antibody of the invention comprising a desired isotype comprises the steps of isolating a nucleic acid encoding a heavy chain of a P-cadherin antibody and a nucleic acid encoding a light chain of a P-cadherin antibody, isolating the sequence encoding the $V_H$ region, ligating the $V_H$ sequence to a sequence encoding a heavy chain constant domain of the desired isotype, expressing the light chain gene and the heavy chain construct in a cell, and collecting the P-cadherin antibody with the desired isotype.

Deimmunized Antibodies

In another aspect of the invention, the antibodies or antigen binding portions thereof may be deimmunized to reduce their immunogenicity using the techniques described in, e.g., PCT Publication Nos. WO98/52976 and WO00/34317 (incorporated herein by reference).

Derivatized and Labeled Antibodies

A P-cadherin antibody or antigen-binding portion of the invention can be derivatized or linked to another molecule (e.g., another peptide or protein). In general, the antibodies or portion thereof are derivatized such that the P-cadherin binding is not affected adversely by the derivatization or labeling. Accordingly, the antibodies and antibody portions of the invention are intended to include both intact and modified forms of the human P-cadherin antibodies described herein. For example, an antibody or antibody portion of the invention can be functionally linked (by chemical coupling, genetic fusion, noncovalent association or otherwise) to one or more other molecular entities, such as another antibody (e.g., a bispecific antibody or a diabody), a detection agent, a label, a cytotoxic agent, a pharmaceutical agent, and/or a protein or peptide that can mediate association of the antibody or antibody portion with another molecule (such as a streptavidin core region or a polyhistidine tag).

One type of derivatized antibody is produced by crosslinking two or more antibodies (of the same type or of different types, e.g., to create bispecific antibodies). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill.

Another type of derivatized antibody is a labeled antibody. Useful detection agents with which an antibody or antigen-binding portion of the invention may be derivatized include fluorescent compounds, including fluorescein, fluorescein isothiocyanate, rhodamine, 5-dimethylamine-1-naphthalene-sulfonyl chloride, phycoerythrin, lanthanide phosphors, and the like. An antibody can also be labeled with enzymes that are useful for detection, such as horseradish peroxidase, β-galactosidase, luciferase, alkaline phosphatase, glucose oxidase, and the like. When an antibody is labeled with a detectable enzyme, it is detected by adding additional reagents that the enzyme uses to produce a reaction product that can be discerned. For example, when the agent horseradish peroxidase is present, the addition of hydrogen peroxide and diaminobenzidine leads to a colored reaction product, which is detectable. An antibody can also be labeled with biotin, and detected through indirect measurement of avidin or streptavidin binding. An antibody can also be labeled with a predetermined polypeptide epitope recognized by a secondary reporter (e.g., leucine zipper pair sequences, binding sites for secondary antibodies, metal binding domains, epitope tags). In some embodiments, labels are attached by spacer arms of various lengths to reduce potential steric hindrance. A P-cadherin antibody can also be derivatized with a chemical group such as polyethylene glycol (PEG), a methyl or ethyl group, or a carbohydrate group. These groups are useful to improve the biological characteristics of the antibody, e.g., to increase serum half-life.

Binding Affinity of P-Cadherin Antibodies to P-Cadherin

The binding affinity ($K_D$) and dissociation rate ($k_{off}$) of a P-cadherin antibody or antigen-binding portion thereof to P-cadherin can be determined by methods known in the art. The binding affinity can be measured by ELISAs, RIAs, flow cytometry, or surface plasmon resonance, such as BIACORE™. The dissociation rate can be measured by surface plasmon resonance. Preferably, the binding affinity and dissociation rate is measured by surface plasmon resonance. More preferably, the binding affinity and dissociation rate are measured using BIACORE™. One can determine whether an antibody has substantially the same $K_D$ as a P-cadherin antibody by using methods known in the art. Such methods of determining $K_D$ and $k_{off}$ can be used during the initial screening stage, as well as during subsequent optimization stages.

Identification of P-Cadherin Epitopes Recognized by P-Cadherin Antibodies

The invention provides human P-cadherin antibodies that bind to P-cadherin and compete or cross-compete with and/or binds the same epitope as any of the antibodies as described in Tables 1 or 2. One can determine whether an antibody binds to the same epitope or cross competes for binding with a P-cadherin antibody of the present invention by using methods known in the art. In one embodiment, one allows the P-cadherin antibody of the invention to bind to P-cadherin under saturating conditions and then measures the ability of the test antibody to bind to P-cadherin. If the test antibody is able to bind to P-cadherin at the same time as the P-cadherin antibody, then the test antibody binds to a different epitope as the P-cadherin antibody. However, if the test antibody is not able to bind to P-cadherin at the same time, then the test antibody binds to the same epitope, an overlapping epitope, or an epitope that is in close proximity to the epitope bound by the human P-cadherin antibody. This experiment can be performed using ELISA, RIA, BIACORE™, or flow cytometry. In a preferred embodiment, the experiment is performed using ELISA.

Inhibition of P-Cadherin Activity by P-Cadherin Antibody

P-cadherin antibodies that inhibit P-cadherin activity can be identified using a number of assays. A cell aggregation assay, for example, provides a method of measuring P-cadherin-dependent cellular aggregation. This type of assay uses a cell line that over-expresses P-cadherin, wherein the cells are placed into suspension and allowed to form P-cadherin-dependent aggregates. The aggregation assay is then used to quantify the ability of a P-cadherin antibody to prevent this aggregation by measuring the size of cellular aggregates that result with and without the antibody. Cell aggregate size as a function of P-cadherin antibody concentration can then be used to determine an $IC_{50}$ value. Example 4 provides further details of a P-cadherin-dependent aggregation assay that was used to measure $IC_{50}$ values for several P-cadherin antibodies.

Cell adhesion assays can also be used to measure the ability of a P-cadherin antibody to block the adhesion of cells to a receptor P-cadherin that has been immobilized on a solid support. This type of assay can be carried out, for example, by immobilizing P-cadherin on a solid support, such as plastic. Cells over-expressing P-cadherin are then allowed to adhere to the solid support via P-cadherin-P-cadherin interactions. The level of adhesion can then be quantified with and without a P-cadherin antibody. Adhesion as a function of antibody concentration is then used to determine an $IC_{50}$ value. Example 3 provides further details of a P-cadherin-dependent cell adhesion assay that was used to measure $IC_{50}$ values for P-cadherin antibodies.

Inhibition of P-cadherin activity can also be measured using a P-cadherin dependent spheroid disruption assay. This type of assay measures the ability of a P-cadherin antibody to disrupt pre-formed P-cadherin-dependent cellular aggregations. By measuring the size reduction of aggregates as a function of antibody concentration, an $IC_{50}$ value can be determined. Example 5 provides further details of a P-cadherin-dependent spheroid disruption assay that was used to measure $IC_{50}$ values for P-cadherin antibodies. The methods and assays described above for determining inhibition of P-cadherin activity by various antibodies or antigen-binding portions thereof can be used during the initial screening stage, as well as during subsequent optimization stages.

Molecular Selectivity

The selectivity of the P-cadherin antibodies of the present invention over other cadherins, such as E-cadherin, can be determined using methods well known in the art. For example one can determine the selectivity using Western blot, flow cytometry, ELISA, immunoprecipitation or RIA. Example 7 provides further details of an ELISA assay that was used to measure the selectivity of specific antibodies to P-cadherin over E-cadherin. The methods and assays described above for determining the selectivity for P-cadherin of various antibodies or antigen-binding portions thereof can be used during the initial screening stage, as well as during subsequent optimization stages.

Pharmaceutical Compositions and Administration

This invention also relates to a pharmaceutical composition for the treatment of abnormal cell growth in a mammal, including a human, comprising an amount of a P-cadherin antibody or antigen binding portion thereof, as described herein, that is effective in treating abnormal cell growth, and a pharmaceutically acceptable carrier.

The antibodies and antigen-binding portions of the present invention can be incorporated into pharmaceutical compositions suitable for administration to a subject. Typically, the pharmaceutical composition comprises an antibody or antigen-binding portion of the invention and a pharmaceutically acceptable carrier. As used herein, "pharmaceutically acceptable carrier" means any and all solvents, dispersion media, coatings, antibacterial and antifungal agents, isotonic and absorption delaying agents, and the like that are physiologically compatible. Some examples of pharmaceutically acceptable carriers are water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Additional examples of pharmaceutically acceptable substances are wetting agents or minor amounts of auxiliary substances such as wetting or emulsifying agents, preservatives or buffers, which enhance the shelf life or effectiveness of the antibody.

The compositions of this invention may be in a variety of forms, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans. The preferred mode of administration is parenteral (e.g., intravenous, subcutaneous, intraperitoneal, intramuscular). In a preferred embodiment, the antibody is administered by intravenous infusion or injection. In another preferred embodiment, the antibody is administered by intramuscular or subcutaneous injection. Formulations for injection may be presented in unit dosage form, e.g., in ampoules or in multi-dose containers, with or without an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the P-cadherin antibody in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The antibodies or antibody portions of the present invention can be administered by a variety of methods known in the art, although for many therapeutic applications, the preferred route/mode of administration is subcutaneous, intramuscular, or intravenous infusion. As will be appreciated by the skilled artisan, the route and/or mode of administration will vary depending upon the desired results.

In certain embodiments, the antibody compositions of the present invention may be prepared with a carrier that will protect the antibody against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are generally known to those skilled in the art. See, e.g., *Sustained and Controlled Release Drug Delivery Systems*, J. R. Robinson, ed., Marcel Dekker, Inc., New York, 1978, which is incorporated herein by reference.

Additional active compounds also can be incorporated into the compositions. In certain embodiments, an inhibitory P-cadherin antibody of the invention is co-formulated with and/or co-administered with one or more additional therapeutic agents. These agents include, without limitation, antibodies that bind other targets, anti-tumor agents, anti-angiogenesis agents, signal transduction inhibitors, anti-proliferative agents, chemotherapeutic agents, or peptide analogues that inhibit P-cadherin. Such combination therapies may require lower dosages of the inhibitory P-cadherin antibody as well as the co-administered agents, thus avoiding possible toxicities or complications associated with the various monotherapies.

The compositions of the invention may include a "therapeutically effective amount" or a "prophylactically effective amount" of an antibody or antigen-binding portion of the invention. A "therapeutically effective amount" refers to an amount effective, at dosages and for periods of time necessary, to achieve the desired therapeutic result. A therapeutically effective amount of the antibody or antigen-binding portion may vary according to factors such as the disease state, age, sex, and weight of the individual, and the ability of the antibody or antibody portion to elicit a desired response in the individual. A therapeutically effective amount is also one in which any toxic or detrimental effects of the antibody or antigen-binding portion are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount may be less than the therapeutically effective amount.

Dosage regimens can be adjusted to provide the optimum desired response (e.g., a therapeutic or prophylactic response). For example, a single bolus can be administered, several divided doses can be administered over time or the dose can be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the P-cadherin antibody or portion thereof and the particular therapeutic or prophylactic effect to be achieved, and (b) the limitations inherent in the art of compounding such an antibody for the treatment of sensitivity in individuals.

An exemplary, non-limiting range for a therapeutically or prophylactically effective amount of an antibody or antibody portion of the invention is 0.025 to 50 mg/kg, more preferably 0.1 to 50 mg/kg, more preferably 0.1-25, 0.1 to 10 or 0.1 to 3 mg/kg. In some embodiments, a formulation contains 5 mg/mL of antibody in a buffer of 20 mM sodium citrate, pH 5.5, 140 mM NaCl, and 0.2 mg/mL polysorbate 80. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

Another aspect of the present invention provides kits comprising a P-cadherin antibody or antigen-binding portion of the invention or a composition comprising such an antibody or portion. A kit may include, in addition to the antibody or composition, diagnostic or therapeutic agents. A kit can also include instructions for use in a diagnostic or therapeutic method. In a preferred embodiment, the kit includes the antibody or a composition comprising it and a diagnostic agent that can be used in a method described below. In another preferred embodiment, the kit includes the antibody or a composition comprising it and one or more therapeutic agents that can be used in a method described below.

Diagnostic Methods of Use

The P-cadherin antibodies or antigen-binding portions thereof can be used in diagnostic methods to detect P-cadherin in a biological sample in vitro or in vivo. For example, the P-cadherin antibodies can be used in a conventional immunoassay, including, without limitation, an ELISA, an RIA, flow cytometry, tissue immunohistochemistry, Western blot or immunoprecipitation. The P-cadherin antibodies of the invention can be used to detect P-cadherin from humans. The P-cadherin antibodies can also be used to detect P-cadherin from mice, rats, and cynomolgus monkeys.

The invention provides a method for detecting P-cadherin in a biological sample comprising contacting the biological sample with a P-cadherin antibody of the invention and detecting the bound antibody. In one embodiment, the P-cadherin antibody is directly labeled with a detectable label. In another embodiment, the P-cadherin antibody (the first antibody) is unlabeled and a second antibody or other molecule that can bind the P-cadherin antibody is labeled. As is well known to one of skill in the art, a second antibody is chosen that is able to specifically bind the particular species and class of the first antibody. For example, if the P-cadherin antibody is a human IgG, then the secondary antibody could be an anti-human-IgG. Other molecules that can bind to antibodies include, without limitation, Protein A and Protein G, both of which are available commercially, e.g., from Pierce Chemical Co.

Suitable labels for the antibody or secondary antibody have been discussed previously, and include various enzymes, prosthetic groups, fluorescent materials, luminescent materials and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include $^{125}$I, $^{131}$I, $^{35}$S or $^{3}$H.

In other embodiments, P-cadherin can be assayed in a biological sample by a competition immunoassay utilizing P-cadherin standards labeled with a detectable substance and an unlabeled P-cadherin antibody. In this assay, the biological sample, the labeled P-cadherin standards and the P-cadherin antibody are combined and the amount of labeled P-cadherin standard bound to the unlabeled antibody is determined. The amount of P-cadherin in the biological sample is inversely proportional to the amount of labeled P-cadherin standard bound to the P-cadherin antibody.

One can use the immunoassays disclosed above for a number of purposes. For example, the P-cadherin antibodies can be used to detect P-cadherin in cultured cells. In a preferred embodiment, the P-cadherin antibodies are used to determine the amount of P-cadherin produced by cells that have been treated with various compounds. This method can be used to identify compounds that modulate P-cadherin protein levels. According to this method, one sample of cells is treated with a test compound for a period of time while another sample is left untreated. If the total level of P-cadherin is to be measured, the cells are lysed and the total P-cadherin level is measured using one of the immunoassays described above. The total level of P-cadherin in the treated versus the untreated cells is compared to determine the effect of the test compound.

A preferred immunoassay for measuring total P-cadherin levels is flow cytometry or immunohistochemistry. Methods such as ELISA, RIA, flow cytometry, Western blot, immunohistochemistry, cell surface labeling of integral membrane proteins and immunoprecipitation are well known in the art. See, e.g., Harlow and Lane, supra. In addition, the immunoassays can be scaled up for high throughput screening in order to test a large number of compounds for either activation or inhibition of P-cadherin expression.

The P-cadherin antibodies of the invention also can be used to determine the levels of P-cadherin in a tissue or in cells derived from the tissue. In some embodiments, the tissue is a diseased tissue. In some embodiments of the method, a tissue or a biopsy thereof is excised from a patient. The tissue or biopsy is then used in an immunoassay to determine, e.g., total P-cadherin levels or localization of P-cadherin by the methods discussed above.

The antibodies of the present invention also can be used in vivo to identify tissues and organs that express P-cadherin. One advantage of using the human P-cadherin antibodies of the present invention is that they may safely be used in vivo without eliciting a substantial immune response to the antibody upon administration, unlike antibodies of non-human origin or with humanized or chimeric antibodies.

The method comprises the steps of administering a detectably labeled P-cadherin antibody or a composition comprising them to a patient in need of such a diagnostic test and subjecting the patient to imaging analysis to determine the location of the P-cadherin-expressing tissues. Imaging analysis is well known in the medical art, and includes, without limitation, x-ray analysis, magnetic resonance imaging (MRI) or computed tomography (CT). The antibody can be labeled with any agent suitable for in vivo imaging, for example a contrast agent, such as barium, which can be used for x-ray analysis, or a magnetic contrast agent, such as a gadolinium chelate, which can be used for MRI or CT. Other labeling agents include, without limitation, radioisotopes, such as $^{99}$Tc. In another embodiment, the P-cadherin antibody will be unlabeled and will be imaged by administering a second antibody or other molecule that is detectable and that can bind the P-cadherin antibody. In one embodiment, a biopsy is obtained from the patient to determine whether the tissue of interest expresses P-cadherin.

Therapeutic Methods of Use

In another embodiment, the invention provides a method for inhibiting P-cadherin activity by administering a P-cadherin antibody to a patient in need thereof. Any of the antibodies or antigen-binding portions thereof described herein may be used therapeutically. In a preferred embodiment, the P-cadherin antibody is a human, chimeric or humanized antibody. In another preferred embodiment, the P-cadherin is human and the patient is a human patient. Alternatively, the patient may be a mammal that expresses a P-cadherin that the P-cadherin antibody cross-reacts with. The antibody may be administered to a non-human mammal expressing P-cadherin with which the antibody cross-reacts (e.g. a rat, a mouse, or a cynomolgus monkey) for veterinary purposes or as an animal model of human disease. Such animal models may be useful for evaluating the therapeutic efficacy of antibodies of this invention.

In another embodiment, a P-cadherin antibody or antibody portion thereof may be administered to a patient who expresses inappropriately high levels of P-cadherin. The antibody may be administered once, but more preferably is administered multiple times. The antibody may be administered from three times daily to once every six months or longer. The administering may be on a schedule such as three times daily, twice daily, once daily, once every two days, once every three days, once weekly, once every two weeks, once every month, once every two months, once every three months and once every six months. The antibody may also be administered continuously via a minipump. The antibody may be administered via a mucosal, buccal, intranasal, inhalable, intravenous, subcutaneous, intramuscular, parenteral, or intratumor route. The antibody may be administered once, at least twice or for at least the period of time until the condition is treated, palliated or cured. The antibody generally will be administered for as long as the condition is present. The antibody will generally be administered as part of a pharmaceutical composition as described supra. The dosage of antibody will generally be in the range of 0.1 to 100 mg/kg, more preferably 0.5 to 50 mg/kg, more preferably 1 to 20 mg/kg, and even more preferably 1 to 10 mg/kg. The serum concentration of the antibody may be measured by any method known in the art.

This invention also relates to a method for the treatment of abnormal cell growth in a mammal, including a human, comprising administering to said mammal a therapeutically effective amount of a P-cadherin antibody or antigen binding portion thereof, as described herein, that is effective in treating abnormal cell growth.

In one embodiment of this method, the abnormal cell growth is cancer, including, but not limited to, mesothelioma, hepatobilliary (hepatic and billiary duct), a primary or secondary CNS tumor, a primary or secondary brain tumor, lung cancer (NSCLC and SCLC), bone cancer, pancreatic cancer, skin cancer, cancer of the head or neck, cutaneous or intraocular melanoma, ovarian cancer, colon cancer, rectal cancer, cancer of the anal region, stomach cancer, gastrointestinal (gastric, colorectal, and duodenal), breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, testicular cancer, chronic or acute leukemia, chronic myeloid leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, non hodgkins's lymphoma, spinal axis tumors, brain stem glioma, pituitary adenoma, adrenocortical cancer, gall bladder cancer, multiple myeloma, cholangiocarcinoma, fibrosarcoma, neuroblastoma, retinoblastoma, or a combination of one or more of the foregoing cancers.

In a preferred embodiment of the present invention the cancer is selected from lung cancer (NSCLC and SCLC), cancer of the head or neck, ovarian cancer, colon cancer, rectal cancer, cancer of the anal region, stomach cancer, breast cancer, cancer of the kidney or ureter, renal cell carcinoma, carcinoma of the renal pelvis, neoplasms of the central nervous system (CNS), primary CNS lymphoma, non hodgkins's lymphoma, spinal axis tumors, or a combination of one or more of the foregoing cancers.

In another preferred embodiment of the present invention the cancer is selected from lung cancer (NSCLC and SCLC), ovarian cancer, colon cancer, rectal cancer, cancer of the anal region, or a combination of one or more of the foregoing cancers.

In another embodiment of said method, said abnormal cell growth is a benign proliferative disease, including, but not limited to, psoriasis, benign prostatic hypertrophy or restinosis.

This invention also relates to a method for the treatment of abnormal cell growth in a mammal which comprises administering to said mammal an amount of a P-cadherin antibody or antigen binding portion thereof, as described herein, that is effective in treating abnormal cell growth in combination with an anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, antibodies, cytotoxics, anti-hormones, and anti-androgens.

The invention also relates to a pharmaceutical composition for the treatment of abnormal cell growth in a mammal, including a human, which comprises an amount of a P-cadherin antibody or antigen binding portion thereof, as described herein, that is effective in treating abnormal cell growth in combination with a pharmaceutically acceptable carrier and an anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, and anti-androgens.

This invention also relates to a method for the treatment of abnormal cell growth in a mammal which comprises administering to said mammal a P-cadherin antibody or antigen binding portion thereof, as described herein, in an amount that is effective in treating abnormal cell growth in combination with an anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, antibodies, cytotoxics, anti-hormones, and anti-androgens.

In one embodiment of the present invention the anti-tumor agent used in conjunction with a P-cadherin antibody of the present invention and pharmaceutical compositions described herein is an anti-angiogenesis agent, kinase inhibitor, pan kinase inhibitor or growth factor inhibitor. Preferred pan kinase inhibitors include Sutent™ (sunitinib), described in U.S. Pat. No. 6,573,293 (Pfizer, Inc, NY, USA). Anti-angiogenesis agents, include but are not limited to the following agents, such as EGF inhibitors, EGFR inhibitors, VEGF inhibitors, VEGFR inhibitors, TIE2 inhibitors, IGF1R inhibitors, COX-II (cyclooxygenase II) inhibitors, MMP-2 (matrix-metalloprotienase 2) inhibitors, and MMP-9 (matrix-metalloprotienase 9) inhibitors.

Preferred VEGF inhibitors, include for example, Avastin™ (bevacizumab), an anti-VEGF monoclonal antibody of Genentech, Inc. of South San Francisco, Calif. Additional VEGF inhibitors include CP-547,632 (Pfizer Inc., NY, USA), AG13736 (Pfizer Inc.), ZD-6474 (AstraZeneca), AEE788 (Novartis), AZD-2171, VEGF Trap (Regeneron/Aventis), Vatalanib (also known as PTK-787, ZK-222584: Novartis & Schering AG), Macugen™ (pegaptanib octasodium, NX-1838, EYE-001, Pfizer Inc./Gilead/Eyetech), IM862 (Cytran Inc. of Kirkland, Wash., USA); and angiozyme, a synthetic ribozyme from Ribozyme (Boulder, Colo.) and Chiron (Emeryville, Calif.) and combinations thereof.

VEGF inhibitors useful in the practice of the present invention are described in U.S. Pat. Nos. 6,534,524 and 6,235,764, both of which are incorporated in their entirety for all purposes. Additional VEGF inhibitors are described in, for example in WO 99/24440, in WO 95/21613, WO 99/61422, U.S. Pat. No. 5,834,504, WO 98/50356, U.S. Pat. No. 5,883,113 U.S. Pat. No. 5,886,020, U.S. Pat. No. 5,792,783, U.S. Pat. No. 6,653,308, WO 99/10349, WO 97/32856, WO 97/22596, WO 98/54093, WO 98/02438, WO 99/16755, and WO 98/02437, all of which are herein incorporated by reference in their entirety.

Other anti-angiogenic compounds include acitretin, fenretinide, thalidomide, zoledronic acid, angiostatin, aplidine, cilengtide, combretastatin A-4, endostatin, halofuginone, rebimastat, removab, Revlimid, squalamine, ukrain, Vitaxin and combinations thereof.

Other antiproliferative agents that may be used in combination with the antibodies of the present invention include inhibitors of the enzyme farnesyl protein transferase and inhibitors of the receptor tyrosine kinase PDGFr, including the compounds disclosed and claimed in the following: U.S. Pat. No. 6,080,769; U.S. Pat. No. 6,194,438; U.S. Pat. No. 6,258,824; U.S. Pat. No. 6,586,447; U.S. Pat. No. 6,071,935; U.S. Pat. No. 6,495,564; and U.S. Pat. No. 6,150,377; U.S. Pat. No. 6,596,735; U.S. Pat. No. 6,479,513; WO 01/40217; U.S. 2003-0166675. Each of the foregoing patents and patent applications is herein incorporated by reference in their entirety.

PDGRr inhibitors include but are not limited to those disclosed in international patent application publication numbers WO01/40217 and WO2004/020431, the contents of which are incorporated in their entirety for all purposes. Preferred PDGFr inhibitors include Pfizer's CP-673,451 and CP-868,596 and its salts.

Preferred GARF inhibitors include Pfizer's AG-2037 (pelitrexol and its salts). GARF inhibitors useful in the practice of the present invention are disclosed in U.S. Pat. No. 5,608,082 which is incorporated in its entirety for all purposes.

Examples of useful COX-II inhibitors which can be used in conjunction with the P-cadherin antibodies, and pharmaceutical compositions disclosed herein include CELEBREX™ (celecoxib), parecoxib, deracoxib, ABT-963, MK-663 (etoricoxib), COX-189 (Lumiracoxib), BMS 347070, RS 57067, NS-398, Bextra™ (valdecoxib), paracoxib, Vioxx™ (rofecoxib), SD-8381, 4-Methyl-2-(3,4-dimethylphenyl)-1-(4-sulfamoyl-phenyl)-1H-pyrrole, 2-(4-Ethoxyphenyl)-4-methyl-1-(4-sulfamoylphenyl)-1H-pyrrole, T-614, JTE-522, S-2474, SVT-2016, CT-3, SC-58125 and Arcoxia (etoricoxib). Additionally, COX-II inhibitors are disclosed in U.S. patent applications US 2005-0148627 and US 2005-0148777, the contents of which are incorporated in their entirety for all purposes.

In a particular embodiment the anti-tumor agent is celecoxib (U.S. Pat. No. 5,466,823), valdecoxib (U.S. Pat. No. 5,633,272), parecoxib (U.S. Pat. No. 5,932,598), deracoxib (U.S. Pat. No. 5,521,207), SD-8381 (U.S. Pat. No. 6,034,256, Example 175), ABT-963 (WO 2002/24719), rofecoxib (CAS No. 162011-90-7), MK-663 (or etoricoxib) as disclosed in WO 1998/03484, COX-189 (Lumiracoxib) as disclosed in WO 1999/11605, BMS-347070 (U.S. Pat. No. 6,180,651), NS-398 (CAS 123653-11-2), RS 57067 (CAS 17932-91-3), 4-Methyl-2-(3,4-dimethylphenyl)-1-(4-sulfamoyl-phenyl)-1H-pyrrole, 2-(4-Ethoxyphenyl)-4-methyl-1-(4-sulfamoylphenyl)-1H-pyrrole, or meloxicam.

Other useful inhibitors as anti-tumor agents used in combination with the antibodies of the present invention and pharmaceutical compositions disclosed herein include aspirin, and non-steroidal anti-inflammatory drugs (NSAIDs) which inhibit the enzyme that makes prostaglandins (cyclooxygenase I and II), resulting in lower levels of prostaglandins, include but are not limited to the following, Salsalate (Amigesic™) Diflunisal (Dolobid™), Ibuprofen (Motrin™), Ketoprofen (Orudis™), Nabumetone (Relafen™), Piroxicam (Feldene™), Naproxen (Aleve™, Naprosyn™), Diclofenac (Voltaren™), Indomethacin (Indocin™), Sulindac (Clinoril™), Tolmetin (Tolectin™), Etodolac (Lodine™), Ketorolac (Toradol™), Oxaprozin (Daypro™) and combinations thereof.

Preferred COX-I inhibitors include ibuprofen (Motrin™), nuprin, naproxen (Aleve™), indomethacin (Indocin™), nabumetone (Relafen™) and combinations thereof.

Targeted agents used in combination with antibodies of the present invention and pharmaceutical compositions disclosed herein include EGFr inhibitors such as Iressa™ (gefitinib, AstraZeneca), Tarceva™ (erlotinib or OSI-774, OSI Pharmaceuticals Inc.), Erbitux™ (cetuximab, Imclone Pharmaceuticals, Inc.), EMD-7200 (Merck AG), ABX-EGF (Amgen Inc. and Abgenix Inc.), HR3 (Cuban Government), IgA antibodies (University of Erlangen-Nuremberg), TP-38 (IVAX), EGFR fusion protein, EGF-vaccine, anti-EGFr immunoliposomes (Hermes Biosciences Inc.) and combinations thereof. Preferred EGFr inhibitors include Iressa™, Erbitux™, Tarceva™ and combinations thereof.

Other anti-tumor agents include those selected from pan erb receptor inhibitors or ErbB2 receptor inhibitors, such as CP-724,714 (Pfizer, Inc.), CI-1033 (canertinib, Pfizer, Inc.), Herceptin (trastuzumab, Genentech Inc.), Omitarg (2C4, pertuzumab, Genentech Inc.), TAK-165 (Takeda), GW-572016 (Ionafarnib, GlaxoSmithKline), GW-282974 (GlaxoSmithKline), EKB-569 (Wyeth), PKI-166 (Novartis), dHER2 (HER2Vaccine, Corixa and GlaxoSmithKline), APC8024 (HER2Vaccine, Dendreon), anti-HER2/neu bispecific antibody (Decof Cancer Center), B7.her2.IgG3 (Agensys), AS HER2 (Research Institute for Rad Biology & Medicine), trifunctional bispecific antibodies (University of Munich) and mAB AR-209 (Aronex Pharmaceuticals Inc) and mAB 2B-1 (Chiron) and combinations thereof.

Preferred erb selective anti-tumor agents include Herceptin™, TAK-165, CP-724,714, ABX-EGF, HER3 and combinations thereof. Preferred pan erbb receptor inhibitors include GW572016, CI-1033, EKB-569, and Omitarg and combinations thereof.

Additional erbB2 inhibitors include those disclosed in WO 98/02434, WO 99/35146, WO 99/35132, WO 98/02437, WO 97/13760, WO 95/19970, U.S. Pat. No. 5,587,458, and U.S. Pat. No. 5,877,305, each of which is herein incorporated by reference in its entirety. ErbB2 receptor inhibitors useful in the present invention are also disclosed in U.S. Pat. Nos. 6,465,449, and 6,284,764, and in WO 2001/98277 each of which are herein incorporated by reference in their entirety.

Additionally, other anti-tumor agents may be selected from the following agents, BAY-43-9006 (Onyx Pharmaceuticals Inc.), Genasense (augmerosen, Genta), Panitumumab (Abgenix/Amgen), Zevalin (Schering), Bexxar (Corixa/GlaxoSmithKline), Abarelix, Alimta, EPO 906 (Novartis), discodermolide (XAA-296), ABT-510 (Abbott), Neovastat™ (Aeterna), enzastaurin (Eli Lilly), Combrestatin A4P (Oxigene), ZD-6126 (AstraZeneca), flavopiridol (Aventis), CYC-202 (Cyclacel), AVE-8062 (Aventis), DMXAA (Roche/Antisoma), Thymitaq (Eximias), Temodar (temozolomide, Schering Plough) and Revilimd (Celegene) and combinations thereof.

Other anti-tumor agents may be selected from the following agents, CyPat (cyproterone acetate), Histerelin (histrelin acetate), Plenaixis (abarelix depot), Atrasentan (ABT-627), Satraplatin (JM-216), thalomid (Thalidomide), Theratope, Temilifene (DPPE), ABI-007 (paclitaxel), Evista (raloxifene), Atamestane (Biomed-777), Xyotax (polyglutamate paclitaxel), Targetin (bexarotine) and combinations thereof.

Additionally, other anti-tumor agents may be selected from the following agents, Trizaone (tirapazamine), Aposyn (exisulind), Nevastat (AE-941), Ceplene (histamine dihydrochloride), Orathecin (rubitecan), Virulizin, Gastrimmune (G17DT), DX-8951f (exatecan mesylate), Onconase (ranpirnase), BEC2 (mitumoab), Xcytrin (motexafin gadolinium) and combinations thereof.

Further anti-tumor agents may be selected from the following agents, CeaVac (CEA), NeuTrexin (trimetresate glucuronate) and combinations thereof. Additional anti-tumor agents may be selected from the following agents, OvaRex (oregovomab), Osidem (IDM-1), and combinations thereof. Additional anti-tumor agents may be selected from the following agents, Advexin (ING 201), Tirazone (tirapazamine), and combinations thereof. Additional anti-tumor agents may be selected from the following agents, RSR13 (efaproxiral), Cotara (131I chTNT 1/b), NBI-3001 (IL-4) and combinations thereof. Additional anti-tumor agents may be selected from the following agents, Canvaxin, GMK vaccine, PEG Interon A, Taxoprexin (DHA/paciltaxel), and combinations thereof.

Other anti-tumor agents include Pfizer's MEK1/2 inhibitor PD325901, Array Biopharm's MEK inhibitor ARRY-142886, Bristol Myers' CDK2 inhibitor BMS-387,032, Pfizer's CDK inhibitor PD0332991 and AstraZeneca's AXD-5438, and combinations thereof.

Additionally, mTOR inhibitors may also be utilized such as CCI-779 (Wyeth) and rapamycin derivatives RAD001 (Novartis) and AP-23573 (Ariad), HDAC inhibitors, SAHA (Merck Inc./Aton Pharmaceuticals) and combinations thereof. Additional anti-tumor agents include aurora 2 inhibitor VX-680 (Vertex), and Chk1/2 inhibitor XL844 (Exilixis).

The following cytotoxic agents, e.g., one or more selected from the group consisting of epirubicin (Ellence), docetaxel (Taxotere), paclitaxel, Zinecard (dexrazoxane), rituximab (Rituxan) imatinib mesylate (Gleevec™), and combinations thereof, may be used in combination with antibodies of the present invention and pharmaceutical compositions disclosed herein.

The invention also contemplates the use of the antibodies of the present invention together with hormonal therapy, including but not limited to, exemestane (Aromasin, Pfizer Inc.), leuprorelin (Lupron or Leuplin, TAP/Abbott/Takeda), anastrozole (Arimidex, Astrazeneca), gosrelin (Zoladex, AstraZeneca), doxercalciferol, fadrozole, formestane, tamoxifen citrate (tamoxifen, Nolvadex, AstraZeneca), Casodex (AstraZeneca), Abarelix (Praecis), Trelstar, and combinations thereof.

The invention also relates to the use of the antibodies of the present invention together with hormonal therapy agents such as anti-estrogens including, but not limited to fulvestrant, toremifene, raloxifene, lasofoxifene, letrozole (Femara, Novartis), anti-androgens such as bicalutamide, flutamide, mifepristone, nilutamide, Casodex™ (4'-cyano-3-(4-fluorophenylsulphonyl)-2-hydroxy-2-methyl-3'-(trifluoromethyl)propionanilide, bicalutamide) and combinations thereof.

Further, the invention provides an antibody of the present invention alone or in combination with one or more supportive care products, e.g., a product selected from the group consisting of Filgrastim (Neupogen), ondansetron (Zofran), Fragmin, Procrit, Aloxi, Emend, or combinations thereof.

Particularly preferred cytotoxic agents that can be used in combination with antibodies of the present invention include Camptosar, Erbitux, Iressa™, Gleevec™, Taxotere and combinations thereof.

The following topoisomerase I inhibitors may be utilized as anti-tumor agents in combination with antibodies of the present invention: camptothecin; irinotecan HCl (Camptosar); edotecarin; orathecin (Supergen); exatecan (Daiichi); BN-80915 (Roche); and combinations thereof. Particularly preferred toposimerase II inhibitors include epirubicin (Ellence).

Alkylating agents that can be used in combination with antibodies of the present invention include, but are not limited to, nitrogen mustard N-oxide, cyclophosphamide, ifosfamide, melphalan, busulfan, mitobronitol, carboquone, thiotepa, ranimustine, nimustine, temozolomide, AMD-473, altretamine, AP-5280, apaziquone, brostallicin, bendamustine, carmustine, estramustine, fotemustine, glufosfamide, ifosfamide, KW-2170, mafosfamide, and mitolactol; platinum-coordinated alkylating compounds include but are not limited to, cisplatin, Paraplatin (carboplatin), eptaplatin, lobaplatin, nedaplatin, Eloxatin (oxaliplatin, Sanofi) or satrplatin and combinations thereof. Particularly preferred alkylating agents include Eloxatin (oxaliplatin).

Antimetabolites that can be used in combination with antibodies of the present invention include but are not limited to, methotrexate, 6-mercaptopurine riboside, mercaptopurine, 5-fluorouracil (5-FU) alone or in combination with leucovorin, tegafur, UFT, doxifluridine, carmofur, cytarabine, cytarabine ocfosfate, enocitabine, S-1, Alimta (premetrexed disodium, LY231514, MTA), Gemzar (gemcitabine, Eli Lilly), fludarabin, 5-azacitidine, capecitabine, cladribine, clofarabine, decitabine, eflornithine, ethynylcytidine, cytosine arabinoside, hydroxyurea, TS-1, melphalan, nelarabine, nolatrexed, ocfosfate, disodium premetrexed, pentostatin, pelitrexol, raltitrexed, triapine, trimetrexate, vidarabine, vincristine, vinorelbine; or for example, one of the preferred anti-metabolites disclosed in European Patent Application No. 239362 such as N-(5-[N-(3,4-dihydro-2-methyl-4-oxoquinazolin-6-ylmethyl)-N-methylamino]-2-thenoyl)-L-glutamic acid and combinations thereof.

Antibiotics that can be used in combination with antibodies of the present invention include intercalating antibiotics and include, but are not limited to: aclarubicin, actinomycin D, amrubicin, annamycin, adriamycin, bleomycin, daunorubicin, doxorubicin, elsamitrucin, epirubicin, galarubicin, idarubicin, mitomycin C, nemorubicin, neocarzinostatin, peplomycin, pirarubicin, rebeccamycin, stimalamer, streptozocin, valrubicin, zinostatin and combinations thereof.

Plant derived anti-tumor substances that can be used in combination with antibodies of the present invention include for example those selected from mitotic inhibitors, for example vinblastine, docetaxel (Taxotere), paclitaxel and combinations thereof.

Cytotoxic topoisomerase inhibiting agents that can be used in combination with antibodies of the present invention include one or more agents selected from the group consisting of aclarubicn, amonafide, belotecan, camptothecin, 10-hydroxycamptothecin, 9-aminocamptothecin, diflomotecan, irinotecan HCl (Camptosar), edotecarin, epirubicin (Ellence), etoposide, exatecan, gimatecan, lurtotecan, mitoxantrone, pirarubicin, pixantrone, rubitecan, sobuzoxane, SN-38, tafluposide, topotecan, and combinations thereof.

Preferred cytotoxic topoisomerase inhibiting agents that can be used in combination with antibodies of the present invention include one or more agents selected from the group consisting of camptothecin, 10-hydroxycamptothecin, 9-aminocamptothecin, irinotecan HCl (Camptosar), edotecarin, epirubicin (Ellence), etoposide, SN-38, topotecan, and combinations thereof.

Immunologicals that can be used in combination with antibodies of the present invention include interferons and numerous other immune enhancing agents. Interferons include interferon alpha, interferon alpha-2a, interferon, alpha-2b, interferon beta, interferon gamma-1a, interferon gamma-1b (Actimmune), or interferon gamma-n1 and combinations thereof. Other agents include filgrastim, lentinan, sizofilan, TheraCys, ubenimex, WF-10, aldesleukin, alemtuzumab, BAM-002, dacarbazine, daclizumab, denileukin, gemtuzumab ozogamicin, ibritumomab, imiquimod, lenograstim, lentinan, melanoma vaccine (Corixa), molgramostim, OncoVAX-CL, sargramostim, tasonermin, tecleukin, thymalasin, tositumomab, Virulizin, Z-100, epratuzumab, mitumomab, oregovomab, pemtumomab (Y-muHMFG1), Provenge (Dendreon) and combinations thereof.

Biological response modifiers are agents that modify defense mechanisms of living organisms or biological responses, such as survival, growth, or differentiation of tissue cells to direct them to have anti-tumor activity. Such agents include krestin, lentinan, sizofuran, picibanil, ubenimex and combinations thereof.

Other anticancer agents that can be used in combination with antibodies of the present invention include alitretinoin, ampligen, atrasentan bexarotene, bortezomib, Bosentan, calcitriol, exisulind, finasteride, fotemustine, ibandronic acid, miltefosine, mitoxantrone, I-asparaginase, procarbazine, dacarbazine, hydroxycarbamide, pegaspargase, pentostatin, tazarotne, Telcyta™ (TLK-286, Telik Inc.), Velcade (bortemazib, Millenium), tretinoin, and combinations thereof.

Platinum-coordinated compounds that can be used in combination with antibodies of the present invention include but are not limited to, cisplatin, carboplatin, nedaplatin, oxaliplatin, and combinations thereof.

Camptothecin derivatives that can be used in combination with antibodies of the present invention include but are not limited to camptothecin, 10-hydroxycamptothecin, 9-aminocamptothecin, irinotecan, SN-38, edotecarin, topotecan and combinations thereof.

Other antitumor agents that can be used in combination with antibodies of the present invention include mitoxantrone, I-asparaginase, procarbazine, dacarbazine, hydroxycarbamide, pentostatin, tretinoin and combinations thereof.

Anti-tumor agents capable of enhancing antitumor immune responses, such as CTLA4 (cytotoxic lymphocyte antigen 4) antibodies, and other agents capable of blocking CTLA4 may also be utilized in combination with antibodies of the present invention, such as MDX-010 (Medarex) and CTLA4 compounds disclosed in U.S. Pat. No. 6,682,736; and anti-proliferative agents such as other farnesyl protein transferase inhibitors, for example the farnesyl protein transferase inhibitors. Additionally, specific CTLA4 antibodies that can be used in combination with antibodies of the present invention include those disclosed in U.S. Pat. Nos. 6,682,736 and 6,682,736 both of which are herein incorporated by reference in their entirety.

Specific IGF1R antibodies that can be used in the combination methods of the present invention include those disclosed in WO 2002/053596, which is herein incorporated by reference in its entirety.

Specific CD40 antibodies that can be used in the present invention include those disclosed in WO 2003/040170 which is herein incorporated by reference in its entirety.

Gene therapy agents may also be employed as anti-tumor agents such as TNFerade (GeneVec), which express TNFalpha in response to radiotherapy.

In one embodiment of the present invention statins may be used in combination with an antibody of the present invention and pharmaceutical compositions thereof. Statins (HMG-CoA reducatase inhibitors) may be selected from the group consisting of Atorvastatin (Lipitor™, Pfizer Inc.), Provastatin (Pravachol™, Bristol-Myers Squibb), Lovastatin (Mevacor™, Merck Inc.), Simvastatin (Zocor™, Merck Inc.), Fluvastatin (Lescol™, Novartis), Cerivastatin (Baycol™, Bayer), Rosuvastatin (Crestor™, AstraZeneca), Lovostatin and Niacin (Advicor™, Kos Pharmaceuticals), derivatives and combinations thereof.

In a preferred embodiment the statin is selected from the group consisting of Atovorstatin and Lovastatin, derivatives and combinations thereof. Other agents useful as anti-tumor agents include Caduet.

For any of the methods of treating a hyperproliferative disorder or abnormal cell growth as described herein using a combination of a P-cadherin antibody or antigen binding portion with at least one additional therapeutic agent, the P-cadherin antibody can be conjugated, or derivatized, with the additional therapeutic agent. The at least one additional therapeutic agent can also be administered separately, or in a non-derivatized or non-conjugated manner. When the at least one additional therapeutic agent is not derivatized or conjugated to the antibody, it can be administered within the same pharmaceutical formulation as the antibody, or it can be administered in a separate formulation.

Gene Therapy

The nucleic acid molecules that encode the antibodies and antibody portions of the present invention can be administered to a patient in need thereof via gene therapy. The therapy may be either in vivo or ex vivo. In a preferred embodiment, nucleic acid molecules encoding both a heavy chain and a light chain are administered to a patient. In a more preferred embodiment, the nucleic acid molecules are administered such that they are stably integrated into chromosomes of B cells because these cells are specialized for producing antibodies. In a preferred embodiment, precursor B cells are transfected or infected ex vivo and re-transplanted into a patient in need thereof. In another embodiment, precursor B cells or other cells are infected in vivo using a virus known to infect the cell type of interest. Typical vectors used for gene therapy include liposomes, plasmids, and viral vectors. Exemplary viral vectors are retroviruses, adenoviruses and adeno-associated viruses. After infection either in vivo or ex vivo, levels of antibody expression can be monitored by taking a sample from the treated patient and using any immunoassay known in the art or discussed herein.

In a preferred embodiment, the gene therapy method comprises the steps of administering an isolated nucleic acid molecule encoding the heavy chain or an antigen-binding portion thereof of a P-cadherin antibody and expressing the nucleic acid molecule. In another embodiment, the gene therapy method comprises the steps of administering an isolated nucleic acid molecule encoding the light chain or an antigen-binding portion thereof of a P-cadherin antibody and expressing the nucleic acid molecule. In a more preferred method, the gene therapy method comprises the steps of administering an isolated nucleic acid molecule encoding the heavy chain or an antigen-binding portion thereof and an isolated nucleic acid molecule encoding the light chain or the antigen-binding portion thereof of a P-cadherin antibody of the invention and expressing the nucleic acid molecules. The gene therapy method may also comprise the step of administering another therapeutic agent, such as any of the agents discussed previously in connection with combination therapy.

In order that this invention may be better understood, the following examples are set forth. These examples are for purposes of illustration only and are not to be construed as limiting the scope of the invention in any manner.

EXAMPLES

In the following examples and preparations, "BSA" means bovine serum albumin; "EDTA" means ethylenediaminetetraacetic acid; "DMSO" means dimethyl sulfoxide; "MOPS" means 3-(N-morpholino) propanesulfonic acid; "MES" means 2-(N-Morpholino)ethanesulfonic acid; "PBS" means phosphate buffered saline; "dPBS" means Dulbecco's phosphate buffered saline; "HEMA" means 2-hydroxy-ethyl methacrylate; "DMEM" means Dulbecco's modified eagle's medium; "FBS" means fetal bovine serum; "NEAA" means non-essential amino acids; "HEPES" means N-2-hydroxyethylpiperazine-N'-2-ethanesulfonic acid; and "DMF" means dimethyl formamide.

Example 1

Screening a scFv Phage Display Library

Recombinant human P-cadherin (R&D Systems 861-PC-100) was used as the antigen to screen a scFv phage display library. Large scFv human antibody libraries cloned into a phagemid vector were used for selections (Vaughan, T. J. et al., *Nat. Biotech.* 14:309-314 (1996)). ScFv which recognized P-cadherin were isolated from phage display libraries in a series of repeated selection cycles on recombinant human P-cadherin and confluent monolayers of HCT116 cells expressing P-cadherin. In brief, following incubation with the library, bound phage were recovered from P-cadherin and unbound phage were washed away. Bound phage were then rescued as described in Vaughan, T. J. et al., *Nat. Biotech.* 14:309-314 (1996) and the selection process was repeated. A representative proportion of clones from the output of selection rounds were subjected to phage enzyme-linked immunosorbent assay (ELISA) to test for binding to P-cadherin, essentially as described in Vaughan, T. J. et al., *Nat. Biotech.* 14:309-314 (1996). Two different antigens were used in the ELISA: recombinant human P-cadherin (R&D Systems) and confluent monolayers of A431 cells expressing P-cadherin. ELISA-positive clones were subjected to DNA sequencing as described in Vaughan, T. J. et al., *Nat. Biotech.* 14:309-314 (1996) and in Osbourn, J. K. et al., *Immunotechnology* 3:293-302 (1998). Unique ELISA-positive clones were converted to whole IgG molecules and tested for their ability to neutralize P-cadherin in the P-cadherin dependent adhesion assay described in Example 4. Based on the results of this screening, the antibody 129-1c4 (1050 of 1-3 µM in the A431 adhesion assay) was selected as the lead parent lineage for further optimization.

Example 2

Lead Optimization

Phage display libraries derived from 129-1c4 were created by oligonucleotide-directed mutagenesis of antibody variable heavy ($V_H$) and variable light ($V_L$) chain CDR3 regions. The libraries were constructed using standard molecular biology techniques as described in Clackson and Lowman, *Phage Display—A Practical Approach* (Oxford University Press 2004). Affinity-based selections were performed whereby; following incubation with the library, the recombinant human P-cadherin (R&D Systems) was captured by protein G-coated paramagnetic beads (Dynal 100.03) and bound phage were recovered by magnetic separation while unbound complexes were washed away. The selection process was repeated with decreasing concentrations of recombinant human P-cadherin (25 nM to 10 pM over 4 rounds) present during the selection. In addition, selection outputs from the $V_H$ CDR3 and $V_L$ CDR3 libraries were recombined into further phage display libraries and selected over two more rounds of affinity-based selection. Representative proportions of clones from the outputs of selection rounds were subjected to screening as scFv in the 129-1c4 epitope competition assay, as described in Example 8.

Example 3

P-Cadherin-Dependent Adhesion Assay

The following protocol was used to determine $IC_{50}$ values in a P-cadherin-dependent adhesion assay using several optimized scFvs that were converted to IgG during the optimization phase of antibody discovery as described above in Example 2. The mean measured $IC_{50}$ values for these antibodies are shown below in Table 4.

Recombinant human P-cadherin Fc (R&D Cat. 861-PC) was reconstituted to a concentration of 1 mg/mL with 2 mM $CaCl_2$ in MilliQ water 24 hours prior to use and stored at 4° C. A431 cells were cultured and prepared as follows. A431 cells (ECACC No. 85090402) were routinely cultured in Nunc triple flasks (3×175 $cm^2$ area) in minimal essential medium (MEM) (Invitrogen Cat 31095), containing 10% fetal bovine serum (Invitrogen Cat. 10100-147) and 1% non-essential amino acids (Invitrogen Cat. 11140-035). The cultured cells were approximately 80% confluent at the time of harvest for use in the assay. To safeguard against possible passage related effects, cells were routinely used between passage 4 and 8 and harvested after either 48 or 72 hours culture. A431 cells were harvested with 0.25% trypsin/1 mM EDTA (Gibco Cat 25200-056) for just enough time for the cells to dissociate (7-10 min) and then immediately diluted into tissue culture media to a density of approximately $2×10^6$ cells/mL. The A431 cells were then centrifuged (1200 rpm), re-suspended into assay buffer (Hanks balanced salts solution (without $Mg^{2+}$ and $Ca^{2+}$, without phenol red) (Invitrogen Cat. 14175-053) supplemented to a final $CaCl_2$ final concentration of 1 mM) re-centrifuged and re-suspended into assay buffer again at a final density of $2×10^6$ cells/mL.

Preparation of IgG serial dilutions and pre-incubation with A431 cells was performed as follows. 180 µL of each test IgG, or portion thereof, was supplemented with 20 µL of assay buffer containing 10% BSA (Sigma Cat. A-9576) to standardize the BSA concentration to 1%. An anti-murine/human P-cadherin reference polyclonal antibody (R&D Cat. AF-761) was initially resuspended into MilliQ water to give a 1 mg/mL stock. 40 µL of this stock solution was then further diluted into 140 µL of assay buffer. 20 µL of assay buffer containing 10% BSA was then added to give 200 µL at 0.2 mg/mL antibody and 0.1% BSA. Duplicate serial dilutions were prepared by first adding 2×90 µL of AF-761 polyclonal antibody or test IgG to column 1 of a Greiner 96 well polypropylene dilution plate (Greiner Cat. 780271). 60 µL of assay buffer was then added to columns 2-11. A 30 µL into 60 µL (1:3) dilution was then prepared across the plate from left to right from columns 1-11. 60 µL of assay buffer alone was then added to wells 12 A-D to define maximum adhesion. Minimum adhesion was defined by addition of 60 μL of 25 mM EDTA (in assay buffer) to wells 12 E-H. 60 μL of A431 cell suspension ($2\times10^6$ cells/mL in assay buffer—prepared as outlined above) was then added to all wells and, after agitation, the plates were pre-incubated for 1 hr at 37° C.

In parallel with the preparation of test IgG serial dilutions and pre-incubation with A431 cells, P-cadherin coated assay plates were prepared as follows. Recombinant human P-cadherin Fc was diluted in coating buffer (PBS without $Mg^{2+}$ and $Ca^{2+}$-Invitrogen Cat. 14190-094) to a concentration of 10 μg/mL and dispensed onto Fluoronunc 96 (Nunc Cat. 437958) well assay plates (100 μL/well). Plates were then incubated for 1 hr 30 min. at room temperature. The plates were then washed 3 times with PBS using a Tecan 96 plate washer. 200 μL/well of assay buffer was then added for blocking and the plates were incubated for an additional 1 hr at room temperature. The plates were then washed 3 times with PBS as described previously.

100 μL/well of the preincubated IgG/A431 material was then transferred from the Greiner 96 well dilution plates to the P-cadherin coated assay plates. At the time of transfer the IgG/A431 material was mixed by pipetting to ensure the cells were homogeneous. The adhesion process was then allowed to occur by incubating the assay plates at 37° C. for 30-45 minutes. At the end of the incubation, non-adherent cells were removed by gently aspirating the media from the plates and refilling the wells with cell wash buffer (Hanks balanced salts solution (without $Mg^{2+}$ and $Ca^{2+}$ and without phenol red—Invitrogen Cat. 14175-053) supplemented to 1 mM $CaCl_2$ final concentration). The plates were then inverted on a bath of cell wash buffer for 15 min. to remove residual non-adherent cells. At the end of this incubation, the contents of the wells were gently aspirated.

The quantitation of adherent cells was performed as follows. Adherent cells were detected by addition of 100 μL/well of combined lysis/alkaline phosphatase detection reagent (diethanolamine substrate buffer 5× concentrate (Pierce Cat. 34064) diluted 1:5 with water, after which one 15 mg PNPP tablet (Sigma Cat. N-2640) was dissolved per 25 mL of 1× solution) followed by incubation for 30-60 min. at 37° C. The reaction was then stopped by addition of 1 M NaOH (50 μL/well), aiming to give a maximum OD value of about 0.8 in the absence of inhibition. Absorbance at 405 nm was then measured using a standard plate reader.

The results were then analyzed as follows. Taking column 12, wells A-D as 100% adhesion and column 12, wells E-H as 0% adhesion, the raw data was first converted to % adhesion values as follows:

% adhesion={(value−min adhesion)/(max−min adhesion)}*100

The % adhesion versus concentration of IgG inhibitor was then plotted and $IC_{50}$ values determined using Prism software. Where partial inhibition was observed, the $IC_{50}$ is quoted as the concentration of IgG giving a true 50% inhibition as opposed to the curve mid-point. $IC_{50}$ values are reported in Table 4.

TABLE 4

| IgG | A431 Adhesion Assay Mean $IC_{50}$ (nM) (n = 3) |
|---|---|
| 194-e06 | 0.162 |
| 194-a02 | 0.217 |
| 194-b09 | 0.229 |
| 195-e11 | 0.114 |

TABLE 4-continued

| IgG | A431 Adhesion Assay Mean $IC_{50}$ (nM) (n = 3) |
|---|---|
| 194-g09 | 0.158 |
| 196-h02 | 0.148 |
| 194-e01 | 0.147 |
| 196-d10 | 0.080 |
| 196-g03 | 0.149 |
| 196-e06 | 0.117 |
| 195-a09 | 0.114 |
| 198-a09 | 0.097 |
| 200-h06 | 0.168 |

Two separate A431 adhesion assays were performed to investigate several germlined optimized IgGs from the 129-1c4 lineage in comparison with their non-germlined equivalents. For these experiments, it was necessary to change to a new batch of P-cadherin (CFR-134041), which appears to be associated with slightly increased $IC_{50}$ values compared with other data. Meaned data for several germlined IgGs from the two experiments are shown in Table 5. As noted previously, g-194-b09 refers to the germlined version of 194-b09, and so forth.

TABLE 5

| IgG | A431 Adhesion Assay Mean $IC_{50}$ (nM) (n = 2) |
|---|---|
| g-194-b09 | 0.77 |
| 194-b09 | 2.10 |
| g-194-g09 | 1.00 |
| 194-g09 | 0.73 |
| g-196-g03 | 1.05 |
| 196-g03 | 0.39 |
| g-194-e06 | 0.77 |
| 194-e06 | 0.46 |
| g-195-e11 | 0.87 |
| 195-e11 | 0.97 |
| g-200-h06 | 1.31 |
| 200-h06 | 0.63 |

Example 4

P-Cadherin-Dependent Cell Aggregation Assay

The following protocol was used to determine $IC_{50}$ values in a P-cadherin-dependent aggregation assay using several optimized scFvs that were converted to IgG during the optimization phase of antibody discovery as described above in Example 2. Because P-cadherin over-expressing cell lines form tight multicellular aggregates when placed in suspension growth, cell aggregation can be measured in the presence of P-cadherin antibodies that interfere with cellular aggregation. The mean measured $IC_{50}$ values for several antibodies are shown below in Table 6.

Plate preparation was performed as follows. Each 96 well assay plate was coated with 50 L polyHEMA (12 mg/mL in 90% ethanol, 10% methanol) and then evaporated for 6 hrs to overnight, followed by washing 3×100 L sterile $H_2O$ before use. Cells were then cultured as follows. Cells from the human cell line SW480 (stably expressing P-cadherin G418$^r$) were passaged in full growth medium (qs DMEM (in Vitrogen 11995-065), 10% FBS (Omega Scientific FB-02), 1:100 NEAA (InVitrogen 11140-050), 1:100 sodium pyruvate (InVitrogen 11360-070), 1:100 glutamine (InVitrogen 25030-051), 1:100 penicillin/streptolysin (InVitrogen 15070-063), 1:100, geneticin 50 mg/mL (Invitrogen 10131-035))+G418

(500 g/mL, then split 1:3-4 twice per week. Cultures were then frozen in growth medium+10% DMSO.

On Day 1 the SW480:pCAD cells and control SW480: pCLNX (control vector stable) were seeded at $5 \times 10^6$ cells/100 mm dish, at no more than 1:3 dilution. Cells were then grown for 48 hours in culture. Each 100 mm dish provided approximately $10 \times 10^6$ cells, or enough for $2 \times 96$ well plates.

On Day 3, the medium was removed, followed by washing with dPBS (Dulbecco's PBS (InVitrogen 14040-133)), after which the cells were trypsinized in 3 mL/100 mm dish. Neutralization was then carried out after release with two volumes (6 mL) of full growth medium. The plate was then washed three times using a pipet with 10 mL to disrupt the clusters. Cells were then counted and a pellet was obtained using a Beckman centrifuge at 1000 rpm for 5 minutes. The media was then aspirated, the pellet resuspended first in <1 mL full growth medium by finger vortex, then p1000 pipet, then the cell concentration was normalized to 1.3 M/mL. Single cell dispersion was assured by microscopy.

A reagent plate was then prepared by blocking a 96-well plate with dPBS and 5% FBS for 30 min. The plate was then washed using $1 \times 100$ L dPBS, followed by aspiration and flick to dry. A dilution series of test IgG was prepared with dPBS, using $4 \times$[IgG] concentration, enough for 3 wells of treatment plate in one well of the 96 well. 40 000 cells in 30 L/well were aliquotted to a 96 well, washed, poly-HEMA coated Costar3590 non-tissue culture plate (Corning 3590). 10 L of reagent was then transferred to each well of the 96 well plate. Triplicate samples per treatment were performed using an 8 channel pipet. Incubation then occurred at 250 rpm, shaken, in a humidified 37° C., 5% $CO_2$ incubator overnight (16-18 hr).

On day 4, 40 L of shaken cells were transferred to a poly-lysine-coated 96 well plate (BioCoat poly-lysine-coated 96 well plate: BD 356516). The wells were then rinsed with 60 L full growth medium, the plate shaken by tapping, and transferred to the poly-lysine-coated plate. If necessary, an additional 50 L wash was carried out. Incubation followed for 60 minutes in a humidified 37° C., 5% $CO_2$ incubator. Care was taken at this step to quantitatively transfer all of the cells, as gently as possible, without excess pipetting. Cells were then fixed by adding 100 L of fixing solution (7.4% formaldehyde (37% wt/vol.—Sigma F15587)) in a fume hood, followed by incubation for >30 minutes at room temperature.

To wash the cells, liquid was then decanted into a collection beaker or tray and flicked to remove remaining liquid, and tapped gently on a paper towel. 100 L per well dPBS was then applied to wash, followed by incubation for 15 min. The cells were then stained by decanting as above and applying 100 L Hoescht (1 g/mL Hoescht in dPBS—Hoescht 10 mg/mL Molecular Probes 33342), followed by incubation for 30 min. The cells were then washed twice, leaving the remaining 100 L dPBS in the well for microscopy.

The number of aggregated objects per well was then measured (Cellomics) and an average object count (with test IgG) was compared to that of IgG (e.g. Gt-anti-P-cadherin R&D Systems AF761) or media alone control. The object count versus concentration of IgG inhibitor was then plotted and $IC_{50}$ values determined. The $IC_{50}$ values for several antibodies of the present invention are reported in Table 6.

TABLE 6

| IgG | SW480 Aggregation Assay Mean $IC_{50}$ (nM)) |
|---|---|
| 194-e06 | 0.7 |
| 194-a02 | 1.1 |
| g-194-b09 | 0.9 |
| g-195-e11 | 2.2 |

TABLE 6-continued

| IgG | SW480 Aggregation Assay Mean $IC_{50}$ (nM)) |
|---|---|
| g-194-g09 | 2.6 |
| 196-h02 | 3.2 |
| 194-e01 | 1.3 |
| 196-d10 | 1.5 |
| g-196-g03 | 0.9 |
| 196-e06 | 1.9 |
| 195-a09 | 1.7 |
| 198-a09 | 2.9 |
| g-200-h06 | 4.7 |
| 129-1c4 | 35 |

Example 5

P-Cadherin-Dependent Spheroid Disruption Assay

The following spheroid disruption assay is a variation of the aggregation assay (described in Example 4) in which the cell aggregates are formed overnight prior to addition of P-cadherin and control antibodies. Test reagents are then added for an additional 24 hours before analysis.

Plate preparation was performed in the following manner. Each 96 well assay plate was coated with 50 L polyHEMA (12 mg/mL in 90% ethanol, 10% methanol) and then evaporated for 6 hrs to overnight, followed by washing $3 \times 100$ L sterile $H_2O$ before use. Cells were then cultured as follows. Cells from the human cell line SW480 (stably expressing P-cadherin G418$^r$) were passaged in full growth medium (qs DMEM (InVitrogen 11995-065), 10% FBS (Omega Scientific FB-02), 1:100 NEAA (InVitrogen 11140-050), 1:100 sodium pyruvate (InVitrogen 11360-070), 1:100 glutamine (InVitrogen 25030-051), 1:100 penicillin/streptolysin (InVitrogen 15070-063), 1:100, geneticin 50 mg/mL (Invitrogen 10131-035))+G418 (500 g/mL), then split 1:3-4 twice per week. Cultures were then frozen in growth medium+10% DMSO.

On Day 1 the SW480:pCAD cells and control SW480: pCLNX (control vector stable) were seeded at $5 \times 10^6$ cells/100 mm dish, at no more than 1:3 dilution. Cells were then grown for 48 hours in culture. Each 100 mm dish provided approximately $10 \times 10^6$ cells, or enough for $2 \times 96$ well plates.

On Day 3, the medium was removed, followed by washing with dPBS (Dulbecco's PBS (InVitrogen 14040-133)), after which the cells were trypsinized in 3 mL/100 mm dish. Neutralization was then carried out after release with two volumes (6 mL) of full growth medium. The plate was then washed three times using a pipet with 10 mL to disrupt the clusters. Cells were then counted and obtained a pellet using a Beckman centrifuge at 1000 rpm for 5 minutes. The media was then aspirated, the pellet resuspended first in <1 mL full growth medium by finger vortex, then p1000 pipet, then the cell concentration was normalized to $1.0 \times 10^6$/mL. Single cell dispersion was assured by microscopy.

40 000 cells in 40 μL/well were aliquotted to a 96 well, washed, poly-HEMA coated Costar3590 non-tissue culture plate (Corning 3590). Incubation then occurred at 250 rpm, shaken, in a humidified 37° C., 5% $CO_2$ incubator overnight (16-18 hr).

On day 4, a reagent plate was then prepared by blocking a 96-well plate with dPBS and 5% FBS for 30 min. The plate was then washed using $1 \times 100$ μL dPBS, followed by aspiration and flick to dry. A dilution series of test IgG was prepared with dPBS, using $5 \times$[IgG] concentration, enough for 3 wells of treatment plate in one well of the 96 well plate. 10 μL of reagent was then transferred to each well of the 96 well plate. Triplicate samples per treatment were performed using an 8 channel pipet. Incubation then occurred at 250 rpm, shaken, in a humidified 37° C., 5% $CO_2$ incubator (20-24 h).

On day 5, 50 μL of shaken cells were transferred to a poly-lysine-coated 96 well plate (BioCoat poly-lysine-coated 96 well plate: BD 356516). The wells were then rinsed with 50 μL full growth medium, the plate shaken by tapping, and transferred to the poly-lysine-coated plate. If necessary, an additional 50 μL wash was carried out. Incubation followed for 60 minutes in a humidified 37° C., 5% $CO_2$ incubator. Care was taken at this step to quantitatively transfer all of the cells, as gently as possible, without excess pipetting. Cells were then fixed by adding 100 μL of fixing solution (7.4% formaldehyde (37% wt/vol.—Sigma F15587)) in a fume hood, followed by incubation for >30 minutes at room temperature.

To wash the cells, liquid was then decanted into a collection beaker or tray and flicked to remove remaining liquid, and tapped gently on a paper towel. 100 L per well dPBS was then applied to wash, followed by incubation for 15 min. The cells were then stained by decanting as above and applying 100 L Hoescht (1 g/mL Hoescht in dPBS—Hoescht 10 mg/mL Molecular Probes 33342), followed by incubation for 30 min. The cells were then washed twice, leaving the remaining 100 L dPBS in the well for microscopy. The number of aggregated objects per well was then measured (Cellomics) and an average object count (with test IgG) was compared to that of IgG (e.g. Gt-anti-P-cadherin R&D Systems AF761) or media alone control. The object count versus concentration of IgG inhibitor can be plotted to determine $IC_{50}$ values. Alternatively, the object count was expressed as fold disruption vs. control at one defined concentration as shown in Table 7.

TABLE 7

| IgG | SW480 Spheroid Disruption Assay Fold Increased Disruption vs Control at 5 nM |
|---|---|
| 194-e06 | 10 |
| 194-a02 | 10 |
| g-194-b09 | 10 |
| g-195-e11 | 7 |
| g-194-g09 | 14 |
| 196-h02 | 10 |
| 194-e01 | 16 |
| 196-d10 | 10 |
| g-196-g03 | 13 |
| 196-e06 | 10 |
| 195-a09 | 10 |
| 198-a09 | 13 |
| g-200-h06 | 7 |
| 129-1c4 | 4 |

Example 6

Measurement of $K_D$ and $k_{off}$ of P-Cadherin Antibodies

Affinity measures ($K_D$ and $k_{off}$) of P-Cadherin scFv single chain antibodies by surface plasmon resonance using the BIACORE™ 3000 instrument were performed as follows using the manufacturer's protocols.

To perform kinetic analyses, recombinant human P-cadherin/Fc fusion protein (hCad/Fc) and mouse P-cadherin/Fc fusion protein (mCad/Fc) were immobilized on separate flow cells of a CM5 BIACORE™ sensor chip using routine amine coupling. Surfaces were prepared using 10 mM acetate buffer pH 4.5 with 2.0 mM $CaCl_2$ as the immobilization buffer and protein densities of 5800 and 1600 RU were achieved for the hCad/Fc and mCad/Fc fusion proteins, respectively. Deactivation of unreacted N-hydroxysuccinimide esters was performed using 1 M ethanolamine hydrochloride, pH 8.5. An activated/deactivated blank surface was used as a control surface. ScFv antibody samples in running buffer were prepared at concentrations ranging from 200 to 0.78 nM (a 0 nM solution comprising running buffer alone was included as a zero reference). Samples were randomized and injected in triplicate for 1 minute each across the flow cells using HBS-P (10 mM HEPES pH 7.4, 150 mM NaCl, 0.005% Surfactant P20) with 2.0 mM $CaCl_2$ as running buffer. A flow rate of 25 L/min was used to determine affinity constants. The dissociation of the antibody was monitored for 5 minutes, the surface regenerated by a 12 second injection of 10 mM glycine-HCl pH 1.5 (25 L/min). The raw data were processed using the Scrubber (©BioLogic Software) software package and analyzed using the CLAMP (©BioLogic Software) software package. The data were fit globally to a simple 1:1 Langmuir binding model.

Table 8 lists affinity constants for the single chain anti-P-cadherin antibodies of the present invention:

TABLE 8

| scFv | hCad/Fc $K_D$ (nM) | hCad/Fc $k_{off}$ (1/s) | mCad/Fc $K_D$ (nM) | mCad/Fc $k_{off}$ (1/s) |
|---|---|---|---|---|
| 194-b09 | 4.0 | $1.9 \times 10^{-03}$ | 11 | $3.6 \times 10^{-3}$ |
| 194-g09 | 2.6 | $1.6 \times 10^{-03}$ | 1.8 | $8.1 \times 10^{-4}$ |
| 196-g03 | 1.1 | $7.0 \times 10^{-04}$ | 0.76 | $4.7 \times 10^{-4}$ |

Example 7

Determining Selectivity of P-Cadherin Antibodies

The following protocol was used to determine the selectivity of various antibodies to P-cadherin over E-cadherin.

Recombinant human P-cadherin (R&D Systems 861-PC-100) and recombinant human E-cadherin (R&D Systems 648-EC-100) were coated onto wells of Exiqon protein immobilizer plates (VWR International) at 1 μg/mL in PBS+ 0.5 mM $CaCl_2$. Sample IgG's were blocked in 3% Marvel/PBS+0.5 mM $CaCl_2$ for 1 hour before being titrated from 50 nM (7.5 μg/mL) down to 0.64 nM (0.096 μg/mL) and added in duplicate to wells coated with the two different antigens. Following overnight equilibration at 4° C., the plates were washed three times with 1×PBS/0.1% Tween+0.5 mM $CaCl_2$ then three times with 1×PBS+0.5 mM $CaCl_2$. 50 μL anti-human Fab peroxidase conjugate diluted 1:5000 in 3% Marvel/PBS+0.5 mM $CaCl_2$ was then added to each well and left to equilibrate at room temperature for 1 hour. Plates were washed three times with 1×PBS/0.1% Tween+0.5 mM $CaCl_2$ and three times with 1×PBS+0.5 mM $CaCl_2$. 50 μl 3,3',5,5'-tetramethylbenzidine (TMB; Sigma) was added to each well and reactions allowed to develop for 20 minutes before being stopped by the addition of 25 μL/well 0.5M $H_2SO_4$. Following reading of absorbance values at 450 nm, the data was analyzed using Graphpad Prism software to calculate relative $K_D$ values for each antibody for binding to P-cadherin and E-cadherin. The resulting data is summarized in Table 9.

TABLE 9

| IgG | P-cadherin $K_D$ (pM) | E-cadherin $K_D$ (pM) | $K_D(E)/K_D(P)$ |
|---|---|---|---|
| 194-a02 | 116 | 682 | 6 |
| g-194-b09 | 788 | 2156 | 3 |
| g-194-g09 | 2602 | No binding | >100 |
| 194-e01 | 112 | 20511 | 183 |
| g-194-e06 | 191 | 794 | 4 |
| 195-a09 | 120 | 11516 | 96 |
| 194-e06 | 56 | 264 | 5 |
| 196-d10 | 45 | 63 | 1.4 |
| 196-e06 | 62 | 187 | 3 |
| g-196-g03 | 449 | 7513 | 17 |
| 196-h02 | 102 | 33212 | 326 |
| 198-a09 | 78 | 19396 | 249 |

Example 8

Epitope Competition Assay

The following protocol was used to measure IC$_{50}$ values in an epitope competition assay to measure the ability of variant scFvs within a parental lineage to displace the parent IgG from native P-cadherin on the surface of A431 cells. The amount of bound biotinylated parent IgG in the presence of inhibitory scFv is detected with europium streptavidin and DELFIA quantitation. The measured IC$_{50}$ values for several scFvs are shown in Table 10.

A431 cells (ECACC No. 85090402), cultured according to standard methods, then harvested at approximately 80% confluence, were seeded at 2.5×10$^4$ cells per well in 96 well Beckton Dickenson (BD Cat. 6407) collagen coated plates the day prior to use. The plates were then washed 3 times by submersing into a PBS buffer (Gibco Cat. 14190-094, without calcium, magnesium, and sodium bicarbonate) reservoir before addition of 200 L per well of block buffer (PBS Gibco Cat. 14190-094, plus 3% Marvel (Premier International Foods Ltd.)) and incubated for 2 hours at room temperature. The plates were then washed 3 times with PBS as above.

For both high throughput screening and IC$_{50}$ profiling scFv/IgG materials were first prepared in Greiner dilution plates (Greiner 96 well polypropylene plates (Greiner Cat. 780271)) in a total volume of 60 L of assay buffer. 50 L was then transferred from the slave Greiner plate directly onto the assay plate and the binding reaction was allowed to proceed for 2 hr 30 min. at room temperature. At the end of the binding reaction the plates were washed 3 times in PBS before the addition of europium labelled streptavidin (Perkin Elmer Cat. 1244-360 1:1000 dilution in DELFIA assay buffer (Perkin Elmer Cat. 4002-0010)) and incubated for a further 1 hour at room temperature.

The plates were then washed 7 times with DELFIA wash buffer (Perkin Elmer Cat. 4010-0010) by repeatedly submerging plates into a buffer reservoir. Finally, after addition of DELFIA enhancer (Perkin Elmer Cat. 4001-0010-100 L/well) plates were read using a standard DELFIA protocol on a compatible reader (e.g. Wallac or Envision).

Greiner Dilution Plate Set Up—HTS

High throughput screening (HTS) conditions were configured differently depending on the stage of the optimization. For HTS of outputs from the individual V$_H$ and V$_L$ chain optimization final [peri-prep] was fixed at 12.5% such that the parent scFv gave partial inhibition. For the later HTS of outputs from the V$_H$:V$_L$ recombination libraries final peri-prep concentration was reduced to 1.7% and under these conditions the V$_H$ optimized benchmark scFv (TOP-108-001) gave partial inhibition. The optimization of peri-prep concentration such that the relevant benchmark scFv gave partial inhibition left a window in which to identify improved clones.

To achieve these final scFv peri-prep concentrations the following procedure was adopted:
  i) Using a Cybiwell instrument, the required volume (see below) of peri-prep sample material was transferred from a deep well sample plate to a Greiner dilution plate in columns 1-11.

| [Final peri-prep] | Transfer volume |
|---|---|
| [12.5%] = | 7.5 uL |
| [1.7%] = | 10.0 uL (of 1:10 diluted peri-prep) |

(1:10 pre-diluted peri-prep was prepared by transferring 10 L of neat peri-prep from the sample plate into a Greiner dilution plate containing 90 L of assay buffer (using Cybiwell).
  ii) The volume in columns 1-11 was then made up to 30 L by addition of an appropriate volume of assay buffer.
  iii) 30 L of assay buffer was then added to column 12 (A-D) (total binding wells).
  iv) 30 L of excess unlabelled parent IgG (129-1c4) in assay buffer was added to column 12 (E-H) to define non-specific binding. This was added at 1000 nM concentration to give 500 nM final.
  v) The 129-1c4 IgG was biotinylated using the water insoluble reagent EZ-link-NHS-LC-Biotin (Perbio/Pierce product no. 21336). The IgG solution was supplemented by adding a $\frac{1}{10}^{th}$ volume of 1 M NaHCO$_3$ and a $\frac{1}{10}^{th}$ volume of dimethylformamide. The EZ-link-NHS-LC-Biotin reagent was dissolved in DMF and then added at a five-fold molar excess over IgG and the reaction allowed to proceed at room temperature for 20 minutes. The biotinylated IgG was then stabilized by addition of BSA (0.1%). 30 μL of biotinylated parent 129-1c4 IgG in assay buffer was then added to all wells to give a final concentration of 1.5 nM in the final 60 μL volume (i.e. europium labelled IgG added at 2× final concentration).
  vi) After mixing the Greiner plate contents by agitation, 50 μL was transferred directly to the assay plate and the binding reaction allowed to proceed for 2 hrs 30 min at room temperature (as described previously).

Greiner Dilution Plate Set Up—IC$_{50}$ Profiling
  i) 30 μL/well of assay buffer was added to columns 2-11 and wells 12A to 12D in standard Greiner dilution plates.
  ii) 30 μL of excess unlabelled 129-1c4 parent IgG in assay buffer was added to column 12 (E-H) to define non-specific binding. This should be added at 1000 nM concentration to give 500 nM final concentration
  iii) To column 12×45 μL of each undiluted scFv His-prep was added such that 4 duplicate 11 point IC$_{50}$ titrations could be set up per 96 well assay plate. 1:3 duplicate serial dilutions were then performed by taking 15 μL from column 1 and mixing into column 2 followed by taking 15 μL from column 2 and mixing into column 3, etc. After mixing into column 11, 15 μL was removed (i.e. to leave 30 μL final volume).
  iv) 30 μL of biotinylated 129-1c4 parent IgG in assay buffer was then added to all wells to give a final concentration of 1.5 nM in the final 60 μL volume (i.e. europium labelled IgG added at 2× final concentration).

v) After mixing the Greiner plate contents by agitation, 50 μL was then transferred directly to the assay plate and the binding reaction allowed to proceed for 2 hr 30 min at room temperature as discussed previously.

For HTS, scFv were expressed in 96 well format as crude extract from the bacterial peri-plasm (scFv peri-prep) in a base buffer containing MOPS/EDTA/Sorbitol pH 7.4 (MES pH 7.4). For $IC_{50}$ profiling, scFv were expressed in a lower throughput purified form using the scFv His-tag for affinity purification (scFv His-prep) in a base buffer of PBS.

For both HTS and $IC_{50}$ analysis, raw data was first converted to % binding data according to the following equation:

% binding={(value−non-specific binding)/(total binding−non specific binding)}*100

HTS data was then further analyzed using standard Excel templates to identify hits giving greater inhibition (lower % binding) than the relevant benchmark scFv. For $IC_{50}$ analysis, % binding data was analyzed using Prism version 4.0 curve fitting software. The scFvs are variants of the 129-1c4 parent IgG, wherein the $V_H$ and $V_L$ CDR3 regions were randomly mutated, as described in Example 2. $V_H$ CDR3 variant sequences are shown in FIG. 1 as SEQ ID NOs: 91 to 256. $V_L$ CDR3 variant sequences are shown in FIG. 1 as SEQ ID NOs: 257 to 319. The $IC_{50}$ values for several scFvs that showed improved binding over the parent 129-1c4 scFv are shown in Table 10. Each of the scFv variants of the 129-1c4 parent are identified by two SEQ ID NOs: a $V_H$ CDR3 and a $V_L$ CDR3. For reference, the $IC_{50}$ of the parent 129-1c4 IgG was 28.97 nM. For the first 26 scFvs in Table 10 (i.e. those where either the $V_H$ CDR3 is SEQ ID NO: 37, or the $V_L$ CDR3 is SEQ ID NO: 47), the $IC_{50}$ was measured with the biotinylated parent IgG at a concentration of $1 \times K_D$. For the rest of the scFvs in Table 10 (i.e. rows 27-36), the concentration of biotinylated parent IgG was increased to $3 \times K_D$ to improve assay sensitivity.

TABLE 10

| SEQ ID NO: $V_H$ CDR3 | SEQ ID NO: $V_L$ CDR3 | $IC_{50}$ (nM) |
| --- | --- | --- |
| 37 | 40 | 2.49 |
| 37 | 261 | 1.78 |

TABLE 10-continued

| SEQ ID NO: $V_H$ CDR3 | SEQ ID NO: $V_L$ CDR3 | $IC_{50}$ (nM) |
| --- | --- | --- |
| 37 | 43 | 5.67 |
| 37 | 274 | 8.73 |
| 37 | 277 | 2.20 |
| 37 | 287 | 10.50 |
| 37 | 288 | 6.67 |
| 37 | 295 | 0.80 |
| 37 | 297 | 2.49 |
| 37 | 299 | 1.97 |
| 37 | 303 | 1.47 |
| 37 | 304 | 1.10 |
| 37 | 305 | 2.19 |
| 95 | 47 | 2.36 |
| 97 | 47 | 1.33 |
| 113 | 47 | 2.06 |
| 125 | 47 | 0.26 |
| 131 | 47 | 0.35 |
| 31 | 47 | 2.05 |
| 147 | 47 | 1.16 |
| 165 | 47 | 5.11 |
| 167 | 47 | 0.60 |
| 180 | 47 | 0.43 |
| 181 | 47 | 2.46 |
| 27 | 47 | 0.54 |
| 195 | 47 | 1.29 |
| 187 | 43 | 1.58 |
| 27 | 296 | 1.16 |
| 163 | 43 | 2.45 |
| 26 | 40 | 0.76 |
| 26 | 43 | 0.93 |
| 27 | 309 | 1.36 |
| 199 | 310 | 2.54 |
| 201 | 310 | 2.26 |
| 207 | 291 | 2.73 |
| 240 | 313 | 2.98 |

All publications, patents, and patent applications cited in this specification are incorporated herein by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

We claim:

1. An isolated antibody or antigen-binding portion thereof that binds to human P-cadherin, wherein said antibody or antigen-binding portion comprises: a) a $V_H$CDR1 comprising the amino acid sequence set forth in SEQ ID NO: 24; b) a $V_H$CDR2 comprising the amino acid sequence set forth in SEQ ID NO: 25; c) a $V_H$CDR3 comprising the amino acid sequence set forth in SEQ ID NO: 27; d) a $V_L$CDR1 comprising the amino acid sequence set forth in SEQ ID NO: 38; e) a $V_L$CDR2 comprising the amino acid sequence set forth in SEQ ID NO: 39; and f) a $V_L$CDR3 comprising the amino acid sequence set forth in SEQ ID NO: 41.

2. The antibody or antigen-binding portion thereof according to claim 1, comprising a $V_H$ domain, wherein the $V_H$ domain amino acid sequence comprises the amino acid sequence set forth in SEQ ID NO: 320.

3. The antibody or antigen-binding portion thereof according to claim 1, comprising a $V_L$ domain, wherein the $V_L$ domain amino acid sequence comprises the amino acid sequence set forth in SEQ ID NO: 326.

4. The antibody or antigen-binding portion thereof according to claim 1, comprising a $V_H$ domain and a $V_L$ domain, wherein the $V_H$ domain amino acid sequence comprises the amino acid sequence set forth in SEQ ID NO: 320 and wherein the $V_L$ domain amino acid sequence comprises the amino acid set forth in SEQ ID NO: 326.

5. An isolated antibody comprising a $V_H$ domain and a $V_L$ domain wherein the $V_H$ domain amino acid sequence comprises the amino acid sequence set forth in SEQ ID NO: 320 and wherein the $V_L$ domain amino acid sequence comprises the amino acid set forth in SEQ ID NO: 326.

6. The antibody according to claim 5, wherein the heavy chain constant region comprises SEQ ID NO: 344 and wherein the light chain constant region comprises SEQ ID NO: 345, with the proviso that the C-terminal lysine residue of SEQ ID NO: 344 is optionally cleaved.

7. An isolated P-cadherin antibody or antigen-binding portion thereof, wherein said antibody is g-194-b09.

8. A pharmaceutical composition comprising the antibody or antigen-binding portion thereof according to claim 1 and a pharmaceutically acceptable carrier.

9. A pharmaceutical composition comprising the antibody or antigen-binding portion thereof according to claim 7 and a pharmaceutically acceptable carrier.

* * * * *